US010059668B2

(12) United States Patent
Vaisburg et al.

(10) Patent No.: US 10,059,668 B2
(45) Date of Patent: Aug. 28, 2018

(54) LSD1 INHIBITORS

(71) Applicant: Mirati Therapeutics, Inc., San Diego, CA (US)

(72) Inventors: Arkadii Vaisburg, Kirkland (CA); Matthew Arnold Marx, San Diego, CA (US)

(73) Assignee: Mirati Therapeutics, Inc., San Diego, CA (US)

( * ) Notice: Subject to any disclaimer, the term of this patent is extended or adjusted under 35 U.S.C. 154(b) by 0 days.

(21) Appl. No.: 15/343,027

(22) Filed: Nov. 3, 2016

(65) Prior Publication Data

US 2017/0129857 A1    May 11, 2017

Related U.S. Application Data

(60) Provisional application No. 62/251,277, filed on Nov. 5, 2015, provisional application No. 62/296,193, filed on Feb. 17, 2016.

(51) Int. Cl.
*C07D 211/58* (2006.01)
*C07D 401/10* (2006.01)
*C07D 211/34* (2006.01)

(52) U.S. Cl.
CPC .......... *C07D 211/58* (2013.01); *C07D 211/34* (2013.01); *C07D 401/10* (2013.01)

(58) Field of Classification Search
CPC ............................ C07D 211/58; C07D 401/10
USPC ........................................................ 514/326
See application file for complete search history.

(56) References Cited

U.S. PATENT DOCUMENTS

| 7,244,751 | B2 | 7/2007 | Lu et al. | |
|---|---|---|---|---|
| 9,149,447 | B2 | 10/2015 | Munoz et al. | |
| 9,255,097 | B2 | 2/2016 | Chen et al. | |
| 9,278,931 | B2 | 3/2016 | Tomita et al. | |
| 9,346,840 | B2 | 5/2016 | Johnson et al. | |
| 9,809,541 | B2 * | 11/2017 | Marx ................... | C07D 211/58 |
| 2012/0004262 | A1 | 1/2012 | Guibourt et al. | |
| 2013/0090386 | A1 | 4/2013 | Ortega Munoz et al. | |
| 2013/0231342 | A1 | 9/2013 | Ortega Munoz et al. | |
| 2013/0289076 | A1 | 10/2013 | Laria et al. | |
| 2013/0303545 | A1 | 11/2013 | Maes et al. | |
| 2014/0018393 | A1 * | 1/2014 | Johnson ................ | C07D 401/04 |
| | | | | 514/331 |
| 2014/0213657 | A1 | 7/2014 | Ortega Munoz et al. | |
| 2014/0228405 | A1 | 8/2014 | Tomita et al. | |
| 2015/0025054 | A1 | 1/2015 | Ortega Munoz et al. | |
| 2015/0119396 | A9 | 4/2015 | Ortega Munoz et al. | |
| 2015/0191427 | A1 | 7/2015 | Holson et al. | |
| 2015/0225375 | A1 | 8/2015 | Wu et al. | |
| 2015/0225379 | A1 | 8/2015 | Wu et al. | |
| 2015/0225394 | A1 | 8/2015 | Wu et al. | |
| 2015/0225401 | A1 | 8/2015 | Wu et al. | |
| 2015/0266881 | A1 | 9/2015 | Tomita et al. | |
| 2015/0291577 | A1 | 10/2015 | Matsumoto et al. | |
| 2015/0315187 | A1 | 11/2015 | Chen et al. | |
| 2016/0039748 | A1 | 2/2016 | Suzuki et al. | |
| 2016/0108046 | A1 | 4/2016 | Chen et al. | |
| 2016/0120862 | A1 | 5/2016 | Zhang | |
| 2016/0152595 | A1 | 6/2016 | Chen et al. | |
| 2017/0129857 | A1 * | 5/2017 | Vaisburg .............. | C07D 211/34 |
| 2017/0183308 | A1 * | 6/2017 | Marx ................... | C07D 205/04 |

FOREIGN PATENT DOCUMENTS

| WO | 2010/043721 A1 | 4/2010 |
|---|---|---|
| WO | WO 2011/035941 | 3/2011 |
| WO | WO 2011/042217 | 4/2011 |
| WO | WO 2012/013728 | 2/2012 |
| WO | WO 2012/107499 | 8/2012 |
| WO | WO 2012/135113 | 10/2012 |
| WO | WO 2013/057320 | 4/2013 |
| WO | WO 2014/086790 | 6/2014 |
| WO | WO 2014/164867 | 10/2014 |
| WO | WO 2015/089192 | 6/2015 |
| WO | 2015/123408 A1 | 8/2015 |
| WO | 2015/123437 A1 | 8/2015 |
| WO | WO 2016/123387 | 8/2016 |
| WO | WO 2016/130952 | 8/2016 |
| WO | WO 2016/161282 | 10/2016 |
| WO | 17/109061 A1 | 6/2017 |

OTHER PUBLICATIONS

Mohammad; Cancer Cell, 2015, 28, 4-6. (Year: 2015).*
Gallipoli; Ther Adv Hematol 2015, 6, 103-119. (Year: 2015).*
International Search Report and Written Opinion of the International Searching Authority; International Application PCT/US2016/060387; dated Feb. 1, 2017. (Year: 2017).*
Binda et al., "Biochemical, Structural and Biological Evaluation of Tranylcypromine Derivatives as Inhibitors of Histone Demethylases LSD1 and LSD2," J. Am. Chem. Soc., 2010, 132, 6827-6833.
Khan et al., "Design, synthesis and biological activity of N-alkylated analogue of NCL1, a selective inhibitor of lysine-specific demethylase 1," Med. Chem. Commun., Royal Society of Chemistry, 2014, 6 pages.
Han et al., "Novel Tranylcypromine/Hydroxylcinnamic Acid Hybrids as Lysine-Specific Demethylase 1 Inhibitors with Potent Antitumor Activity," Chem. Pharm. Bull. 63, 882-889 (2015).
Metzger et al., "LSD1 demethylates repressive histone marks to promote androgen-receptor-dependent transcription," Nature Letters, vol. 437, Sep. 15, 2005, pp. 436-439.
Mimasu et al., Structurally Designed trans-2-Phenylcyclopropylamine Derivatives Potently Inhibit Histone Demethylase LSD1/KDM1, Biochemistry, 2010, 49, 6494-6503.

(Continued)

*Primary Examiner* — Daniel R Carcanague
(74) *Attorney, Agent, or Firm* — McDonnell Boehnen Hulbert & Berghoff LLP

(57) ABSTRACT

The present invention relates to compounds that inhibit LSD1 activity. In particular, the present invention relates to compounds, pharmaceutical compositions and methods of use, such as methods of treating cancer using the compounds and pharmaceutical compositions of the present invention.

22 Claims, No Drawings

(56) References Cited

OTHER PUBLICATIONS

Mohammad et al., "A DNA Hypomethylation Signature Predicts Antitumor Activity of LSD1 Inhibitors in SCLC," CellPress, Cancer Cell 28, Jul. 13, 2015, 47 pages.
Shi et al., "Histone Demethylation Mediated by the Nuclear Amine Oxidase Homolog LSD1," Cell, vol. 119, 941-953, Dec. 29, 2004.
Suzuki et al., "Lysine Demethylases Inhibitors," J. Met Chem., 2011, 54, 8236-8250.
Vianello et al., "Discovery of a Novel Inhibitor of Histone Lysine-Specific Demethylase 1A (KDM1A/LSD1) as Orally Active Antitumor Agent," J. Med. Chem. Article, Jul. 31, 2015, 17 pages.
Vianello et al., "Discovery of a Novel Inhibitor of Histone Lysine-Specific Demethylase 1A (KDM1A/LSD1) as Orally Active Antitumor Agent," J. Med. Chem. Article, Dec. 24, 2015, 66 pages.
Adamo et al., "LSD1 regulates the balance between self-renewal and differentiation in human embryonic stem cells," Nature Cell Biology, Jun. 2011, 30 pages.
Amente et al., "LSD1-mediated demethylation of histone H3 lysine 4 triggers Myc-induced transcription," Oncogene, 2010, pp. 3691-3702, vol. 29.
Bennesch et al., "LSD1 engages a corepressor complex for the activation of the estrogen receptor α by estrogen and cAMP," Nucleic Acids Research, 2016, pp. 1-16.
Burg et al., "Lysine-Specific Demethylase 1A (KDM1A/LSD1): Product Recognition and Kinetic Analysis of Full-Length Histones," Biochemistry, 2016, pp. 1652-1662.
Cao et al., "Functinal interaction of histone deacetylase 5 (HDAC5) and lysine-specific demethylase 1 (LSD1) promotes breast cancer progression," Oncogene, 2016, pp. 1-13.
Chen et al., "Effects of cisplatin on the LSD1-mediated invasion and metastasis of prostate cancer cells," Molecular Medicine Reports, 2016, pp. 2511-2517, vol. 14.
Crunkhorn, Sarah, Nature Reviews Drug Discovery, 2015, p. 602, vol. 14 Published online Sep. 1, 2015.
Derr et al., "High nuclear expression levels of histone-modifying enzymes LSD1, HDAC2 and SIRT1 in tumor cells correlate with decreased survival and increased relapse in breast cancer patients," BMC Cancer, 2014, 20 pages.
Ding et al., "LSD1-mediated epigenetic modification colon cancer," British Journal of Cancer, 2013, pp. 994-1003, vol. 109.
Feng et al., "Phosphorylation of LSD1 at Ser112 is crucial for its function in induction of EMT and metastasis in breast cancer," Breast Cancer Res Treat, 2016, 14 pages.
Fiskus et al., "Corrigendum—Highly effective combination of LSD1 (KDM1A) antagonist and pan-histone deacetylase inhibitor against human AML cells," Leukemia, 2017, 1 page.
Fiskus et al., "Highly effective combination of LSD1 (KDM1A) antagonist and pan-histone deacetylase inhibitor against human AML cells," Leukemia, 2014, pp. 1-10.
Haydn et al., "Concomitant epigenetic targeting of LSD1 and HDAC synergistically induces mitochondrial apoptosis in rhabdomyosarcoma cells," Cell Death and Disease, 2017, 12 pages, vol. 8.
Hayward, D. and Cole, P.A., "LSD1 Histone Demethylase Assays and Inhibition," Methods in Enzymology, 2016, pp. 261-278.
Huang et al., "Lysine-Specific Demethylase 1 (LSD1/KDM1A) Contributes to Colorectal Tumorigenesis via Activation of the Wnt/B-Catenin Pathway by Down-Regulating Dickkopf-1 (DKK1)," PLoS ONE, Jul. 2013, 12 pages, vol. 8, No. 7.
Ishikawa et al., "A novel LSD1 inhibitor T-3775440 disrupts GFI1B-containing complex leading to transdifferentiation and impaired growth of AML cells," Cancer Research; 2016, 49 pages.
Janzer et al, "Lysine-specific demethylase 1 (LSD1) and histone deacetylase 1 (HDAC1) synergistically repress proinflammatory cytokines classical complement pathway components," BBRC, 2012, pp. 665-670, vol. 421.
Jin et al., "LSD1 collaborates with EZH2 to regulate expression of interferon-stimulated genes," Biomedicine & Pharmacotherapy, 2017, pp. 728-737, vol. 88.
Jin et al., "LSD1 knockdown reveals novel histone lysine methylation in human breast cancer MCF-7 cells," Biomediane and Pharmacotherapy, 2017, pp. 896-904, vol. 92.
Ketscher et al., LSD1 controls metastasis of androgen-independent prostate cancer cells through PXN and LPAR6, Oncogenesis, 2014, 9 pages, vol. 3.
Kim et al., "LSD1 is essential for oocyte meiotic progression by regulating CDC25B expression in mice," Nature Communications, 2015, pp. 1-12.
Konovalov et al., "Analysis of the levels of lysine-specific demethylase 1 (LSD1) mRNA in human ovarian tumors and the effects of chemical LSD1 inhibitors in ovarian cancer cell lines," Journal of Ovarian Research, 2013, pp. 1-15, vol. 6, No. 1.
Kozono et al., "Dynamic epigenetic regulation of glioblastoma tumorigenicity through LSD1 modulation of MYC expression," PNAS, 2015, 22 pages.
Laurent et al., "Expression, Purification, and biochemical analysis of the LSD1-KDM1A histone demethylase," Methods in Enzymology, 2016, pp. 241-259, vol. 573.
Li et al., "Discovery of [1,2,3]Triazolo[4,5-d]pyrimidine Derivatives as Novel LSD1 Inhibitors," ACS Medicinal Chemistry Letters, 2017, pp. 384-389, vol. 8.
Li et al., "Upregulated long non-coding RNA AGAP2-AS1 represses LATS2 and KLF2 expression through interacting with EZH2 and LSD1 in non-small-cell lung cancer cells," Cell Death and Disease, 2016, 11 pages, vol. 7.
Li et al., "HBXIP and LSD1 scaffolded by lncRNA Hotair mediates transcriptional activation by c-Myc," Cancer Research, 2015, 40 pages.
Lim et al., "Lysine-specific demethylase 1 (LSD1) is highly expressed in ER-negative breast cancers and a biomarker preclichng aggressive biology," Carcinogenesis, 2010, pp. 512-520, vol. 31, No. 3.
Luo et al., "MOF Acetylates the Histone Demethylase LSD1 to Suppress Spithelial-to-Mesenchymal Transition," Cell Reports, Jun. 21, 2016, pp. 1-14, vol. 15.
Lv et al., "Over-Expression of LSD1 Promotes Proliferation, Migration and Invasion in Non-Small Cell Lung Cancer," PLoS ONE, Apr. 2012, pp. 1-8, vol. 7, No. 4.
Lynch et al., "CD86 expression as a surogate cellular biomarker for pharmacological inhibition of the histone demethylase lysine-specific demthylase 1," Analytical Biochemistry, 2013, pp. 104-106, vol. 442.
Lynch et al., "LSD1 inhibition a therapeutic strategy in cancer," Expert Opinion on Therapeutic Targets, 2012, pp. 1239-1249.
Ma et al., "Design, synthesis and structure-activity relationship of novel LSD1 inhibitors based on pyrimidine-thiourea hybrids as potent, orally active antitumor agents," J Med Chem,, 2015, 36 pages.
Maiques-Diaz et al., "LSD1 biologic roles and therapeutic targeting," Epigenomics, 2016, 14 pages.
Marabelli et al., "The growing structural and functional complexity of the LSD1-KDM1A histone demethylase," Structural Biology, 2016, pp. 135-144, vol. 41.
Marango et al., "The MMSET protein is a histone methyltransferase with characteristics of a transcriptional corepressor," Blood, Mar. 15, 2008, pp. 3145-3154, vol. 111, No. 6.
Mohammad et al., "Antitumor activity of LSD1 inhibitors in lung cancer," Molecular and Cellular Oncology, 2016, 4 pages, vol. 3, No. 2.
Mould et al., "Reversible inhibitors of LSD1 as therapeutics agents in acute myeloid leukemia clinical significance and progress to date," Medicinal Research Reviews, 2015, pp. 586-618.
Nalawansha et al., "LSD1 Substrate Binding and Gene Expression Are Affected by HDAC1-Mediated Deacetylation," ACS Chemical Biology; 2016, pp. A-K.
Niebel et al., "Lysine-specific demethylase 1 (LSD1) in hematopoietic and lymphoid neoplasms," Blood, 2014, pp. 151-152, vol. 124, No. 1.
Pieroni et al., "Further insights into the SAR of α-substituted cyclopropylamine derivatives as inhibitors of histone demethylase KDM1A," European Journal of Medicinal Chemistry, 2015, pp. 377-386, vol. 92.

(56) References Cited

OTHER PUBLICATIONS

Pilotto et al., "Interplay among nucleosomal DNA, histone tails, and corepressor CoREST underlies LSD1-mediated H3 demethylation," PNAS, 2015, pp. 2752-2757, vol. 112, No. 9.
Pilotto et al., "LSD1 KDM1A mutations associated to a newly described form of intellectual disability impair demethylase activity and binding to transcription factors," HMG, 2016, 33 pages.
Prusevich et al., "A Selective Phenelzine Analogue Inhibior of Histone Demethylase LSD1," ACS Chemical Biology and Supplementary Information, 2014, 115 pages.
Przespoleswki et al., "Inhibitors of LSD1 as a potential therapy for acute myeloid leukemia," Expert Opinion on Investigational Drugs, 2016, pp. 771-780, vol. 25, No. 7.
Rudolph et al., "Lysine-specific histone demethylase LSD1 and the dynamic control of chromatin," Biological Chemistry, 2013, pp. 1019-1028, vol. 394, No. 8.
Sartori et al., "Thieno[3,2-b]pyrrole-5-carboxamides as New Reversible Inhibitors of Histone Lysine Demethylase KDM1A-LSD1 Part 1 High Throughput Screening and Preliminary Exploration," JMC, 2017, 80 pages.
Sharma et al., "Growth Inhibition of SCLC Cell Lines by LSD1 Inhibitors is Associated with Modulation of Neuroendocrine and Mesenchymal Pathways," Keystone Conference Poster, 2016, 1 page.
Shin et al., "Molecular Toggle Switch of Histone Demethylase LSD1," Molecular Cell, 2015, 2 pages.
Shixian et al., "Lysine-specific demethylase 1 promotes tumorigenesis and predicts prognosis in gallbladder cancer," Oncotarget, 2015, 12 pages.
Golub et al., "Molecular Classification of Cancer: Class Discovery and Class Prediction by Gene Expression Monitoring", Science, 1999, vol. 286, 531-537.
Lala et al., "Role of nitric oxide in tumor progression: Lessons from experimental tumors", Cancer and Metastasis Reviews, 1998, 17(1), 91-106.
Cancer. Medline Plus: Trusted Health Information for You [online], [retrieved on Jul. 6, 2007]. Retrieved from the internet, <URL http://www.nlm.nih.gov/medlineplus/cancer.html>, 10 pages.
Singh et al., "Preclinical activity of combined HDAC and KDM1A inhibition in glioblastoma," Neuro-Oncology, 2015, 11 pages.
Stewart et al., "Altering the course of Small cell lung cancer Targeting cancer stem cells via LSD1 inhibition," Cancer Cell, Jul. 13, 2015, pp. 4-6, vol. 28.
Sugino et al., A novel LSD1 inhibitor NCD38 ameliorates MDS-related leukemia with complex karyotype by attenuating leukemia programs via activating super-enhancers, Leukemia accepted article preview, Feb. 17, 2017, 53 pages, doi: 10.1038/leu.2017.59.
Sun et al., "LncRNA HOXA11-AS promotes proliferation and invasion of gastric cancer by scaffolding the chromatin modification factors PRC2, LSD1 and DNMT1," Cancer Research, 2016, 37 pages.
Takagi et al., "LSD1 inhibitor T-3775440 inhibits SCLC cell proliferation by disrupting LDS1 interactions with SNAG domain proteins INSM1 and GFI1B," Cancer Research, 2017, 36 pages.
Thambyrajah et al., "GFI1 proteins orchestrate the emergence of haematopoietic stem cells through recruitment of LSD1," Nature Cell Biology, 2015, pp. 21-34, vol. 18, No. 1.
Valente et al., "Pure disastereomers of a tranylcypromine-based LSD1 inhibitor enzyme selectivity and in-cell studies," ACS Med Chem 2014, pp. 173-177, vol. 6.
Velinder et al., "GFI1 functions in transcriptional control and cell fate determination require SNAG domain methylation to recruit LSD1," Biochemical Journal, 2016, 40 pages.
Wang et al., Design, synthesis and biological evaluation of [1,2,4]triazolo[1,5-a]pyrimidines as potent lysine specific demethylase 1 (LSD1/KDM1A) inhibitors, European Journal of Medicinal Chemistry, 2016, 29 pages, doi: 10.1016/j.ejmech.2016.10.021.
Wang et al., "Inhibition of LSD1 by pargyline inhibited process of EMT and delayed progression of prostate cancer in vivo," BBRC, 2015, pp. 310-315, vol. 467.
Wang et al., "Relationship between LSD1 expression and E-cadherin expression in prostate cancer," Int Urol Nephrol., 2015, pp. 485-490, vol. 47.
Wang et al., The histone demethylase LSD1 is a novel oncogene and therapeutic target in oral cancer, Cancer Letters, 2016, pp. 12-21, vol. 374.
Whyte et al., "Enhancer decommissioning by LSD1 during embryonic stem cell differentiation," Nature, 2012, pp. 221-225, vol. 482.
Wissmann et al., "Cooperative demethylation by JMJD2C and LSD1 promotes androgen receptor-dependent gene expression," Nature Cell Biology, 2007, 12 pages, vol. 9, No. 3.
Zhang et al., "Pluripotent stem cell protien Sox2 confers sensitivity to LSD1 inhibition in cancer cells," Cell, 2013, pp. 445-457, vol. 5.
Zhou et al., "Identification of novel selective LSD1 inhibitors using a pharmacophore based virtual screening combined with docking," Chemical Biology and Drug Design, 2014, 29 pages.
Zhou et al., "Synthesis and biological evaluation of novel (E)-N'-(2,3-dihydro-1H-inden-1-ylidene) benzohydrazides as potent LSD1 inhibitors," Bioorganic Medicinal Chemistry Letters, 2015, 2016, pp. 4552-4557, vol. 26.

\* cited by examiner

LSD1 INHIBITORS

CROSS REFERENCE

This application claims benefit of U.S. Provisional Application No. 62/251,277, filed Nov. 5, 2015, and U.S. Provisional Application No. 62/296,193, filed Feb. 17, 2016, the entire content of each application is hereby incorporated by reference in their entirety.

FIELD OF THE INVENTION

The present invention relates to compounds that inhibit lysine-specific demethylase one (LSD1). In particular, the present invention relates to compounds that irreversibly inhibit the activity of LSD1, pharmaceutical compositions comprising the compounds and methods of use therefor.

BACKGROUND OF THE INVENTION

Lysine-specific demethylase one ("LSD1"), also known as KDM1A, is a flavin-dependent lysine demethylase that removes methyl groups from mono- and dimethylated lysine4 of the histone H3 protein through flavin adenine dinucleotide (FAD) dependent enzymatic oxidation (e.g., see Shi et al., (2004) Cell 119:941-953). In addition, LSD1 demethylates mono- and dimethylated of histone H3 lysine9 in prostate cancer cell lines and is essential for transcriptional regulation mediated by the androgen receptor (Metzger et al., Nature (2005) 437:436-439). LSD1 also demethylates a number of cellular proteins, such as p53, E2F1 and STAT3 and regulates their function.

LSD1 has been reported to be overexpressed in a wide variety of cancers and tissues, including lung cancer, bladder cancer, neuroblastoma, prostate cancer and breast cancer. LSD1 is thought to play a role in cellular proliferation and cancer cell growth by modulating prosurvival gene expression and p53 transcriptional activity (e.g., see Suzuki and Miyata (2011) J. Med. Chem. 54:8236-8250). LSD1 also plays a role in regulating viral gene transcription, e.g., Herpes Simplex Virus (HSV), by demethylating histone H3 lysine9 required for viral gene expression in the host.

With increasing evidence that LSD1 plays a critical role in a diverse set of cancers and diseases, a variety of LSD1 inhibitors, including irreversible LSD1 inhibitors, have been reported and are in clinical development. Irreversible cyclopropyl amine-containing inhibitors, e.g., reviewed in Suzuki and Miyata, ibid, have been shown to be potent inhibitors of the LSD1 enzyme; however, such compounds tend to lack robust cellular potency, have poor metabolic stability and high clearance in vivo.

SUMMARY OF THE INVENTION

The present inventors recognized a need to develop new LSD1 inhibitors that demonstrate improved cellular potency, efficacy, stability and safety. The compounds and compositions of the present invention advantageously overcome one or more of these shortcomings by providing potent, selective and orally active LSD1 inhibitors.

In one aspect of the invention, compounds are provided that irreversibly inhibit LSD1 activity. In certain embodiments, the compounds are represented by formula (I):

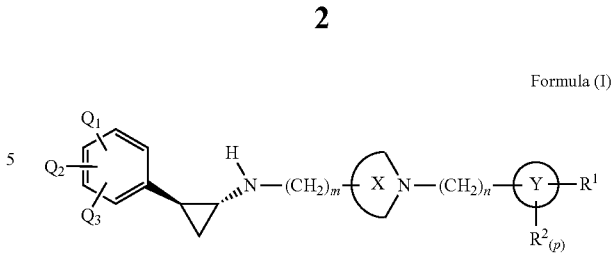

Formula (I)

or a pharmaceutically acceptable salt thereof, wherein X is 4-8 membered, nitrogen-containing, saturated monocyclic or bridged ring system optionally independently substituted with one or more $C_1$-$C_6$ alkyl, alkoxy, halogen or haloalkyl; Y is 5-10 membered aryl or 5-10 membered heteroaryl; $R^1$ is —$C_{1-4}$ alkylene-$R^3$, —$C_{2-4}$ alkenylene-$R^3$, —C(O)NR$^4$R$^5$, or —C(O)NR$^4$SO$_2$R$^6$; each $R^2$ is independently hydrogen, hydroxyl, halogen, cyano, amino, haloalkyl, $C_1$-$C_6$ alkyl, $C_2$-$C_6$ alkenyl, $C_2$-$C_6$ alkynyl, cycloalkyl, heterocyclyl, aryl, heteroaryl, aryloxy, heteroaryloxy, aralkyl, heteroarylalkyl, —C(O)R$^6$, —C(O)NR$^4$R$^5$, —NR$^4$R$^5$, —NR$^4$C(O)R$^6$, or —NR$^4$SO$_2$R$^6$, wherein each of said $C_1$-$C_6$ alkyl, $C_2$-$C_6$ alkenyl, $C_2$-$C_6$ alkynyl, cycloalkyl, heterocyclyl, aryl, heteroaryl, aryloxy, heteroaryloxy, aralkyl, and heteroarylalkyl is optionally independently substituted with one or more $R^6$ or $R^7$; $R^3$ is —C(O)OR$^6$, —C(O)NR$^4$R$^5$, —C(O)NR$^4$OR$^6$, —C(O)NR$^4$SO$_2$R$^6$, aryl, heteroaryl, cycloalkyl, or heterocyclyl, wherein said aryl, heteroaryl, cycloalkyl, and heterocyclyl are each optionally independently substituted with one or more $R^7$; each $R^4$ is independently hydrogen or $C_1$-$C_4$ alkyl; each $R^5$ is independently hydrogen, alkyl, alkoxy, or aralkyloxy, or $R^4$ and $R^5$ together with the nitrogen atom to which they are attached form a 4-8 membered heterocyclyl, wherein said 4-8 membered heterocyclyl is optionally independently substituted with one or more $R^6$ or $R^7$; each $R^6$ is independently hydrogen, $C_1$-$C_6$ alkyl, cycloalkyl, aryl, heteroaryl, arylalkyl or heteroarylalkyl, wherein said $C_1$—$C_6$ alkyl, aryl, heteroaryl, arylalkyl and heteroarylalkyl are each independently optionally independently substituted with one or more $R^7$; each $R^7$ is independently hydrogen, halogen, hydroxy, carboxy, amino, nitro, cyano, azido, haloalkyl, $C_1$-$C_4$-alkoxy, $C_1$-$C_4$-alkylthio, $C_1$-$C_4$-alkylsulfonyl, $C_1$-$C_4$-alkylamino, $C_1$-$C_4$-dialkylamino, acetyl, acetylamino, or methylsulfonylamino; m and n are each independently 0 or 1; p is 0, 1, 2, 3, or 4; and $Q^1$, $Q^2$ and $Q^3$ are each independently hydrogen, halogen, $CF_3$, $C_1$-$C_4$-alkyl, or $C_1$-$C_4$-alkoxy.

In certain embodiments of this aspect, X in the compounds of formula (I) is azetidinyl, pyrrolidinyl, or piperidinyl, wherein each of said azetidinyl, pyrrolidinyl, and piperidinyl is optionally independently substituted with one or more $C_1$-$C_4$ alkyl, alkoxy, halogen or haloalkyl.

In certain some embodiments of this aspect, Y in the compounds of formula (I) is phenyl, indenyl, azulenyl, naphthyl, furanyl, thiophenyl, 2H-pyrrolo, pyrrolo, 2-pyrrolinyl, 3-pyrrolinyl, oxazolyl, thiazolyl, imidazolyl, 2-imidazolinyl, pyrazolyl, 2-pyrazolinyl, isoxazolyl, isothiazolyl, 1,2,3-oxadiazolyl, 1,2,3-triazolyl, 1,3,4-thiadiazolyl, 2H-pyranyl, 4H-pyranyl, pyridyl, pyridazinyl, pyrimidinyl, pyrazinyl, 1,3,5-triazinyl, indolininyl, indolyl, isoindolyl, 3H-indolyl, indolinyl, pyrrolo[2,3-b]pyridinyl, pyrrolo[2,3-c]pyridinyl, pyrrolo[3,2-c]pyridinyl, pyrrolo[3,2-b]pyridinyl, pyrrolo[1,2-b]pyridiazinyl, imidazo[4,5-b]pyridinyl, imidazo[4,5-c]pyridinyl, pyrazolo[4,3-d]pyridinyl, pyrazolo[4,3-c]pyridinyl, pyrazolo[3,4-b]pyridinyl, pyrazolo[3,4-c]pyridinyl, pyrazolo[1,5-a]pyridinyl, imidazo[1,2-a]pyridinyl, imidazo[1,5-a]pyridinyl, imidazo[1,2-c]pyrimidinyl, benzo[b]furanyl, benzo[b]thiophenyl, 1H-indazolyl, benzimidazolyl, benzthioazolyl, benzotriazolyl, purinyl, 4H-quinazolinyl, quinolinyl, isoquinolinyl, cinnolinyl, phthalazinyl, quinazolinyl, quinoxalinyl, 1,6-naphthrydinyl, 1,7-naphthrydinyl, 1,8-naphthrydinyl, 1,5-naphthrydinyl, 2,6-naphthrydinyl, 2,7-naphthrydinyl, pyrido[3,2-d]pyrimidinyl, pyrido[4,3-d]pyrimidinyl, pyrido[3,4-d]pyrimidinyl, pyrido[2,3-d]pyrimidinyl, pyrido[2,3-b]pyrazinyl, pyrido[3,4-b]pyrazinyl, pyrimido[5,4-d]pyrimidinyl, pyrimido[4,5-d]pyrimidinyl, pyrazino[2,3-b]pyrazinyl, pterdinyl or quinuclidinyl.

In some embodiments of this aspect, $R^1$ in the compounds of formula (I) is —C(O)NR$^4$R$^5$, —C(O)NR$^4$SO$_2$R$^6$; —C$_{1-4}$ alkylene-C(O)NR$^4$R$^5$, —C$_{1-4}$ alkylene-C(O)NR$^4$SO$_2$R$^6$, —C$_{2-4}$ alkenylene-C(O)NR$^4$R$^5$; —C$_{2-4}$ alkenylene-C(O)NR$^4$OR$^6$ or —C$_{2-4}$ alkenylene-C(O)NR$^4$SO$_2$R$^6$. In further embodiments, $R^1$ is —CH$_2$CH=CHC(O)NHOC$_1$-C$_4$alkyl, —CH$_2$CH=CHC(O)NHOCH$_2$-aryl, CH$_2$CH=CHC(O)NHSO$_2$C$_1$-C$_4$alkyl, or —CH$_2$CH=CHC(O)NHSO$_2$(CH$_2$)$_p$-aryl, wherein p is zero or one.

In another embodiment of this aspect of the invention, $R^1$ in the compounds of formula (I) is —C(O)NR$^4$SO$_2$R$^6$, wherein $R^6$ is alkyl (such as methyl or ethyl); cycloalkyl (such as cyclopropanyl); or aryl (such as phenyl).

In some embodiments of this aspect of the invention, compounds of formula (I) are provided wherein $R^1$ is —C$_{2-4}$ alkenylene-R$^3$ and $R^3$ is aryl optionally independently substituted with one or more $R^7$. In certain embodiments, the aryl is phenyl optionally independently substituted with one or more $R^7$. Alternatively, $R^3$ is azetidinyl, pyrrolidinyl, pyrazolidinyl, piperidinyl, piperazinyl, tetrahydropyranyl, 1,3-dioxolanyl, 1,4-dioxanyl, morpholinyl, thiomorpholinyl, 1,4-dithianyl, 1,3,5-trithianyl,

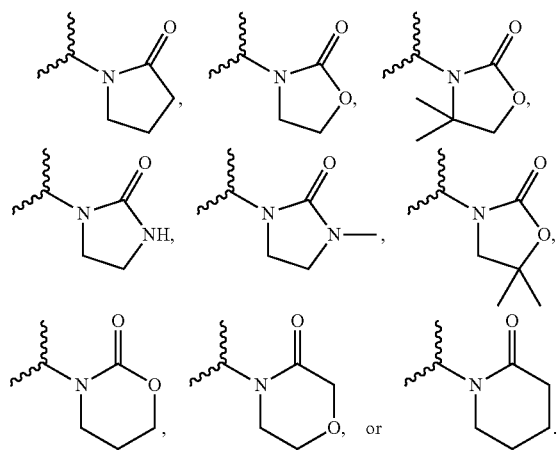

In some embodiments of this aspect of the invention, compounds of formula (I) are provided wherein $R^1$ is —C$_{2-4}$ alkenylene-R$^3$ and $R^3$ is cyclopropanyl, cyclobutanyl, cyclopentyl, cyclohexyl, cycloheptyl, cyclooctyl, norbonanyl or adamantanyl.

In some embodiments of this aspect of the invention, compounds of formula (I) are provided wherein $R^3$ or $R^6$ is substituted with one or more $R^7$, wherein each $R^7$ is independently halogen, hydroxy, carboxy, amino, nitro, cyano, azido, haloalkyl, C$_1$-C$_4$-alkoxy, C$_1$-C$_4$-alkylthio, C$_1$-C$_4$-alkylsulfonyl, C$_1$-C$_4$-alkylamino, C$_1$-C$_4$-dialkylamino, acetyl, acetylamino, or methyl sulfonylamino.

Particular embodiments of compounds of formula (I) include formulae (Ia)-(Ill) (and their pharmaceutically acceptable salts):

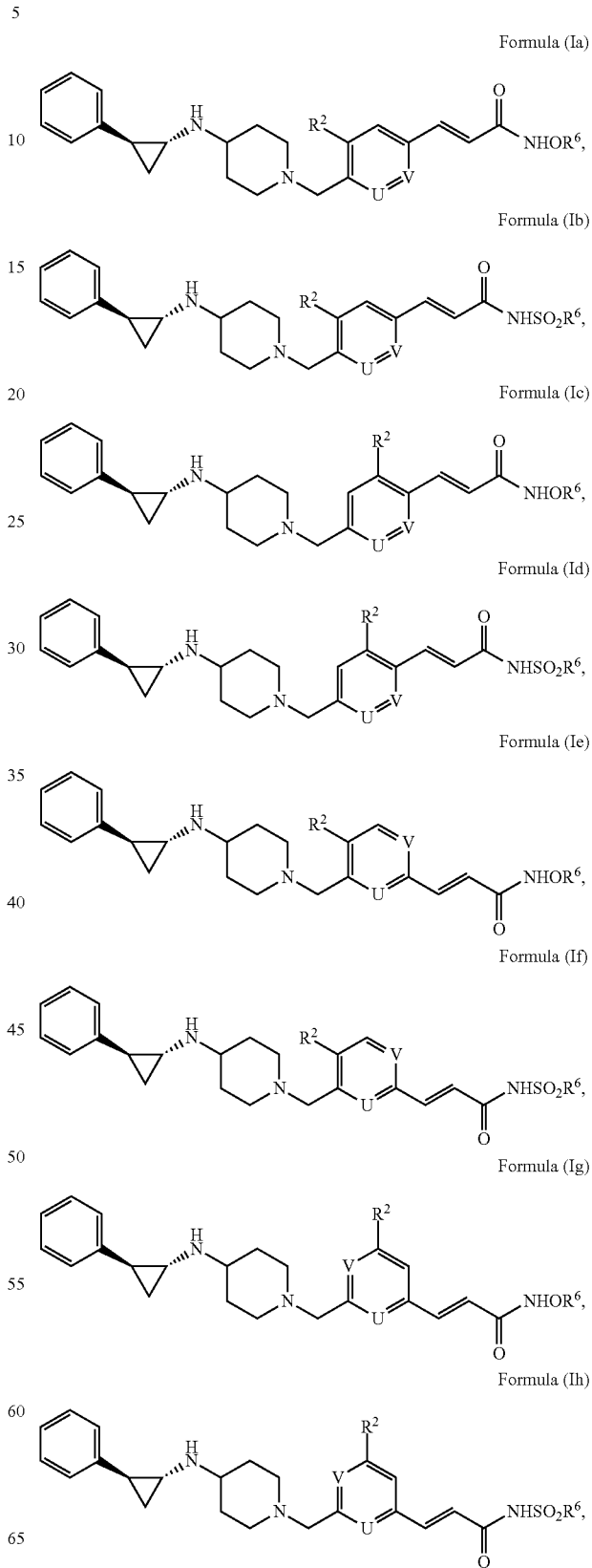

Formula (Ii)
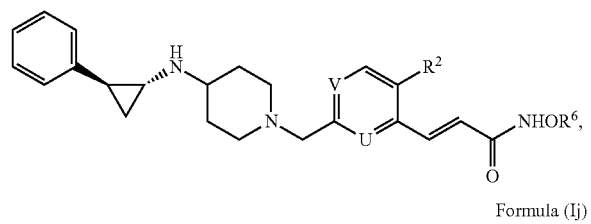
Formula (Ij)
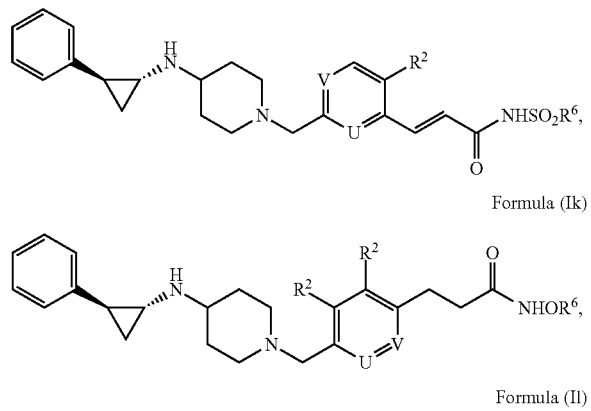
Formula (Ik)
Formula (Il)
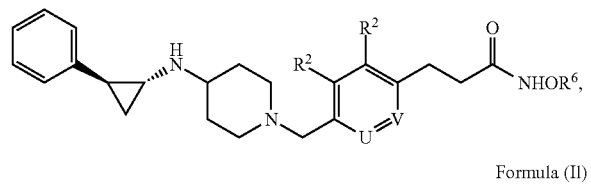
Formula (Im)
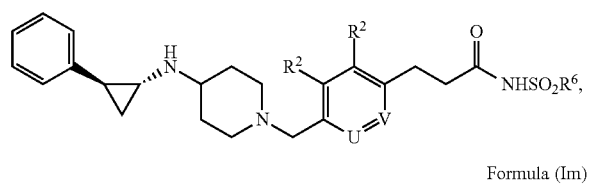
Formula (In)
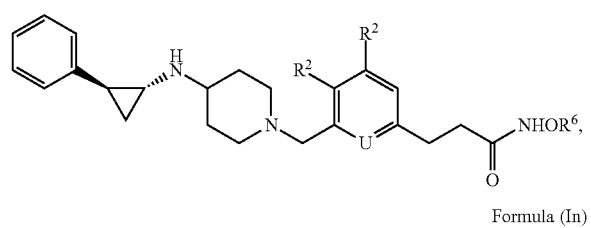
Formula (Io)
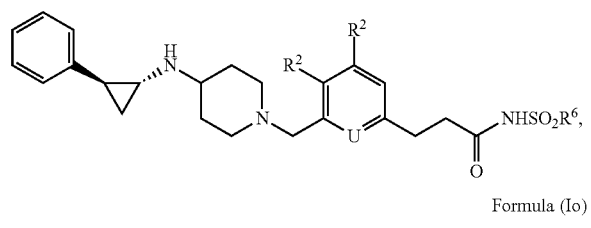
Formula (Ip)
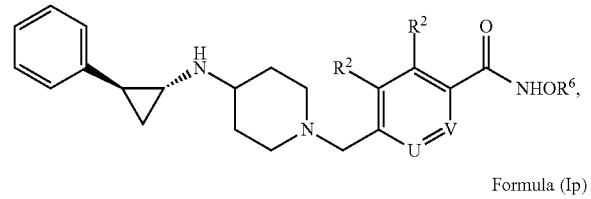
Formula (Iq)
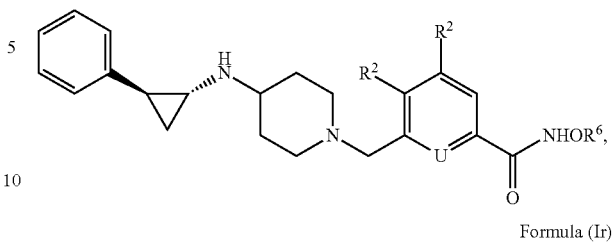
Formula (Ir)
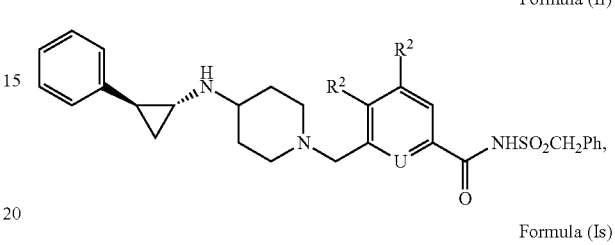
Formula (Is)
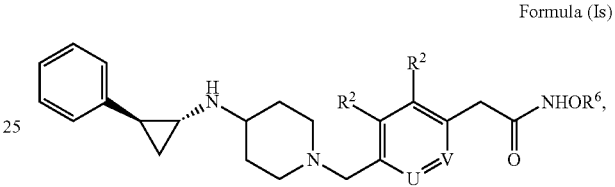
Formula (It)
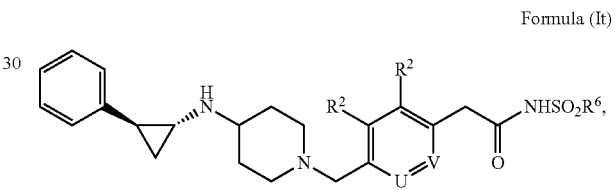
Formula (Iu)
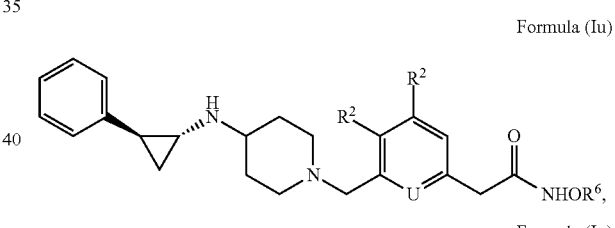
Formula (Iv)
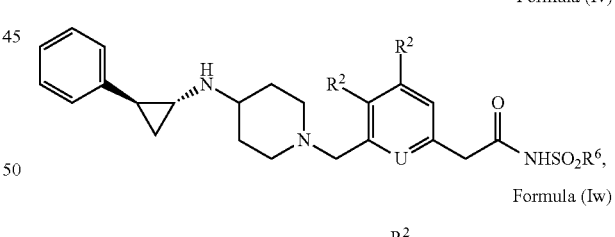
Formula (Iw)
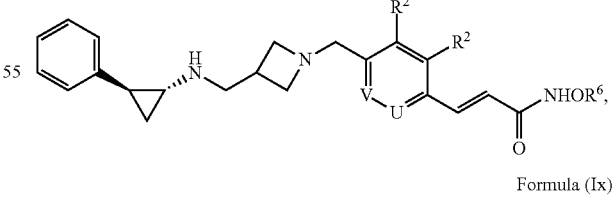
Formula (Ix)
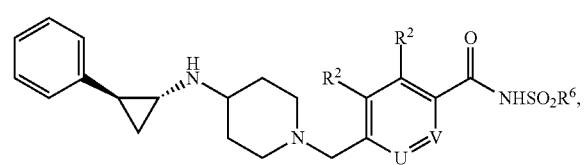
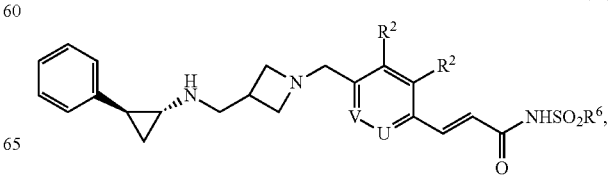

Formula (Iy), Formula (Iz), Formula (Iaa), Formula (Ibb), Formula (Icc), Formula (Idd), Formula (Iee), Formula (Iff), Formula (Igg), Formula (Ihh), Formula (Iii), Formula (Ijj), Formula (Ikk), Formula (Ill)

wherein U and V are each independently —CH— or —N—; and $R^2$ and $R^6$ are defined as in formula (I).

In certain embodiments, each $R^2$ is independently hydrogen, alkyl (such as methyl), or halogen (such as fluoro, chloro or bromo), and $R^6$ is $C_1$-$C_4$ alkyl (such as methyl); aryl (such as phenyl); or aralkyl (such as benzyl).

In another aspect of the invention, pharmaceutical compositions are provided comprising a therapeutically effective amount of a compound of the present invention and a pharmaceutically acceptable excipient.

In yet another aspect, the invention provides methods for inhibiting LSD1 activity in a cell comprising contacting the cell or causing the cell to be contacted with a compound of the invention. Also provided are methods for treating LSD1-mediated diseases (e.g., cancer) in a patient are provided comprising administering a therapeutically effective amount of a compound or pharmaceutical composition of the present invention to a patient in need thereof.

DETAILED DESCRIPTION OF THE INVENTION

The present invention relates to LSD1 inhibitors. In particular, the present invention relates to compounds that irreversibly inhibit the activity of LSD1, pharmaceutical compositions comprising a therapeutically effective amount of the compounds, and methods of use therefor.

Definitions

Unless defined otherwise, all technical and scientific terms used herein have the same meaning as is commonly understood by one of skill in the art to which this invention belongs. All patents, patent applications, and publications referred to herein are incorporated by reference to the extent they are consistent with the present disclosure. Terms and ranges have their generally defined definition unless expressly defined otherwise.

For simplicity, chemical moieties are defined and referred to throughout primarily as univalent chemical moieties (e.g., alkyl, aryl, etc.). Nevertheless, such terms may also be used to convey corresponding multivalent moieties under the appropriate structural circumstances clear to those skilled in the art. For example, while an "alkyl" moiety generally refers to a monovalent radical (e.g. $CH_3$—$CH_2$—), in certain circumstances a bivalent linking moiety can be "alkyl," in which case those skilled in the art will understand the alkyl to be a divalent radical (e.g., —$CH_2$—$CH_2$—), which is equivalent to the term "alkylene." (Similarly, in circumstances in which a divalent moiety is required and is stated as being "aryl," those skilled in the art will understand that the term "aryl" refers to the corresponding divalent moiety, arylene.) All atoms are understood to have their normal number of valences for bond formation (i.e., 4 for carbon, 3 for N, 2 for O, and 2, 4, or 6 for S, depending on the oxidation state of the S).

As used herein, "LSD1" refers to a mammalian lysine-specific demethylase enzyme ("LSD1"), which removes methyl groups from mono- and dimethylated lysine4 and lysine9 of the histone H3 protein.

As used herein, an "LSD1 inhibitor" refers to compounds of the present invention that are represented by formulae (I) or (II) as described herein. These compounds are capable of negatively modulating or inhibiting all or a portion of the enzymatic activity of LSD1. The LSD1 inhibitors of the present invention irreversibly inhibit LSD1 activity by forming a covalent adduct with the flavin ring of FAD in the active site of LSD1 following one electron oxidation and cyclopropyl ring opening.

The term "amino" refers to —$NH_2$.

The term "alkyl" as employed herein refers to straight and branched chain aliphatic groups having from 1 to 12 carbon atoms. As such, "alkyl" encompasses $C_1$, $C_2$, $C_3$, $C_4$, $C_5$, $C_6$, $C_7$, $C_8$, $C_9$, $C_{10}$, $C_{11}$ and $C_{12}$ groups. Examples of alkyl groups include, without limitation, methyl, ethyl, propyl, isopropyl, butyl, isobutyl, sec-butyl, tert-butyl, pentyl, and hexyl.

The term "alkenyl" as used herein means an unsaturated straight or branched chain aliphatic group with one or more carbon-carbon double bonds, having from 2 to 12 carbon atoms. As such, "alkenyl" encompasses $C_2$, $C_3$, $C_4$, $C_5$, $C_6$, $C_7$, $C_8$, $C_9$, $C_{10}$, $C_{11}$ and $C_{12}$ groups. Examples of alkenyl groups include, without limitation, ethenyl, propenyl, butenyl, pentenyl, and hexenyl.

The term "alkynyl" as used herein means an unsaturated straight or branched chain aliphatic group with one or more carbon-carbon triple bonds, having from 2 to 12 carbon atoms. As such, "alkynyl" encompasses $C_2$, $C_3$, $C_4$, $C_5$, $C_6$, $C_7$, $C_8$, $C_9$, $C_{10}$, $C_{11}$ and $C_{12}$ groups. Examples alkynyl groups include, without limitation, ethynyl, propynyl, butynyl, pentynyl, and hexynyl.

An "alkylene," "alkenylene," or "alkynylene" group is an alkyl, alkenyl, or alkynyl group, as defined hereinabove, that is positioned between and serves to connect two other chemical groups. Examples of alkylene groups include, without limitation, methylene, ethylene, propylene, and butylene. Exemplary alkenylene groups include, without limitation, ethenylene, propenylene, and butenylene. Exemplary alkynylene groups include, without limitation, ethynylene, propynylene, and butynylene.

The term "alkoxy" refers to —$OC_1$-$C_6$alkyl.

The term "alkylthio" refers to —$SC_1$-$C_6$alkyl.

The term "alkylamino" refers to —$NR^4C_1$-$C_6$alkyl.

The term "alkylsulfonyl" refers to —$SO_2C_1$-$C_6$alkyl.

The term "cycloalkyl" as employed herein includes saturated and partially unsaturated cyclic hydrocarbon groups having 3 to 12 carbons. As such, "cycloalkyl" includes $C_3$, $C_4$, $C_5$, $C_6$, $C_7$, $C_8$, $C_9$, $C_{10}$, $C_{11}$ and $C_{12}$ cyclic hydrocarbon groups. Representative cycloalkyl groups include, without limitation, cyclopropyl, cyclobutyl, cyclopentyl, cyclopentenyl, cyclohexyl, cyclohexenyl, cycloheptyl, and cyclooctyl.

The term "heteroalkyl" refers to an alkyl group, as defined hereinabove, wherein one or more carbon atoms in the chain are replaced by a heteroatom selected from the group consisting of O, S, and $NR^4$.

An "aryl" group is a $C_6$-$C_{14}$ aromatic moiety comprising one to three aromatic rings, which is optionally substituted. As such, "aryl" includes $C_6$, $C_7$, $C_8$, $C_9$, $C_{10}$, $C_{11}$, $C_{12}$ $C_{13}$, and $C_{14}$ cyclic hydrocarbon groups. An exemplary aryl group is a $C_6$-$C_{10}$ aryl group. Particular aryl groups include, without limitation, phenyl, naphthyl, anthracenyl, and fluorenyl.

An "aralkyl" or "arylalkyl" group comprises an aryl group covalently linked to an alkyl group, either of which may independently be optionally substituted or unsubstituted. An example of an aralkyl group is —$(C_1$-$C_6)$alkyl$(C_6$-$C_{10})$aryl, including, without limitation, benzyl, phenethyl, and naphthylmethyl.

The term "aryloxy" refers to —O-aryl.

A "heterocyclyl" or "heterocyclic" group is a ring structure having from 3 to 12 atoms, (3, 4, 5, 6, 7, 8, 9, 10, 11 or 12 atoms), for example 4 to 8 atoms, wherein one or more ring atoms are selected from the group consisting of $NR^4$, O, and S, and the remainder of the ring atoms are quaternary or carbonyl carbons. The ring carbons of the heterocyclic group are optionally independently substituted with $R^7$ (as defined above). The heterocyclic group is also independently optionally substituted on nitrogen with alkyl, aryl, aralkyl, alkylcarbonyl, alkylsulfonyl, arylcarbonyl, arylsulfonyl, alkoxycarbonyl, or aralkoxycarbonyl, and on sulfur with oxo or lower alkyl. Examples of heterocyclic groups include, without limitation, epoxy, azetidinyl, aziridinyl, tetrahydrofuranyl, tetrahydropyranyl, pyrrolidinyl, piperidinyl, piperazinyl, imidazolidinyl, thiazolidinyl, dithianyl, trithianyl, dioxolanyl, oxazolidinyl, oxazolidinonyl, decahydroquinolinyl, piperidonyl, 4-piperidonyl, thiomorpholinyl, and morpholinyl. Specifically excluded from the scope of this term are compounds having adjacent ring O and/or S atoms.

The term "heterocyclylalkyl" refers to a heterocyclyl group as defined herein linked to the remaining portion of the molecule via an alkyl linker.

As used herein, the term "heteroaryl" refers to a group having 5 to 14 ring atoms, 5, 6, 7, 8, 9, 10, 11, 12, 13 or 14 ring atoms; having 6, 10, or 14 it electrons shared in a cyclic array; and having, in addition to carbon atoms, from one to three heteroatoms that are each independently N, O, or S. "Heteroaryl" also includes fused multicyclic (e.g., bicyclic) ring systems in which one or more of the fused rings is non-aromatic, provided that at least one ring is aromatic and at least one ring contains an N, O, or S ring atom. Examples of such multicyclic heteroaryl ring systems include 2H-benzo[b][1,4]oxazin-3(4H)-one and 2H-pyrido[3,2-b][1,4]oxazin-3(4H)-one.

Examples of heteroaryl groups include acridinyl, azocinyl, benzimidazolyl, benzofuranyl, benzothiofuranyl, benzothiophenyl, benzoxazolyl, benzthiazolyl, benztriazolyl, benztetrazolyl, benzisoxazolyl, benzisothiazolyl, benzimidazolinyl, carbazolyl, 4aH-carbazolyl, carbolinyl, chromanyl, chromenyl, cinnolinyl, furanyl, furazanyl, imidazolinyl, imidazolyl, 1H-indazolyl, indolenyl, indolinyl, indolizinyl, indolyl, 3H-indolyl, isobenzofuranyl, isochromanyl, isoindazolyl, isoindolinyl, isoindolyl, isoquinolinyl, isothiazolyl, isoxazolyl, naphthyridinyl, octahydroisoquinolinyl, oxadiazolyl, 1,2,3-oxadiazolyl, 1,2,4-oxadiazolyl, 1,2,5-oxadiazolyl, 1,3,4-oxadiazolyl, oxazolidinyl, oxazolyl, oxazolidinyl, pyrimidinyl, phenanthridinyl, phenanthrolinyl, phenazinyl, phenothiazinyl, phenoxathiinyl, phenoxazinyl, phthalazinyl, piperonyl, pteridinyl, purinyl, pyranyl, pyrazinyl, pyrazolidinyl, pyrazolinyl, pyrazolyl, pyridazinyl, pyridooxazole, pyridoimidazole, pyridothiazole, pyridinyl, pyridyl, pyrimidinyl, pyrrolinyl, 2H-pyrrolyl, pyrrolyl, quinazolinyl, quinolinyl, 4H-quinolizinyl, quinoxalinyl, quinuclidinyl, tetrahydroisoquinolinyl, tetrahydroquinolinyl, tetrazolyl, 6H-1,2,5-thiadiazinyl, 1,2,3-thiadiazolyl, 1,2,4-thiadiazolyl, 1,2,5-thiadiazolyl, 1,3,4-thiadiazolyl, thianthrenyl, thiazolyl, thienyl, thienothiazolyl, thienooxazolyl, thienoimidazolyl, thiophenyl, triazinyl, 1,2,3-triazolyl, 1,2,4-triazolyl, 1,2,5-triazolyl, 1,3,4-triazolyl, and xanthenyl.

The term "heteroaryloxy" refers to —O-heteroaryl.

An "arylene," "heteroarylene," or "heterocyclylene" group is an bivalent aryl, heteroaryl, or heterocyclyl group, as defined hereinabove, that is positioned between and serves to connect two other chemical groups.

When a hydrocarbon (e.g., an alkyl or aryl) is described as having a certain range of numbers of carbon atoms (e.g., $C_1$-$C_6$ alkyl), it will be understood that it encompasses hydrocarbons with each number of carbons within that range. So, for example, "$C_1$-$C_6$ alkyl" represents the group "$C_1$ alkyl, $C_2$ alkyl, $C_3$ alkyl, $C_4$ alkyl, $C_5$ alkyl, and $C_6$ alkyl."

As employed herein, when a moiety (e.g., cycloalkyl, hydrocarbyl, aryl, heteroaryl, heterocyclic, urea, etc.) is described as "optionally substituted" without expressly stating the substitutuents it is meant that the group optionally has from one to four, preferably from one to three, more preferably one or two, non-hydrogen substituents. Suitable substituents include, without limitation, halo, hydroxy, oxo (e.g., a ring —CH— substituted with oxo is —C(O)—) nitro, halohydrocarbyl, hydrocarbyl, aryl, aralkyl, alkoxy, aryloxy, amino, acylamino, alkylcarbamoyl, arylcarbamoyl, aminoalkyl, acyl, carboxy, hydroxyalkyl, alkanesulfonyl, arenesulfonyl, alkanesulfonamido, arenesulfonamido, aralkylsulfonamido, alkylcarbonyl, acyloxy, cyano, and ureido groups. Exemplary substituents, which are themselves not further substituted (unless expressly stated otherwise) are:

(a) for $Q^1$, $Q^2$ and $Q^3$: hydrogen, halogen, including F, Cl or Br; halohydrocarbyl, such as $CF_3$, alkyl, for example $C_1$-$C_4$-alkyl, or alkoxy, such as $C_1$-$C_4$-alkoxy; and (b) for X: alkyl (e.g., $C_1$-$C_4$-alkyl), halogen (e.g., F, Cl or Br), alkoxy, (e.g., $C_1$-$C_4$-alkoxy), and haloalkyl, (e.g., trifluoromethyl).

The term "halogen" or "halo" as employed herein refers to chlorine, bromine, fluorine, or iodine.

The term "haloalkyl" refers to an alkyl chain in which one or more hydrogens have been replaced by a halogen. Exemplary haloalkyls are trifluoromethyl, difluoromethyl, flurochloromethyl, and fluoromethyl.

As herein employed, the term "acyl" refers to an alkylcarbonyl or arylcarbonyl substituent. The term "acylamino" refers to an amide group attached at the nitrogen atom (i.e., R—CO—NH—). The term "carbamoyl" refers to an amide group attached at the carbonyl carbon atom (i.e., $NH_2$—CO—). The nitrogen atom of an acylamino or carbamoyl substituent is additionally substituted. The term "sulfonamido" refers to a sulfonamide substituent attached by either the sulfur or the nitrogen atom. The term "ureido" as employed herein refers to a substituted or unsubstituted urea moiety.

The term "radical" as used herein means a chemical moiety comprising one or more unpaired electrons.

As used herein, "an effective amount" of a compound is an amount that is sufficient to negatively modulate or inhibit the activity of LSD1.

As used herein, "a therapeutically effective amount" of a compound is an amount that is sufficient to ameliorate, or in some manner reduce a symptom or stop or reverse progression of a condition, or negatively modulate or inhibit the activity of LSD1. Such amount may be administered as a single dosage or may be administered according to a regimen, whereby it is effective.

As used herein, treatment means any manner in which the symptoms or pathology of a condition, disorder or disease are ameliorated or otherwise beneficially altered. Treatment also encompasses any pharmaceutical use of the compositions herein.

As used herein, amelioration of the symptoms of a particular disorder by administration of a particular pharmaceutical composition refers to any lessening, whether permanent or temporary, lasting or transient that can be attributed to or associated with administration of the composition.

Compounds

In one aspect of the invention, compounds are provided represented by formula (I):

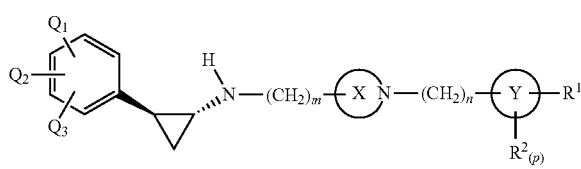

Formula (I)

or a pharmaceutically acceptable salt thereof:

wherein X is 4-8 membered saturated monocyclic or bridged nitrogen-containing ring system optionally independently substituted with one or more $C_1$-$C_6$ alkyl, alkoxy, halogen or haloalkyl;

Y is 5-10 membered aryl or 5-10 membered heteroaryl;

$R^1$ is —$C_{1-4}$ alkylene-$R^3$, —$C_{2-4}$ alkenylene-$R^3$, —C(O)NR$^4$R$^5$, or —C(O)NR$^4$SO$_2$R$^6$;

each $R^2$ is hydrogen, hydroxyl, halogen, cyano, amino, haloalkyl, $C_1$-$C_6$ alkyl, $C_2$-$C_6$ alkenyl, $C_2$-$C_6$ alkynyl, cycloalkyl, heterocyclyl, aryl, heteroaryl, aryloxy, heteroaryloxy, aralkyl, heteroarylalkyl, —C(O)R$^6$, —C(O)NR$^4$R$^5$, —NR$^4$R$^5$, —NR$^4$C(O)R$^6$, or —NR$^4$SO$_2$R$^6$, wherein each of said $C_1$-$C_6$ alkyl, $C_2$-$C_6$ alkenyl, $C_2$-$C_6$ alkynyl, cycloalkyl, heterocyclyl, aryl, heteroaryl, aryloxy, heteroaryloxy, aralkyl, heteroarylalkyl is optionally independently substituted with one or more $R^6$ or $R^7$;

each $R^3$ is independently —C(O)OR$^6$, —C(O)NR$^4$R$^5$, —C(O)NR$^4$OR$^6$, —C(O)NR$^4$SO$_2$R$^6$, aryl, heteroaryl, cycloalkyl, and heterocyclyl, wherein said aryl, heteroaryl, cycloalkyl, and heterocyclyl are each optionally substituted with one or more $R^7$;

each $R^4$ is independently hydrogen or $C_{1-4}$ alkyl;

each $R^5$ is independently hydrogen, $C_1$-$C_6$ alkyl, alkoxy, aryloxy, or aralkyloxy, wherein said aryloxy and aralkyloxy is optionally independently substituted on the aryl group with one or more $R^7$;

or $R^4$ and $R^5$ together with the nitrogen atom to which they are attached form a 4-8 membered heterocyclyl, wherein said 4-8 membered heterocyclyl is optionally independently substituted with one or more $R^6$ or $R^7$;

each $R^6$ is hydrogen, $C_1$-$C_6$ alkyl, cycloalkyl, aryl, heteroaryl, arylalkyl or heteroarylalkyl, wherein said $C_1$-$C_6$ alkyl, aryl, heteroaryl, arylalkyl or heteroarylalkyl may each be optionally independently substituted with one or more $R^7$;

each $R^7$ hydrogen, halogen, hydroxy, carboxy, amino, nitro, cyano, azido, haloalkyl, $C_1$-$C_4$-alkoxy, $C_1$-$C_4$-alkylthio, $C_1$-$C_4$-alkylsulfonyl, $C_1$-$C_4$-alkylamino, $C_1$-$C_4$-dialkylamino, acetyl, acetylamino, or methylsulfonylamino;

m is 0 or 1;
n is 0 or 1;
p is 0, 1, 2, 3 or 4; and
$Q^1$, $Q^2$ and $Q^3$ are each independently hydrogen, halogen, CF$_3$, $C_1$-$C_4$-alkyl, or $C_1$-$C_4$-alkoxy.

In certain embodiments, X is azetidinyl, pyrrolidinyl, or piperidinyl, each of which is optionally independently substituted with one or more $C_1$-$C_6$alkyl, alkoxy, halogen or haloalkyl. In certain embodiments, X is azetidinyl or piperdinyl.

In some embodiments, Y is phenyl, indenyl, azulenyl, naphthyl, furanyl, thiophenyl, 2H-pyrrolo, pyrrolo, 2-pyrrolinyl, 3-pyrrolinyl, oxazolyl, thiazolyl, imidazolyl, 2-imidazolinyl, pyrazolyl, 2-pyrazolinyl, isoxazolyl, isothiazolyl, 1,2,3-oxadiazolyl, 1,2,3-triazolyl, 1,3,4-thiadiazolyl, 2H-pyranyl, 4H-pyranyl, pyridyl, pyridazinyl, pyrimidinyl, pyrazinyl, 1,3,5-triazinyl, indolininyl, indolyl, isoindolyl, 3H-indolyl, indolinyl, pyrrolo[2,3-b]pyridinyl, pyrrolo[2,3-c]pyridinyl, pyrrolo[3,2-c]pyridinyl, pyrrolo[3,2-b]pyridinyl, pyrrolo[1,2-b]pyridiazinyl, imidazo[4,5-b]pyridinyl, imidazo[4,5-c]pyridinyl, pyrazolo[4,3-d]pyridinyl, pyrazolo[4,3-c]pyridinyl, pyrazolo[3,4-b]pyridinyl, pyrazolo[3,4-c]pyridinyl, pyrazolo[1,5-a]pyridinyl, imidazo[1,2-a]pyridinyl, imidazo[1,5-a]pyridinyl, imidazo[1,2-c]pyrimidinyl, benzo[b]furanyl, benzo[b]thiophenyl, 1H-indazolyl, benzimidazolyl, benzthioazolyl, benzotriazolyl, purinyl, 4H-quinazolinyl, quinolinyl, isoquinolinyl, cinnolinyl, phthalazinyl, quinazolinyl, quinoxalinyl, 1,6-naphthrydinyl, 1,7-naphthrydinyl, 1,8-naphthrydinyl, 1,5-naphthrydinyl, 2,6-naphthrydinyl, 2,7-naphthrydinyl, pyrido[3,2-d]pyrimidinyl, pyrido[4,3-d]pyrimidinyl, pyrido[3,4-d]pyrimidinyl, pyrido[2,3-d]pyrimidinyl, pyrido[2,3-b]pyrazinyl, pyrido[3,4-b]pyrazinyl, pyrimido[5,4-d]pyrimidinyl, pyrimido[4,5-d]pyrimidinyl, pyrazino[2,3-b]pyrazinyl, pterdinyl or quinuclidinyl. In some embodiments, Y is phenyl.

In some embodiments of this aspect of the invention, $R^1$ is —C(O)NR$^4$R$^5$, —C(O)NR$^4$SO$_2$R$^6$; —$C_{1-4}$ alkylene-C(O)NR$^4$R$^5$, —$C_{1-4}$ alkylene-C(O)NR$^4$SO$_2$R$^6$, —$C_{2-4}$ alkenylene-C(O)NR$^4$R$^5$; —$C_{2-4}$ alkenylene-C(O)NR$^4$OR$^6$ or —$C_{2-4}$ alkenylene-C(O)NR$^4$SO$_2$R$^6$. In certain embodiments, $R^1$ is —CH$_2$CH=CHC(O)NHOC$_{1-4}$ alkyl, —CH$_2$CH=CHC(O)NHOCH$_2$-aryl, CH$_2$CH=CHC(O)NHSO$_2$C$_{1-4}$alkyl or —CH$_2$CH=CHC(O)NHSO$_2$(CH$_2$)$_q$-aryl, wherein q is zero or one.

In some embodiments of this aspect of the invention, $R^1$ is —$C_{2-4}$ alkenylene-$R^3$, and $R^3$ is heterocyclyl. In certain exemplary embodiments, the heterocyclyl is azetidinyl, pyrrolidinyl, pyrazolidinyl, piperidinyl, piperazinyl, tetrahydropyranyl, 1,3-dioxolanyl, 1,4-dioxanyl, morpholinyl, thiomorpholinyl, 1,4-dithianyl, or 1,3,5-trithianyl. In other exemplary embodiments, the heterocyclyl is:

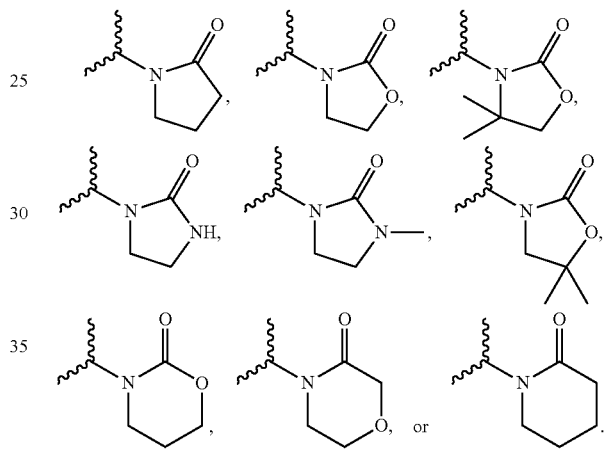

In some embodiments, $R^1$ is —$C_{2-4}$ alkenylene-$R^3$, and $R^3$ is a cycloalkyl. In certain exemplary embodiments, the cycloalkyl is cyclopropanyl, cyclobutanyl, cyclopentyl, cyclohexyl, cycloheptyl, cyclooctyl, norbonanyl or adamantanyl.

In some embodiments, $R^1$ is —$C_{2-4}$ alkenylene-$R^3$, and $R^3$ is optionally independently substituted with one or more $R^7$. $R^7$ substitutions include halogen, hydroxy, carboxy, amino, nitro, cyano, azido, haloalkyl, $C_1$-$C_4$-alkoxy, $C_1$-$C_4$-alkylthio, $C_1$-$C_4$-alkylsulfonyl, $C_1$-$C_4$-alkylamino, $C_1$-$C_4$-dialkylamino, acetyl, acetylamino, and methylsulfonylamino.

In another aspect of the invention, $R^1$ is —C(O)NR$^4$SO$_2$R$^6$, wherein $R^6$ is alkyl, such as methyl or ethyl; cycloalkyl, such as cyclopropanyl; or aryl, such as phenyl.

In certain aspects, the compounds of formula (I) are represented by formula (Ia)-(Il) (and their pharmaceutically acceptable salts):

Formula (Ia)

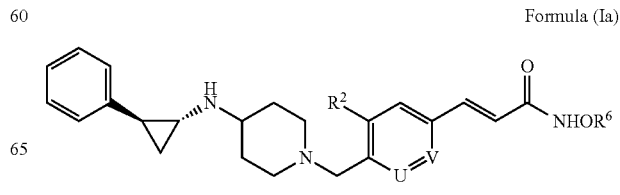

Formula (Ib)
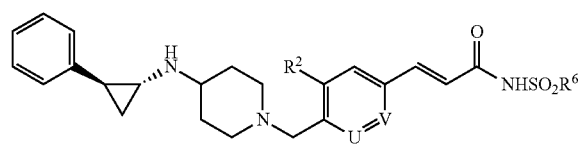
Formula (Ic)
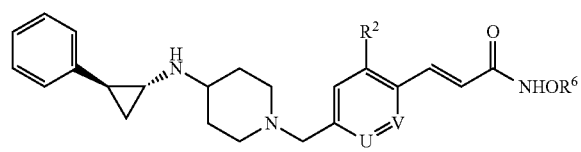
Formula (Id)
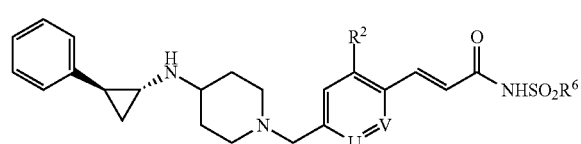
Formula (Ie)
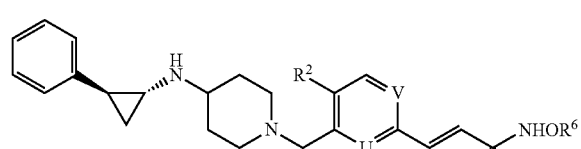
Formula (If)
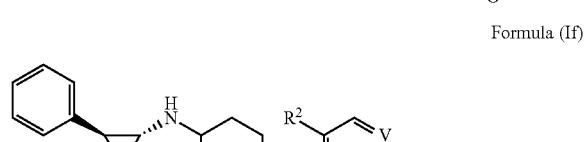
Formula (Ig)
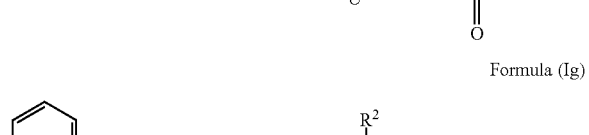
Formula (Ih)
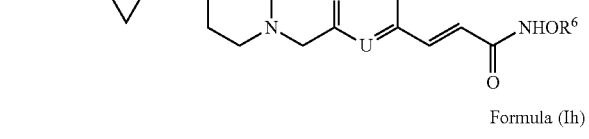
Formula (Ii)
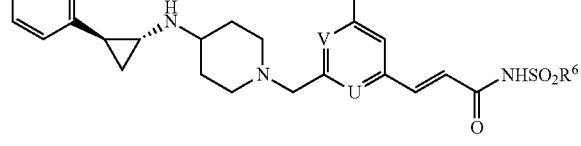
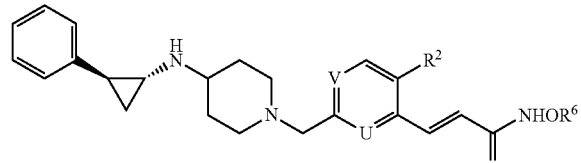
Formula (Ij)
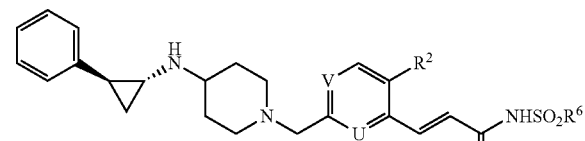
Formula (Ik)
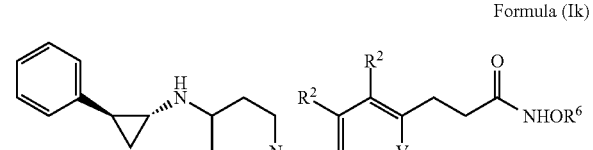
Formula (Il)
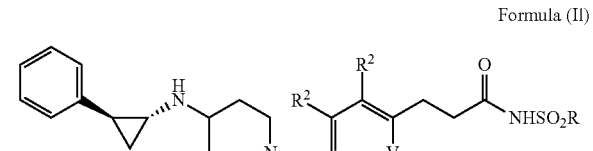
Formula (Im)
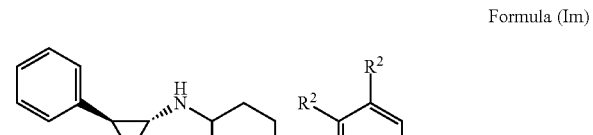
Formula (In)
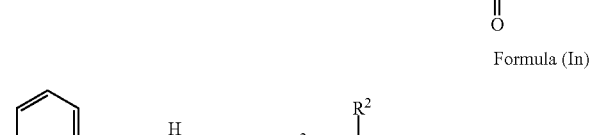
Formula (Io)
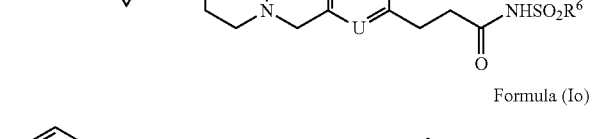
Formula (Ip)
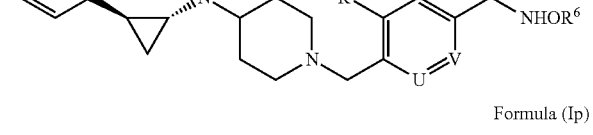
Formula (Iq)
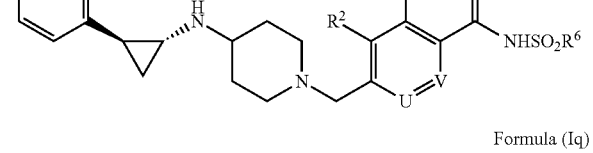
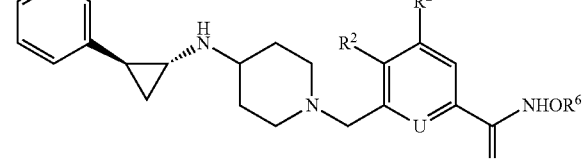

-continued
Formula (Ir)
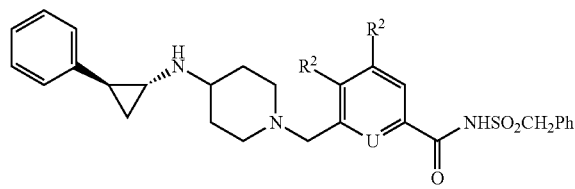
Formula (Is)
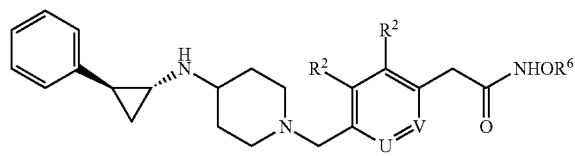
Formula (It)
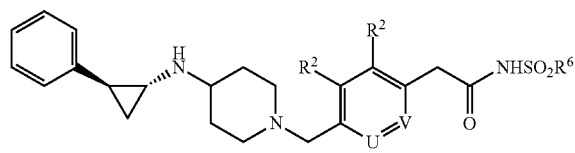
Formula (Iu)
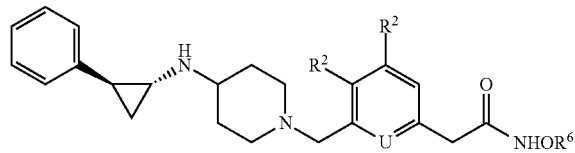
Formula (Iv)
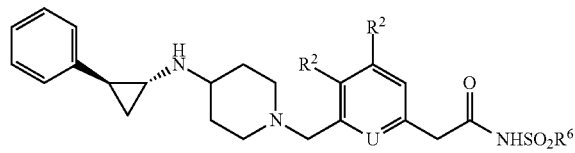
Formula (Iw)
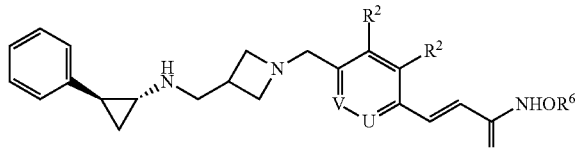
Formula (Ix)
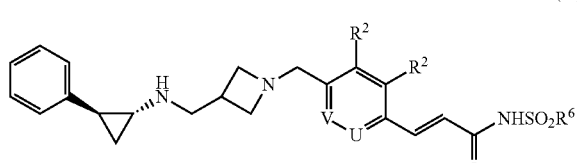
Formula (Iy)
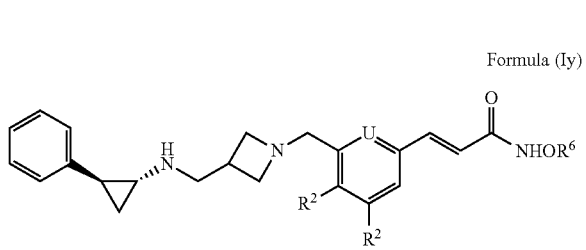
-continued
Formula (Iz)
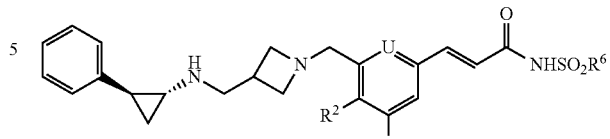
Formula (Iaa)
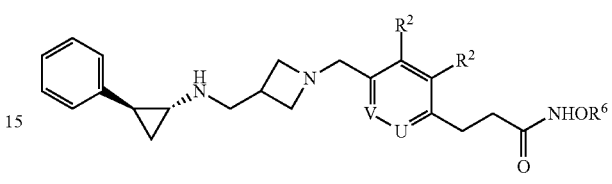
Formula (Ibb)
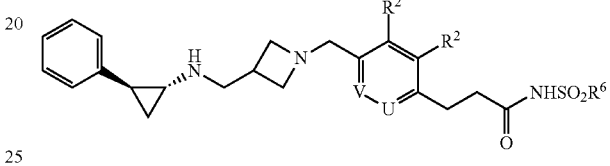
Formula (Icc)
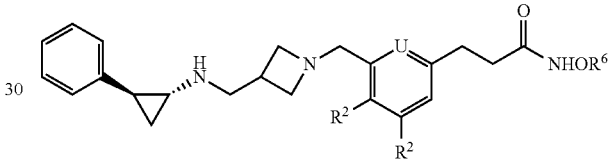
Formula (Idd)
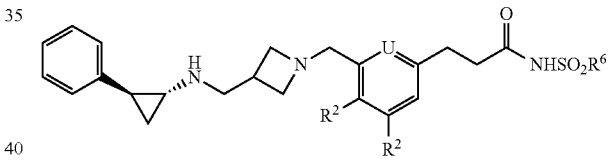
Formula (Iee)
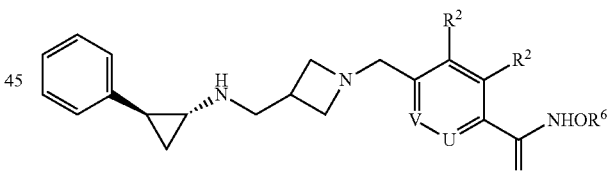
Formula (Iff)
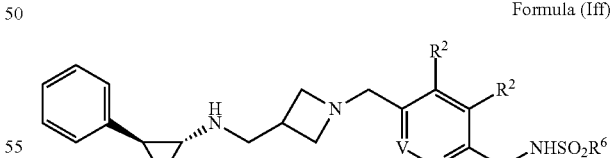
Formula (Igg)
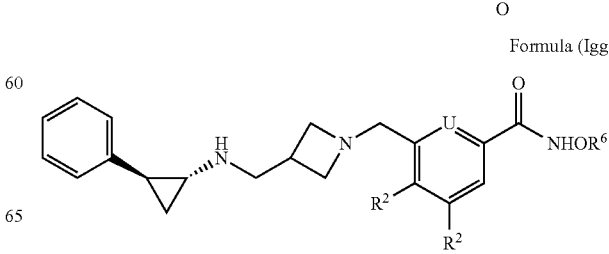

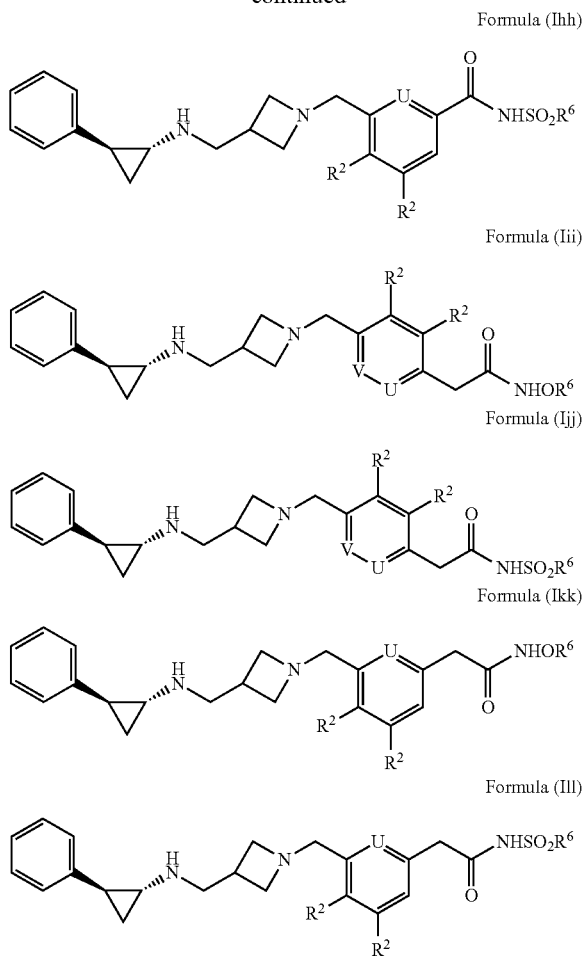

wherein U and V are each independently —CH— or —N— and $R^2$ and $R^6$ are defined as in formula (I). In certain embodiments, each $R^2$ is independently hydrogen, alkyl, such as methyl, or halogen, such as fluoro, chloro or bromo, and $R^6$ is $C_1$-$C_4$ alkyl, such as methyl; cycloalkyl, such as cyclopropanyl, aryl, such as phenyl; or aralkyl, such as benzyl.

In certain embodiments, exemplary compounds of formula (I) are
(E)-N-Methoxy-3-(4-((4-(((trans)-2-phenylcyclopropyl) amino)piperidin-1-yl)methyl)phenyl)acrylamide;
(E)-N-(Methylsulfonyl)-3-(4-((4-(((trans)-2-phenylcyclopropyl)amino)piperidin-1-yl)methyl)phenyl)acrylamide;
(E)-N-Methoxy-3-(3-((4-(((trans)-2-phenylcyclopropyl) amino)piperidin-1-yl)methyl)phenyl)acrylamide;
(E)-N-(Methylsulfonyl)-3-(3-((4-(((trans)-2-phenylcyclopropyl)amino)piperidin-1-yl)methyl)phenyl)acrylamide;
(E)-N-Phenoxy-3-(4-((4-(((trans)-2-phenylcyclopropyl) amino)piperidin-1-yl)methyl)phenyl)acrylamide;
(E)-N-(Benzyloxy)-3-(4-((4-(((trans)-2-phenylcyclopropyl) amino)piperidin-1-yl)methyl)phenyl)acrylamide;
(E)-3-(4-((4-(((trans)-2-Phenylcyclopropyl)amino)piperidin-1-yl)methyl)phenyl)-N-(phenyl sulfonyl)acrylamide;
(E)-N-(Benzylsulfonyl)-3-(4-((4-(((trans)-2-phenylcyclopropyl)amino)piperidin-1-yl)methyl)phenyl)acrylamide;
(E)-N-(Benzyloxy)-3-(3-((4-(((trans)-2-phenylcyclopropyl) amino)piperidin-1-yl)methyl)phenyl)acrylamide;
(E)-3-(3-((4-(((trans)-2-Phenylcyclopropyl)amino)piperidin-1-yl)methyl)phenyl)-N-(phenyl sulfonyl)acrylamide;
(E)-N-(Benzylsulfonyl)-3-(3-((4-(((trans)-2-phenylcyclopropyl)amino)piperidin-1-yl)methyl)phenyl)acrylamide;
N-trans-2-phenylcyclopropyl)-1-(4-((E)-styryl)benzyl)piperidin-4-amine;
N-(trans-2-phenylcyclopropyl)-1-(3-((E)-styryl)benzyl)piperidin-4-amine;
1-(3-((E)-2-(1H-tetrazol-5-yl)vinyl)benzyl)-N-trans-2-phenylcyclopropyl)piperidin-4-amine;
(E)-N-(Methylsulfonyl)-3-(4-((4-(((1R,2S)-2-phenylcyclopropyl)amino)piperidin-1-yl)methyl)phenyl)acrylamide;
(E)-N-Methyl-N-(methyl sulfonyl)-3-(4-((4-(((1R,2S)-2-phenylcyclopropyl)amino)piperidin-1-yl)methyl)phenyl) acrylamide;
(E)-N-(Isopropyl sulfonyl)-3-(4-((4-(((1R,2S)-2-phenylcyclopropyl)amino)piperidin-1-yl)methyl)phenyl)acrylamide;
(E)-3-(4-((4-(((1R,2S)-2-Phenylcyclopropyl)amino)piperidin-1-yl)methyl)phenyl)-N-(propyl sulfonyl)acrylamide;
(E)-N-(Ethylsulfonyl)-3-(4-((4-(((1R,2S)-2-phenylcyclopropyl)amino)piperidin-1-yl)methyl)phenyl)acrylamide;
(E)-N-(Ethylsulfonyl)-3-(4-((4-(((trans)-2-phenylcyclopropyl)amino)piperidin-1-yl)methyl)phenyl)acrylamide;
(E)-3-(4-((4-((((1R,2S)-2-Phenylcyclopropyl)amino) methyl)piperidin-1-yl)methyl)phenyl)-N-(phenylsulfonyl)acrylamide.
N-Methoxy-4-((4-(((trans)-2-phenylcyclopropyl)amino)piperidin-1-yl)methyl)benzamide;
N-(Methylsulfonyl)-4-((4-(((trans)-2-phenylcyclopropyl) amino)piperidin-1-yl)methyl)benzamide;
N-(Benzyloxy)-4-((4-(((trans)-2-phenylcyclopropyl)amino) piperidin-1-yl)methyl)benzamide;
N-Phenoxy-4-((4-(((trans)-2-phenylcyclopropyl)amino)piperidin-1-yl)methyl)benzamide;
N-(Benzyl sulfonyl)-4-((4-(((trans)-2-phenylcyclopropyl) amino)piperidin-1-yl)methyl)benzamide;
N-Methyl-N-(methyl sulfonyl)-4-((4-(((trans)-2-phenylcyclopropyl)amino)piperidin-1-yl)methyl)benzamide;
4-((4-(((trans)-2-Phenylcyclopropyl)amino)piperidin-1-yl) methyl)-N-(phenyl sulfonyl)benzamide;
N-(Isopropyl sulfonyl)-4-((4-(((trans)-2-phenylcyclopropyl) amino)piperidin-1-yl)methyl)benzamide;
4-((4-(((trans)-2-Phenylcyclopropyl)amino)piperidin-1-yl) methyl)-N-(propyl sulfonyl)benzamide;
N-(Ethylsulfonyl)-4-((4-(((trans)-2-phenylcyclopropyl) amino)piperidin-1-yl)methyl)benzamide;
N-(tert-Butylsulfonyl)-4-((4-(((trans)-2-phenylcyclopropyl) amino)piperidin-1-yl)methyl)benzamide;
4-((4-(((trans)-2-Phenylcyclopropyl)amino)piperidin-1-yl) methyl)-N-tosylbenzamide;
N-((4-Fluorophenyl)sulfonyl)-4-((4-(((trans)-2-phenylcyclopropyl)amino)piperidin-1-yl)methyl)benzamide;
N-(Methylsulfonyl)-4-((4-(((1R,2S)-2-phenylcyclopropyl) amino)piperidin-1-yl)methyl)benzamide;
N-(Isopropylsulfonyl)-4-((4-(((1R,2S)-2-phenylcyclopropyl)amino)piperidin-1-yl)methyl)benzamide;
4-((4-(((1R,2S)-2-Phenylcyclopropyl)amino)piperidin-1-yl) methyl)-N-(phenyl sulfonyl)benzamide;
N-(cyclopropylsulfonyl)-4-((4-(((1R,2S)-2-phenylcyclopropyl)amino)piperidin-1-yl)methyl)benzamide;
4-((4-(((1R,2S)-2-phenylcyclopropyl)amino)piperidin-1-yl) methyl)-N-(propyl sulfonyl)benzamide;
N-(tert-butylsulfonyl)-4-((4-(((1R,2S)-2-phenylcyclopropyl)amino)piperidin-1-yl)methyl)benzamide;
N-(ethylsulfonyl)-4-((4-(((1R,2S)-2-phenylcyclopropyl) amino)piperidin-1-yl)methyl)benzamide;
N-methoxy-4-((4-(((1R,2S)-2-phenylcyclopropyl)amino)piperidin-1-yl)methyl)benzamide;

N-(Methylsulfonyl)-2-(4-((4-(((1R,2S)-2-phenylcyclopropyl)amino)piperidin-1-yl)methyl)phenyl)acetamide;

2-(4-((4-(((1R,2S)-2-phenylcyclopropyl)amino)piperidin-1-yl)methyl)phenyl)-N-(phenyl sulfonyl)acetamide;

N-(cyclopropylsulfonyl)-2-(4-((4-(((1R,2S)-2-phenylcyclopropyl)amino)piperidin-1-yl)methyl)phenyl)acetamide;

N-(ethylsulfonyl)-2-(4-((4-(((1R,2S)-2-phenylcyclopropyl)amino)piperidin-1-yl)methyl)phenyl)acetamide;

N-(isopropylsulfonyl)-2-(4-((4-(((1R,2S)-2-phenylcyclopropyl)amino)piperidin-1-yl)methyl)phenyl)acetamide;

N-ethoxy-4-((4-(((1R,2S)-2-phenylcyclopropyl)amino)piperidin-1-yl)methyl)benzamide;

(E)-N-(methylsulfonyl)-3-(4-((4-((((1R,2S)-2-phenylcyclopropyl)amino)methyl)piperidin-1-yl)methyl)phenyl)acrylamide;

(E)-N-(ethylsulfonyl)-3-(4-((4-((((1R,2S)-2-phenylcyclopropyl)amino)methyl)piperidin-1-yl)methyl)phenyl)acrylamide;

(E)-N-(cyclopropylsulfonyl)-3-(4-((4-((((1R,2S)-2-phenylcyclopropyl)amino)methyl)piperidin-1-yl)methyl)phenyl)acrylamide;

(E)-N-methyl-N-(methylsulfonyl)-3-(4-((4-((((1R,2S)-2-phenylcyclopropyl)amino)methyl)piperidin-1-yl)methyl)phenyl)acrylamide;

N-(Methylsulfonyl)-4-((4-((((1R,2S)-2-phenylcyclopropyl)amino)methyl)piperidin-1-yl)methyl)benzamide;

N-(cyclopropylsulfonyl)-4-((4-((((1R,2S)-2-phenylcyclopropyl)amino)methyl)piperidin-1-yl)methyl)benzamide;

N-methyl-N-(methylsulfonyl)-4-((4-((((1R,2S)-2-phenylcyclopropyl)amino)methyl)piperidin-1-yl)methyl)benzamide;

4-((4-((((1R,2S)-2-phenylcyclopropyl)amino)methyl)piperidin-1-yl)methyl)-N-(phenyl sulfonyl)benzamide;

N-(Methylsulfonyl)-4-((4-((((1R,2S)-2-phenylcyclopropyl)amino)methyl)piperidin-1-yl)methyl)benzamide;

and pharmaceutically acceptable salts of the foregoing compounds, including, but not limited to, dihydrochloride salts.

The compounds of formula (I) and formula (Ia)-(Ill) may be formulated into pharmaceutical compositions.

Pharmaceutical Compositions

In another aspect, the invention provides pharmaceutical compositions comprising a LSD1 inhibitor according to the invention and a pharmaceutically acceptable carrier, excipient, or diluent. Compounds of the invention may be formulated by any method well known in the art and may be prepared for administration by any route, including, without limitation, parenteral, oral, sublingual, transdermal, topical, intranasal, intratracheal, or intrarectal. In certain Exemplary embodiments, compounds of the invention are administered intravenously in a hospital setting. In certain other Exemplary embodiments, administration may preferably be by the oral route.

The characteristics of the carrier will depend on the route of administration. As used herein, the term "pharmaceutically acceptable" means a non-toxic material that is compatible with a biological system such as a cell, cell culture, tissue, or organism, and that does not interfere with the effectiveness of the biological activity of the active ingredient(s). Thus, compositions according to the invention may contain, in addition to the inhibitor, diluents, fillers, salts, buffers, stabilizers, solubilizers, and other materials well known in the art. The preparation of pharmaceutically acceptable formulations is described in, e.g., Remington's Pharmaceutical Sciences, 18th Edition, ed. A. Gennaro, Mack Publishing Co., Easton, Pa., 1990.

As used herein, the term pharmaceutically acceptable salts refers to salts that retain the desired biological activity of the above-identified compounds and exhibit minimal or no undesired toxicological effects. Examples of such salts include, but are not limited to acid addition salts formed with inorganic acids (for example, hydrochloric acid, hydrobromic acid, sulfuric acid, phosphoric acid, nitric acid, and the like), and salts formed with organic acids such as acetic acid, oxalic acid, tartaric acid, succinic acid, malic acid, ascorbic acid, benzoic acid, tannic acid, pamoic acid, alginic acid, polyglutamic acid, naphthalenesulfonic acid, naphthalenedisulfonic acid, and polygalacturonic acid. The compounds can also be administered as pharmaceutically acceptable quaternary salts known by those skilled in the art, which specifically include the quaternary ammonium salt of the formula —NR+Z—, wherein R is hydrogen, alkyl, or benzyl, and Z is a counterion, including chloride, bromide, iodide, —O-alkyl, toluenesulfonate, methylsulfonate, sulfonate, phosphate, or carboxylate (such as benzoate, succinate, acetate, glycolate, maleate, malate, citrate, tartrate, ascorbate, benzoate, cinnamoate, mandeloate, benzyloate, and diphenylacetate).

The active compound is included in the pharmaceutically acceptable carrier or diluent in an amount sufficient to deliver to a patient a therapeutically effective amount without causing serious toxic effects in the patient treated. An exemplary dose of the active compound for all of the above-mentioned conditions is in the range from about 0.01 to 300 mg/kg, preferably 0.1 to 100 mg/kg per day, more generally 0.5 to about 25 mg per kilogram body weight of the recipient per day. A typical topical dosage will range from 0.01-3% wt/wt in a suitable carrier. The effective dosage range of the pharmaceutically acceptable derivatives can be calculated based on the weight of the parent compound to be delivered. If the derivative exhibits activity in itself, the effective dosage can be estimated as above using the weight of the derivative, or by other means known to those skilled in the art.

The pharmaceutical compositions comprising compounds of the present invention may be used in the methods described herein.

Methods of Use

In yet another aspect, the invention provides for methods for inhibiting LSD1 activity in a cell, comprising contacting the cell in which inhibition of LSD1 activity is desired with an effective amount of a compound of formula (I) or any one of formulae (Ia)-(Ill), pharmaceutically acceptable salts thereof or pharmaceutical compositions containing the compound or pharmaceutically acceptable salt thereof.

The compositions and methods provided herein are particularly deemed useful for inhibiting LSD1 activity in a cell. In one embodiment, a cell in which inhibition of LSD1 activity is desired is contacted with an effective amount of a compound of formula (I) to negatively modulate the activity of LSD1. In some embodiments, a therapeutically effective amount of pharmaceutically acceptable salt or pharmaceutical compositions containing the compound of formula (I) or any one of formulae (Ia)-(Ill) may be used.

By negatively modulating the activity of LSD1, particularly in cases for cells overexpressing the LSD1 enzyme or somatic mutations that activate the LSD1 enzyme, the methods are designed to restore normal cellular transcription expression patterns, e.g., by altering methylation pattern of H3K4, to inhibition undesired cellular proliferation resulting from enhanced LSD1 activity within the cell. The cells may be contacted in a single dose or multiple doses in accordance with a particular treatment regimen to effect the desired negative modulation of LSD1. The degree of mono- and dimethylation of histone H3K4 or H3K9 may be monitored in the cell using well known methods, including those described in Example A below, to access the effectiveness of treatment and dosages may be adjusted accordingly, such as by an attending medical practitioner when the cell is in a human body.

In another aspect, methods of treating LSD1-mediated cancer comprising administering to a patient having cancer a therapeutically effective amount of a compound of formula (I) or one of formulae (Ia)-(Ill), pharmaceutically acceptable salts thereof or pharmaceutical compositions comprising the compound or pharmaceutically acceptable salts thereof are provided.

The compositions and methods provided herein may be used for the treatment of a wide variety of LSD1-mediated cancers, including tumors such as lung, prostate, breast, brain, skin, cervical carcinomas, testicular carcinomas, etc. More particularly, LSD1-mediated cancers that may be treated by the compositions and methods of the invention include, but are not limited to, tumor types such as astrocytic, breast, cervical, colorectal, endometrial, esophageal, gastric, head and neck, hepatocellular, laryngeal, lung, oral, ovarian, prostate and thyroid carcinomas and sarcomas. More specifically, these compounds can be used to treat the following LSD1-mediated cancers: Cardiac: sarcoma (angiosarcoma, fibrosarcoma, rhabdomyosarcoma, liposarcoma), myxoma, rhabdomyoma, fibroma, lipoma and teratoma; Lung: bronchogenic carcinoma (squamous cell, undifferentiated small cell, undifferentiated large cell, adenocarcinoma), alveolar (bronchiolar) carcinoma, bronchial adenoma, sarcoma, lymphoma, chondromatous hamartoma, mesothelioma; Gastrointestinal: esophagus (squamous cell carcinoma, adenocarcinoma, leiomyosarcoma, lymphoma), stomach (carcinoma, lymphoma, leiomyosarcoma), pancreas (ductal adenocarcinoma, insulinoma, glucagonoma, gastrinoma, carcinoid tumors, vipoma), small bowel (adenocarcinoma, lymphoma, carcinoid tumors, Kaposi's sarcoma, leiomyoma, hemangioma, lipoma, neurofibroma, fibroma), large bowel (adenocarcinoma, tubular adenoma, villous adenoma, hamartoma, leiomyoma); Genitourinary tract: kidney (adenocarcinoma, Wilm's tumor (nephroblastoma), lymphoma, leukemia), bladder and urethra (squamous cell carcinoma, transitional cell carcinoma, adenocarcinoma), prostate (adenocarcinoma, sarcoma), testis (seminoma, teratoma, embryonal carcinoma, teratocarcinoma, choriocarcinoma, sarcoma, interstitial cell carcinoma, fibroma, fibroadenoma, adenomatoid tumors, lipoma); Liver: hepatoma (hepatocellular carcinoma), cholangiocarcinoma, hepatoblastoma, angiosarcoma, hepatocellular adenoma, hemangioma; Biliary tract: gall bladder carcinoma, ampullary carcinoma, cholangiocarcinoma; Bone: osteogenic sarcoma (osteosarcoma), fibrosarcoma, malignant fibrous histiocytoma, chondrosarcoma, Ewing's sarcoma, malignant lymphoma (reticulum cell sarcoma), multiple myeloma, malignant giant cell tumor chordoma, osteochronfroma (osteocartilaginous exostoses), benign chondroma, chondroblastoma, chondromyxofibroma, osteoid osteoma and giant cell tumors; Nervous system: skull (osteoma, hemangioma, granuloma, xanthoma, osteitis deformans), meninges (meningioma, meningiosarcoma, gliomatosis), brain (astrocytoma, medulloblastoma, glioma, ependymoma, germinoma (pinealoma), glioblastoma multiform, oligodendroglioma, schwannoma, retinoblastoma, congenital tumors), spinal cord neurofibroma, meningioma, glioma, sarcoma); Gynecological: uterus (endometrial carcinoma), cervix (cervical carcinoma, pre-tumor cervical dysplasia), ovaries (ovarian carcinoma (serous cystadenocarcinoma, mucinous cystadenocarcinoma, unclassified carcinoma), granulosa-thecal cell tumors, Sertoli-Leydig cell tumors, dysgerminoma, malignant teratoma), vulva (squamous cell carcinoma, intraepithelial carcinoma, adenocarcinoma, fibrosarcoma, melanoma), vagina (clear cell carcinoma, squamous cell carcinoma, botryoid sarcoma (embryonal rhabdomyosarcoma), fallopian tubes (carcinoma); Hematologic: blood (myeloid leukemia (acute and chronic), acute lymphoblastic leukemia, chronic lymphocytic leukemia, myeloproliferative diseases, multiple myeloma, myelodysplastic syndrome), Hodgkin's disease, non-Hodgkin's lymphoma (malignant lymphoma); Skin: malignant melanoma, basal cell carcinoma, squamous cell carcinoma, Kaposi's sarcoma, moles dysplastic nevi, lipoma, angioma, dermatofibroma, keloids, psoriasis; and Adrenal glands: neuroblastoma. In certain embodiments, the cancer is non-small cell lung cancer.

The concentration and route of administration to the patient will vary depending on the cancer to be treated. The compounds, pharmaceutically acceptable salts thereof and pharmaceutical compositions comprising such compounds and salts also may be co-administered with other anti-neoplastic compounds, e.g., chemotherapy, or used in combination with other treatments, such as radiation or surgical intervention, either as an adjuvant prior to surgery or post-operatively. The degree of mono- and dimethylation of histone H3K4 or H3K9 may be monitored in the patient using well known methods, including those described in Example A below, to access the effectiveness of treatment, along with other prognostic or biological factors, and dosages may be adjusted accordingly by the attending medical practitioner.

REACTION SCHEMES AND EXAMPLES

The compounds of the present invention may be prepared using commercially available reagents using the synthetic methods and reaction schemes described herein, or using other reagents and conventional methods well known to those skilled in the art.

For instance, compounds of the present invention may be prepared according to the General Reaction Schemes I and II.

General Reaction Schemes

Compounds of formula (I) where $R^1$ is —C(O)NR$^4$OR$^5$, —C(O)NR$^4$SO$_2$R$^6$; —CH=CH—C(O)NR$^4$OR$^5$, or —CH=CH—C(O)NR$^4$SO$_2$R$^6$, m=1, and n=1 may be synthesized according to the General Reaction Schemes I and II.

Thus, benzylic bromides A (either commercially available or known in the art) where $R^1$ is —C(O)OC$_{1-4}$-alkyl, or —CH=CH—C(O)OC$_{1-4}$-alkyl, react with the carbonyl substituted nitrogen containing heterocycles B to afford benzylated compounds C (step 1). The alkylation reaction proceeds in solvents like THF, MeCN, DMF, DMA, MeOH, EtOH, acetone, MEK, dioxane and like, or mixtures thereof; at temperatures ranging from 20 to 120° C. in the presence of bases such as Et$_3$N, DIPEA, NaH, NaOH, K$_2$CO$_3$, Cs$_2$CO$_3$ and like.

General Reaction Scheme I

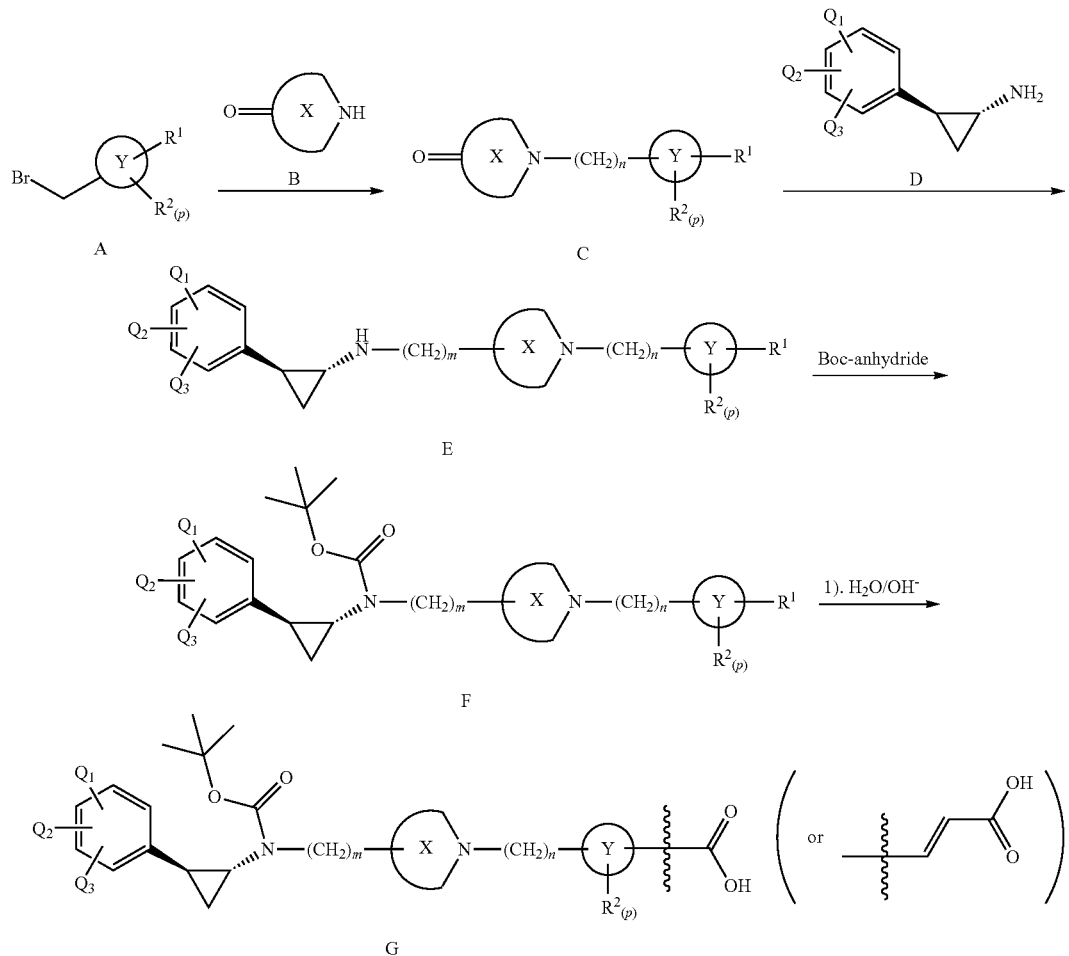

Compounds C undergo reductive amination reactions with phenyl cyclopropylamines D to afford compounds E where $R^1$ is —C(O)OC$_{1-4}$-alkyl, or —CH=CH—C(O)OC$_{1-4}$-alkyl and m=n=1 (step 2). The reaction typically proceeds in solvents such as MeOH, DCM, THF, DCE, dioxane and like using sodium hydride, sodium triacetoxyborohydride as the reducing agents at temperatures ranging from −20 to 60° C. Compounds E further react with Boc-anhydride to form N-Boc-protected species F. The reactions typically proceed in the presence of an alkali, in mixtures of solvents such as water-THF, water-dioxane and the like, at temperatures ranging from −20 to 60° C. Compounds F undergo alkaline hydrolysis to afford acids G ready for coupling reactions with amines and related compounds. The reactions proceed in the presence of an alkali, preferably LiOH in mixtures of water with THF, dioxane, MeOH, EtOH, isopropanol or acetone, at temperatures ranging from 10 to 100° C.

General Reaction Scheme II

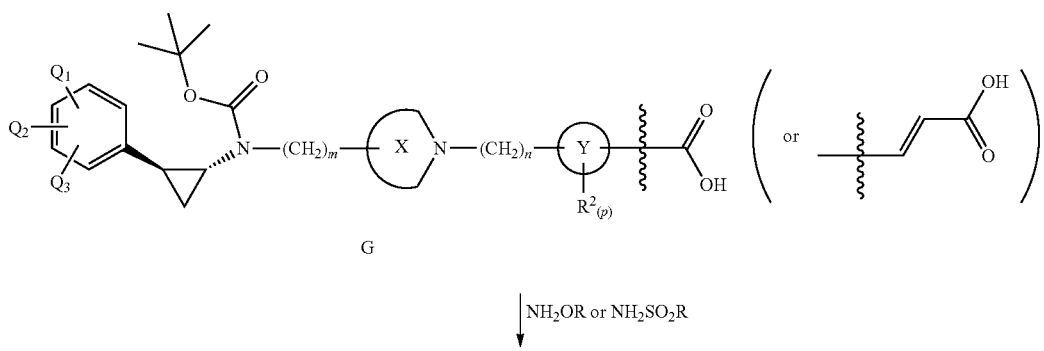

-continued

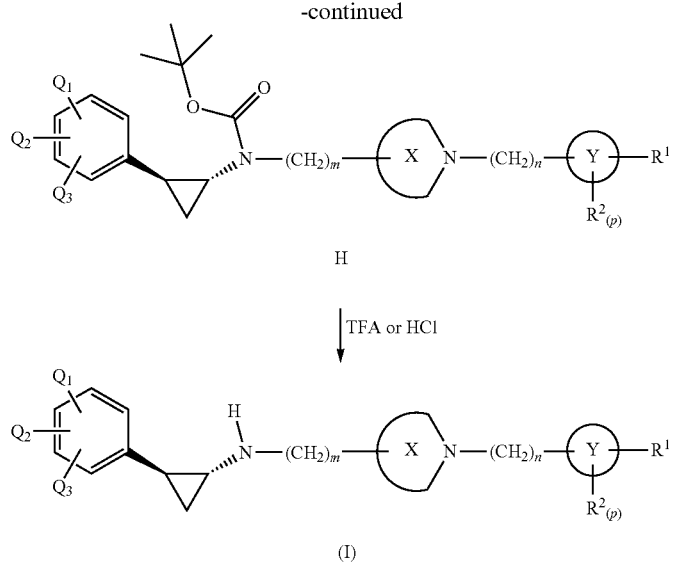

The acids G undergo coupling reactions either with alkoxyamines or sulfonamides to afford compounds H where $R^1$ is —C(O)NR$^4$OR$^5$, —C(O)NR$^4$SO$_2$R$^6$; —CH=CH—C(O)NR$^4$OR$^5$, or —CH=CH—C(O)NR$^4$SO$_2$R$^6$ and m=1 and n=1 (scheme II, step 1). The reactions proceed under the conditions known in the art at temperatures ranging from 0 to 50° C. Finally, compound H undergo Boc-de-protection reaction to afford Compounds (I) (scheme II, step 2). The de-protection proceeds in the presence of TFA or HCl in solvents such as DCM, dioxane, MeOH, EA, DCE, chloroform, ether and MTBA at temperatures ranging from −10 to 50° C. Compounds (I) can be isolated either as free bases or their hydrochloride salts.

Following the teachings of General Reaction Schemes I and II, Schemes 1-18 set forth in Examples 1-57 and other methods well known in the art, compounds of formula (Ia)-(Ill) may be prepared as set forth in Table 1:

TABLE 1

Compounds of Formula (Ia)-(Ill)

TABLE 1-continued
Compounds of Formula (Ia)-(Ill)
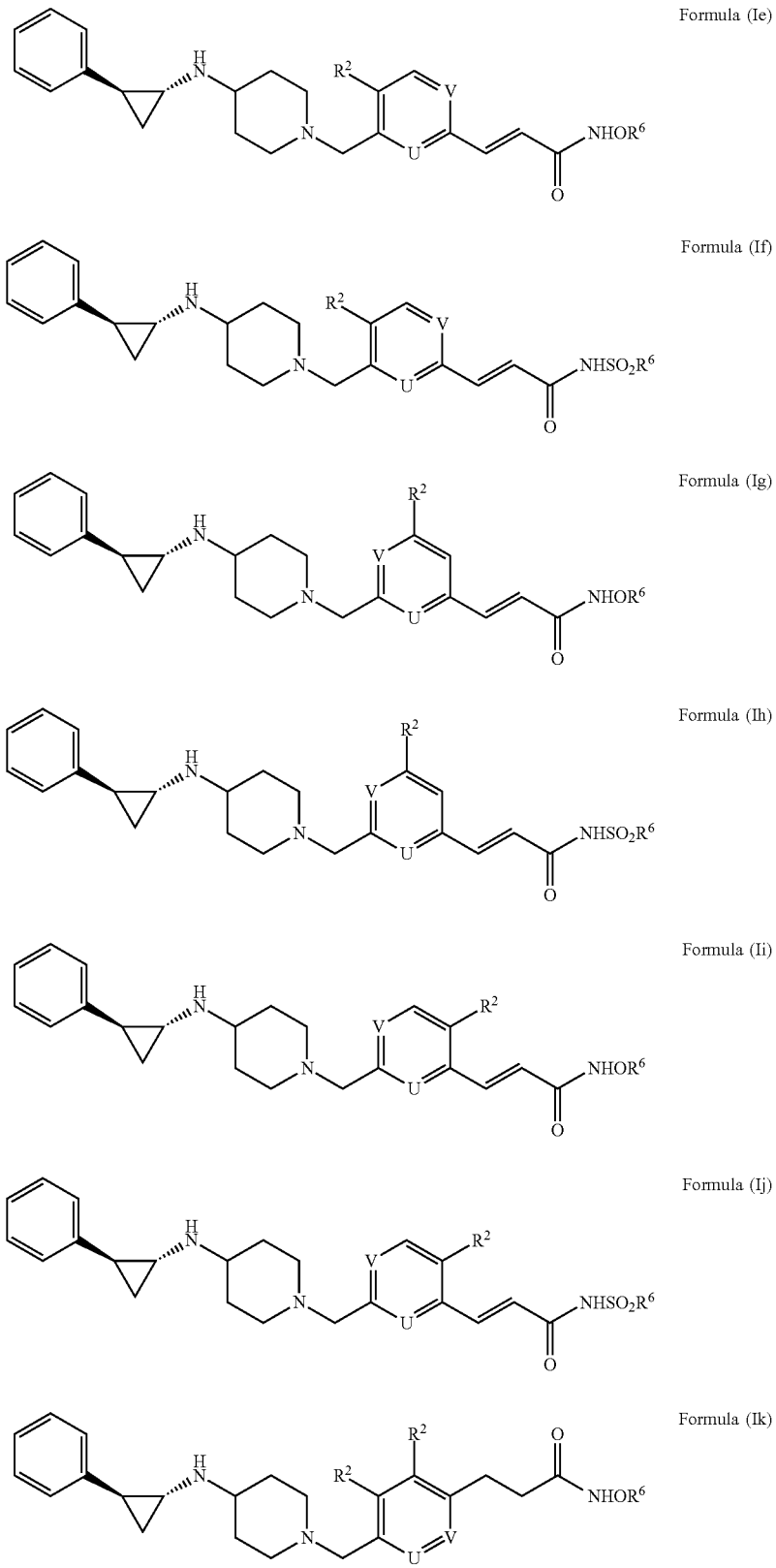
Formula (Ie)
Formula (If)
Formula (Ig)
Formula (Ih)
Formula (Ii)
Formula (Ij)
Formula (Ik)

TABLE 1-continued
Compounds of Formula (Ia)-(Ill)
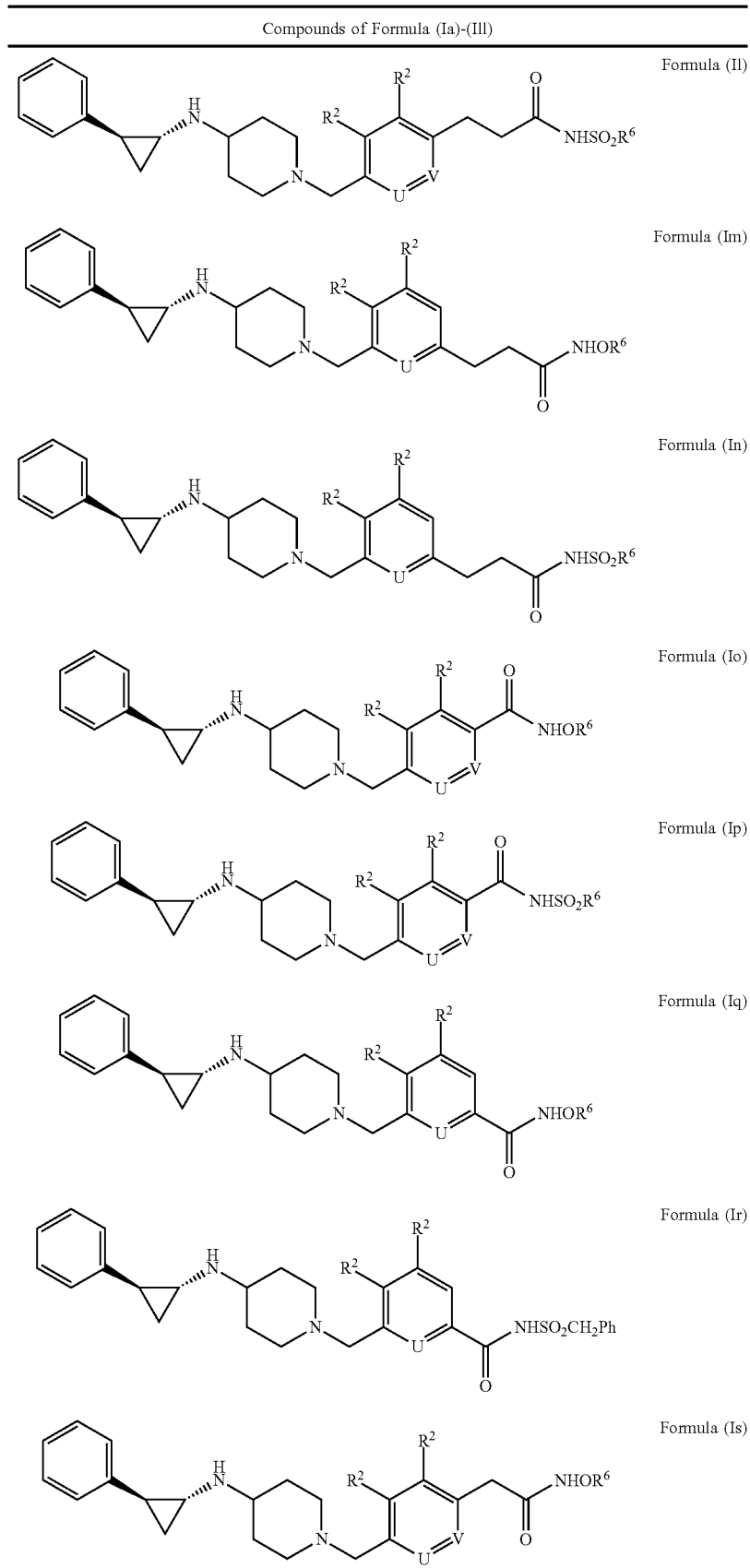

TABLE 1-continued

Compounds of Formula (Ia)-(Ill)

Formula (It)

Formula (Iu)

Formula (Iv)

Formula (Iw)

Formula (Ix)

Formula (Iy)

Formula (Iz)

Formula (Iaa)

TABLE 1-continued
Compounds of Formula (Ia)-(Ill)
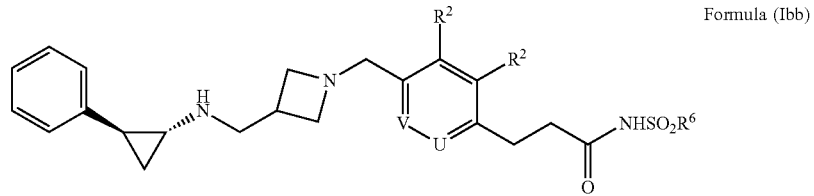
Formula (Ibb)
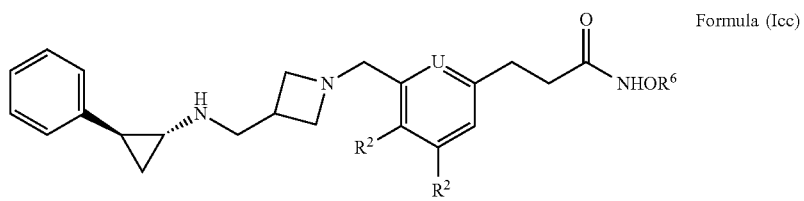
Formula (Icc)
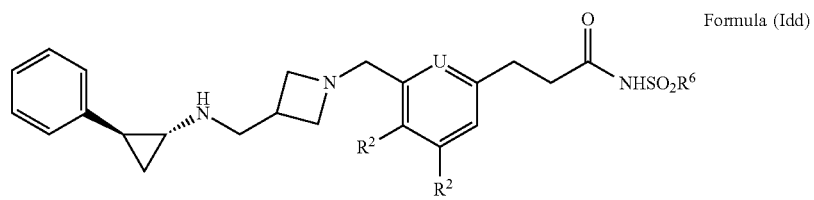
Formula (Idd)
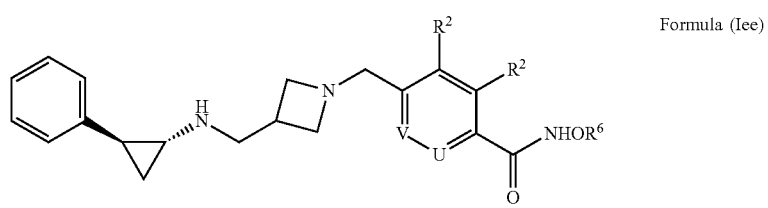
Formula (Iee)
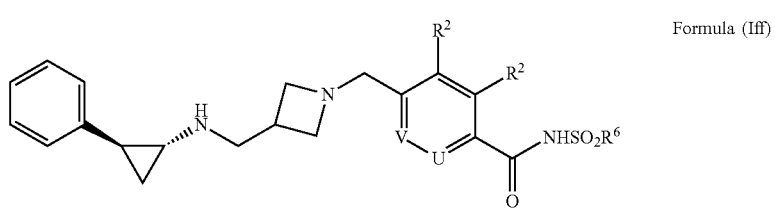
Formula (Iff)
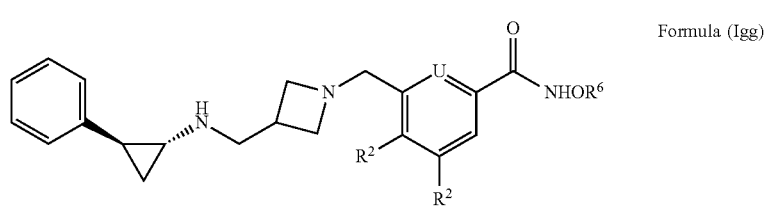
Formula (Igg)
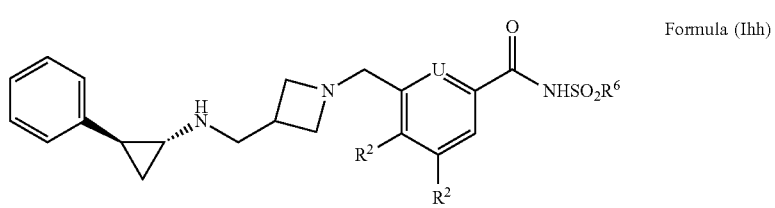
Formula (Ihh)

wherein U and V are each independently —CH— or —N— and $R^2$ and $R^6$ are defined as in formula (I). In certain embodiments, each $R^2$ is independently hydrogen, halogen or alkyl, preferably methyl, fluoro, chloro or bromo, and $R^6$ is alkyl or aryl, preferably methyl, phenyl or benzyl.

The following Examples are intended to illustrate further certain exemplary embodiments of the invention and are not intended to limit the scope of the invention.

Intermediate Compound 6

(E)-3-(4-((4-(((tert-Butoxycarbonyl)((trans)-2-phenylcyclopropyl)amino)piperidin-1-yl)methyl)phenyl) acrylic acid (6)

Scheme 1

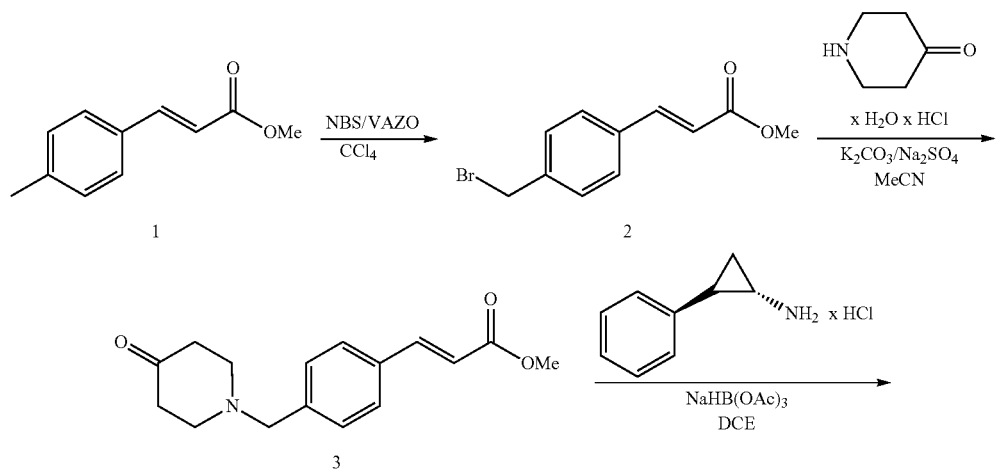

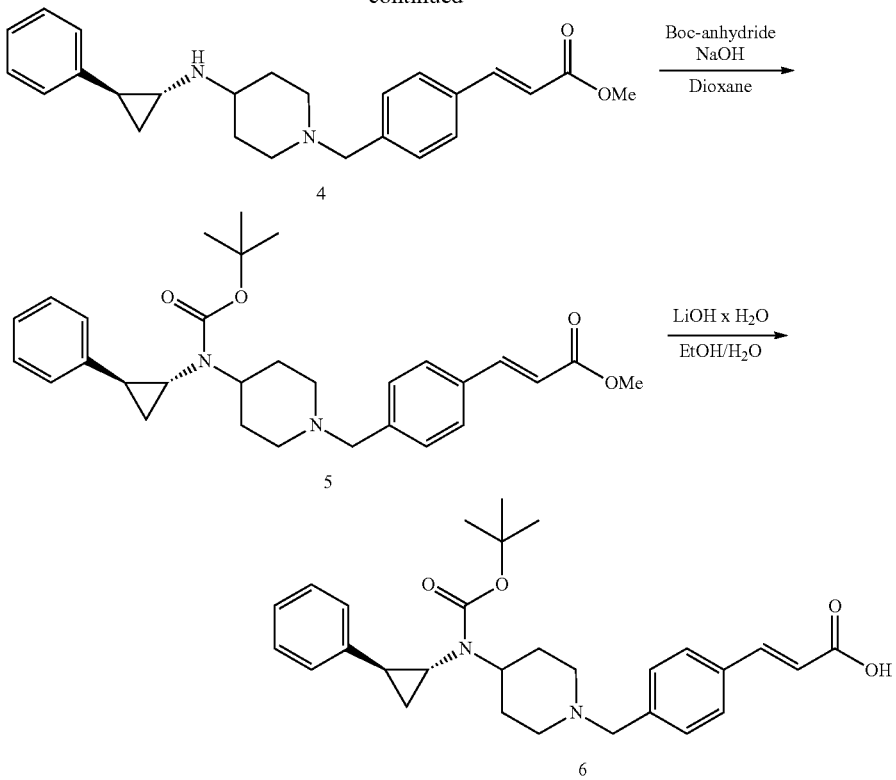

Step 1. (E)-Methyl 3-(4-(bromomethyl)phenyl)acrylate (2)

To a solution of (E)-methyl 3-(p-tolyl)acrylate (1) (5.19 g, 29.5 mmol) (*Journal of Chemical Ecology*, 34(3), p. 339, 2008) in $CCl_4$ (70 mL) was added NBS (5.24 g, 29.5 mmol) and 1,1'-azobis(cyclohexanecarbonitrile) (VAZO) (300 mg, 0.042 mmol). The reaction mixture was heated at reflux conditions for 24 hours, cooled down to RT and the solids were removed by filtration. The filtrate was washed with $NaHCO_3$ solution then brine, dried over anhydrous $MgSO_4$, filtered and evaporated. The residue was purified by flash column chromatography, eluent 10 then 20% EA in hexanes to afford title compound 2 (4.80 g, 64% yield) as oil that has solidified in vacuum.

$^1$H NMR: 500 MHz, $CDCl_3$, δ (ppm): 7.67 (d, J=16.0 Hz, 1H), 7.50 (d, J=8.1 Hz, 2H), 7.41 (d, J=8.2 Hz, 2H), 6.44 (d, J=16.0 Hz, 1H), 4.49 (s, 2H), 3.81 (s, 3H).

Purity of the product (based on its NMR spectrum) is 91% with the rest being un-reacted Compound 1. The material was taken to the next step with no additional purification.

Step 2. (E)-Methyl 3-(4-((4-oxopiperidin-1-yl)methyl)phenyl)acrylate (3)

A suspension of compound 2 (2.40 g, 8.56 mmol), 4-piperidone hydrochloride monohydrate (1.97 g, 12.84 mmol), potassium carbonate (4.73 g, 34.2 mmol) and anhydrous $Na_2SO_4$ (2.43 g, 17.1 mmol) in MeCN (40 mL) was stirred at reflux conditions for 21 hrs. The mixture was cooled to RT, evaporated and the residue was partitioned between water and EA. The organic phase washed with brine dried over anhydrous $Na_2SO_4$, filtered and evaporated. The residue was purified by flash column chromatography, eluent EA to afford title compound 3 (1.765 g, 75% yield) as oil which has solidified in vacuum. MS: 273.3 (calcd.), 274.1 (M+H$^+$, found).

Step 3. (E)-Methyl 3-(4-((4-((trans)-2-phenylcyclopropylamino)piperidin-1-yl)methyl)phenyl)acrylate (4)

A suspension of (1R, 2S)-2-phenylcyclopropanamine hydrochloride (1.37 g, 8.08 mmol) and compound 3 (1.84 g, 6.73 mmol) in DCE (25 mL) was stirred at RT for 2.0 hrs, cooled to 0° C. then treated with the borohydride (3.14 g, 14.81 mmol). The mixture was allowed to warm to RT and stirred for 14 hrs. The mixture was then diluted with DCM and washed with a mixture of saturated $NaHCO_3$ solution and 0.5 N NaOH (pH 8-9). The organic phase was washed with brine, dried over anhydrous $MgSO_4$, filtered, concentrated and purified by flash column chromatography, eluent 5% then 10% MeOH in DCM (MeOH contained 2% ammonia) to form title compound 4 (2.154 g, 82% yield). as oil. MS: 390.5 (calcd.), 391.0 (M+H$^+$, found).

Step 4. (E)-Methyl 3-(4-((4-(tert-butoxycarbonyl((trans)-2-phenylcyclopropyl) amino)piperidin-1-yl)methyl)phenyl)acrylate (5)

To a solution of compound 4 (2.154 g, 5.52 mmol) and Boc-anydride (1.806 g, 8.27 mmol) in dioxane (35 mL) was added a solution of NaOH (0.882 g, 22.06 mmol) in water (12 mL). The reaction mixture was stirred at RT for 4 hrs. Then more Boc-anydride (1.0 g, 4.58 mmol) in dioxane (10 mL) was added and the reaction mixture was left to stir at RT for an additional 72 hrs. The mixture was diluted with water and extracted with EA. The extract was washed with brine, dried over anhydrous $MgSO_4$, filtered and concentrated. The resultant viscous oil was subjected to flash column chromatography, eluent EA to afford title compound 5 (2.436 g, 90% yield) as viscous oil. MS: 490.6 (calcd.), 491.0 (M+H$^+$, found).

Step 5. (E)-3-(4-((4-(tert-Butoxycarbonyl((trans)-2-phenylcyclopropyl)amino) piperidin-1-yl)methyl) phenyl)acrylic acid (6)

To a solution of compound 5 (2.436 g, 4.97 mmol) in 70% aqueous EtOH (40 mL) was added a hazy solution of LiOH×H$_2$O (0.833 g, 21.0 mmol) in 10 mL water. The reaction mixture was stirred at 80° C. for 8 hrs, cooled to RT, acidified to pH 4 then evaporated to its maximum. The residue was treated with brine and the resultant precipitate was collected by filtration. The precipitate was air-dried then dissolved in acetone. The resultant solution was treated with anhydrous MgSO$_4$, filtered and the filtrate was evaporated to afford title compound 6 (1.59 g, 67% yield).

$^1$H NMR: 500 MHz, DMSO-d$_6$, δ (ppm): 7.62 (d, J=8.2 Hz, 2H), 7.55 (d, J=16.0 Hz, 1H), 7.31 (d, J=8.2 Hz, 2H), 7.28-7.25 (m, 2H), 7.17-7.10 (m, 3H), 6.49 (d, J=16.0 Hz, 1H), 3.56-3.50 (m, 1H), 3.46 (d, J=3.6 Hz, 2H), 2.85-2.79 (m, 2H), 2.57-2.53 (m, 1H), 2.09-1.81 (m, 5H), 1.67-1.59 (m, 2H), 1.33-1.30 (m, 10H), 1.24-1.20 (m, 1H). MS: 476.6 (calcd.), 477.0 (M+H$^+$, found).

Example 1

(E)-N-Methoxy-3-(4-((4-(((trans)-2-phenylcyclopropyl)amino)piperidin-1-yl)methyl)phenyl)acrylamide di-hydrochloride (8)

Step 1. tert-Butyl (1-(4-((E)-3-(methoxyamino)-3-oxoprop-1-en-1-yl)benzyl)piperidin-4-yl)((trans)-2-phenylcyclopropyl)carbamate (7)

A solution of intermediate compound 6 (200 mg, 0.42 mmol), the DIPEA (0.314 mL, 1.804 mmol) and the HATU reagent (207 mg, 0.546 mmol) in 3 mL DMF was stirred for 90 min. To the solution was added methoxyamine hydrochloride (105 mg, 1.259 mmol) and the combined mixture was stirred at RT overnight then treated with brine. A precipitate was formed which was collected by filtration and dried. The crude product was then purified by flash column chromatography (eluent 5 then 10% MeOH in DCM) to afford title compound 7 as honey-like material (140 mg, 66% yield). MS: 505.7 (calcd.), 506.0 (M+H$^+$, found).

Step 2. (E)-N-Methoxy-3-(4-((4-(((trans)-2-phenylcyclopropyl)amino)piperidin-1-yl)methyl)phenyl) acrylamide di-hydrochloride (8)

To a suspension of compound 7 (140 mg, 0.277 mmol) in dioxane (1 mL) was added 4 M solution of HCl in dioxane (2 ml, 8.0 mmol). The reaction mixture was stirred at RT at for 3 hrs, evaporated to dryness. The resultant precipitate was triturated with EtOAc, collected by filtration and dried to afford title compound 8 (105 mg, 79% yield) as white solid.

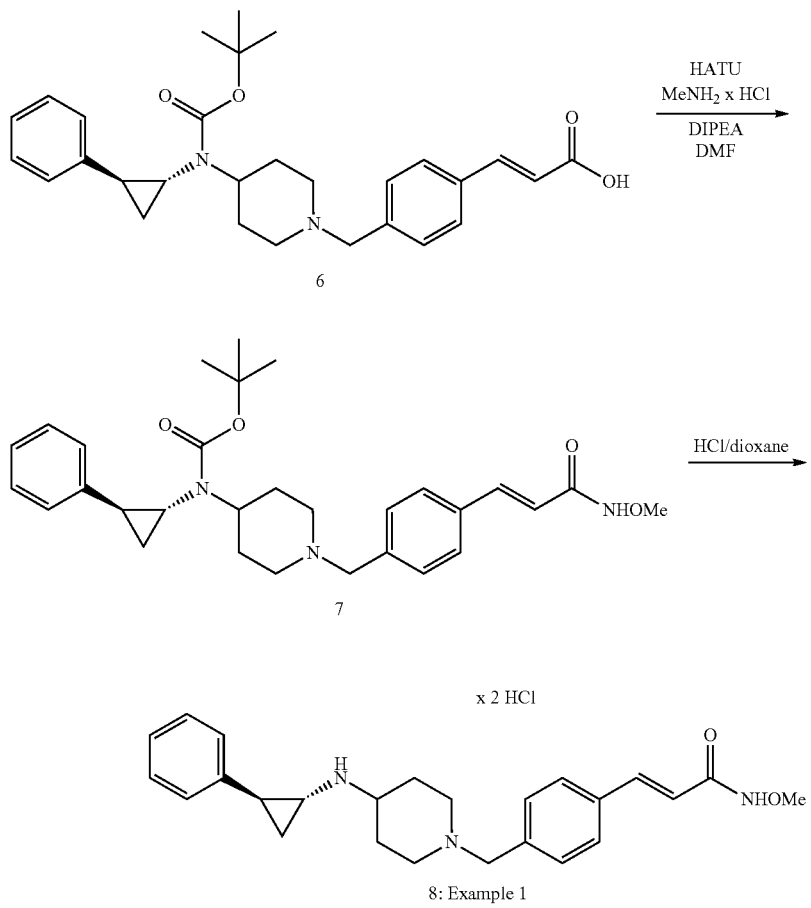

Scheme 2

$^1$H NMR: 500 MHz, DMSO-d$_6$, δ (ppm): 11.48 (bs, 1H), 11.03 (bs, 1H), 9.98 (bs, 2H), 7.70-7.62 (m, 4H), 7.52 (d, J=15.9 Hz, 1H), 7.31-7.28 (m, 2H), 7.23-7.16 (m, 3H), 6.52 (d, J=15.9 Hz, 1H), 4.27 (bs, 2H), 3.67 (s, 3H), 3.43 (bd, 3H), 2.99-2.92 (m, 3H), 2.56-2.52 (m, 1H), 2.28 (bs, 2H), 2.12-2.07 (m, 2H), 1.58-1.54 (m, 1H), 1.31-1.25 (m, 1H). MS: 405.5 (calcd.), 406.2 (M+H$^+$, found).

Example 2

(E)-N-(Methylsulfonyl)-3-(4-((4-(((trans)-2-phenyl-cyclopropyl)amino)piperidin-1-yl)methyl)phenyl)acrylamide di-hydrochloride (10)

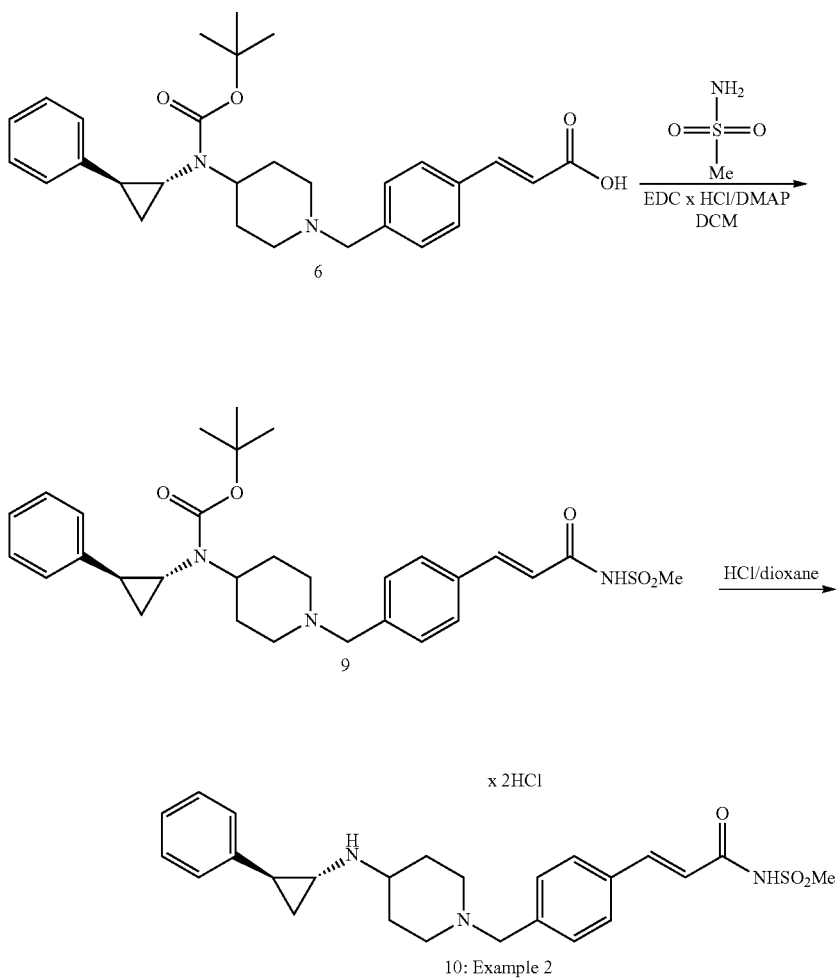

10: Example 2

Step 1. tert-Butyl (1-(4-((E)-3-(methylsulfonamido)-3-oxoprop-1-en-1-yl) benzyl)piperidin-4-yl)((trans)-2-phenylcyclopropyl)carbamate (9)

To a solution of compound 6 (200 mg, 0.420 mmol) and methyl sulfonamide (60 mg, 0.629 mmol) in DCM (6 mL) was added EDC×HCl (161 mg, 0.839 mmol) and DMAP (103 mg, 0.839 mmol) at RT. The reaction mixture was stirred at the same conditions overnight, diluted with more DCM then washed sequentially with a NaHCO$_3$ solution, water and brine. The organic solution was dried over anhydrous Na$_2$SO$_4$, filtered and evaporated. The residue was purified by flash column chromatography, eluent 5, then 10% MeOH in DCM (MeOH contained 2% ammonia), to afford title compound 9 (92 mg, 40% yield) as fluffy solid. MS: 553.7 (calcd.), 554.0 (M+H$^+$, found).

Step 2. (E)-N-(Methylsulfonyl)-3-(4-((4-(((trans)-2-phenylcyclopropyl)amino) piperidin-1-yl)methyl)phenyl)acrylamide di-hydrochloride (10)

To a suspension of the compound 9 (92 mg, 0.166 mmol) in dioxane (1 mL) was added a 4M solution of HCl in dioxane (2 mL, 8.0 mmol) at RT. The mixture was stirred at ambient temperature for 3 hrs, evaporated to dryness and the resultant white precipitate was triturated with a mixture of MeOH and acetone, collected by filtration and dried, to afford title compound 10 (79 mg, 90% yield) as off-white solid.

$^1$H NMR: 500 MHz, DMSO-d$_6$, δ (ppm): 12.01 (bs, 1H), 11.09 (bs, 1H), 9.96 (bs, 2H), 7.73-7.66 (m, 5H), 7.31-7.28 (m, 2H), 7.23-7.16 (m, 3H), 6.76 (d, J=15.9 Hz, 1H), 4.28 (bs, 2H), 3.44 (bd, 3H), 3.22 (s, 3H), 2.99 (bs, 2H), 2.93 (bs, 1H), 2.54 (bs, 1H), 2.28 (bs, 2H), 2.11 (bs, 2H), 1.57-1.55 (m, 1H), 1.30-1.25 (m, 1H). MS: 453.6 (calcd.), 454.2 (M+H$^+$, found).

(E)-3-(3-((4-(((tert-Butoxycarbonyl)((trans)-2-phenylcyclopropyl)amino)piperidin-1-yl)methyl)phenyl)acrylic acid (16)

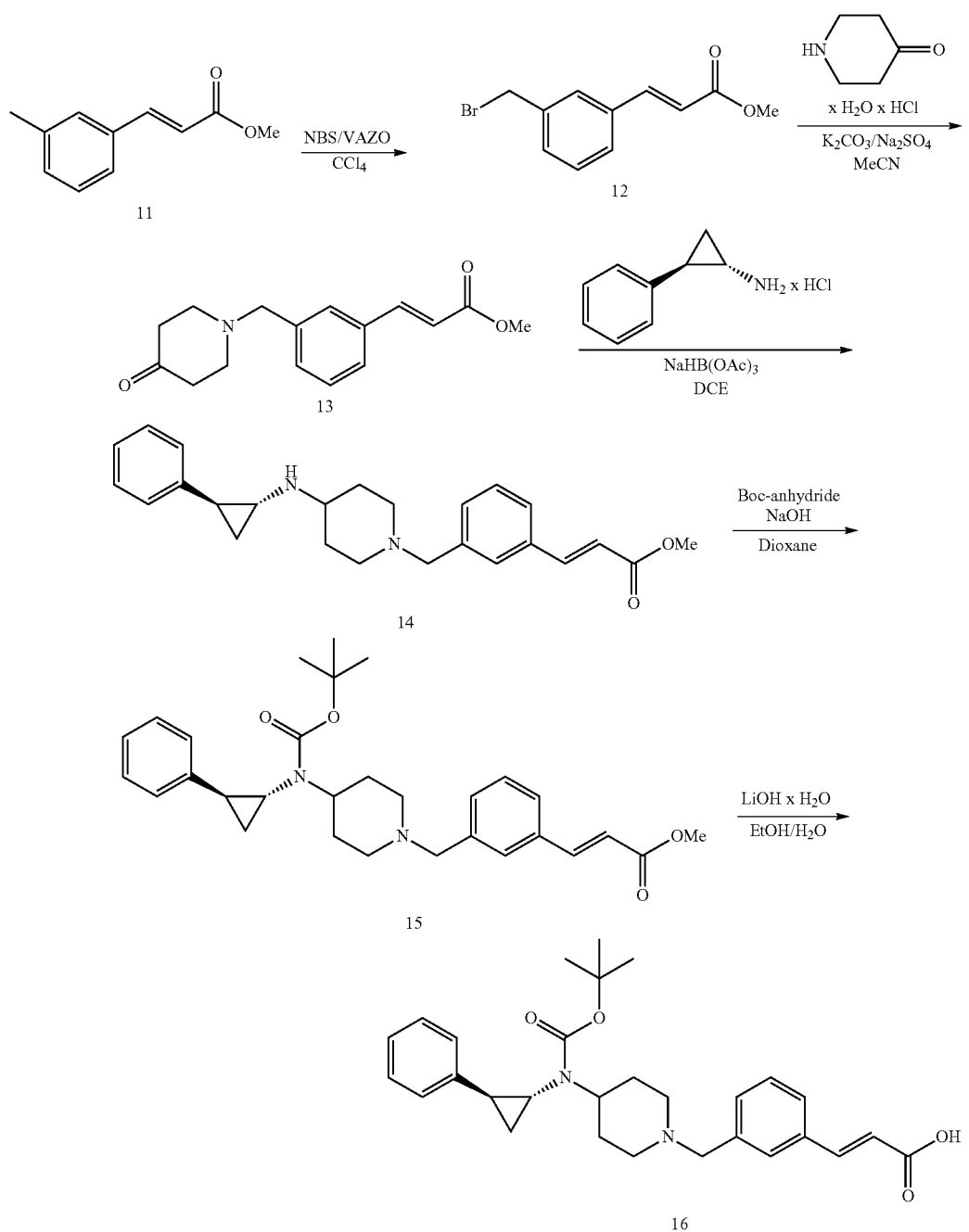

Scheme 4

Step 1. (E)-Methyl 3-(3-(bromomethyl)phenyl)acrylate (12)

To a solution of (E)-methyl 3-(m-tolyl)acrylate (11) (7.05 g, 40.0 mmol, WO 2008/153159) in CCl₄ (80 mL) was added NBS (7.12 g, 40.0 mmol) and VASO (0.5 g, 2.05 mmol). The reaction mixture was heated at reflux conditions for 22 hours, cooled down to RT and the floating succinimide was removed by filtration. The filtrate was washed with NaHCO₃ solution then brine, dried over anhydrous MgSO₄, filtered and evaporated. The residue was purified by flash column chromatography, eluent 5 then 10% EA in hexanes, to afford title compound 12 (2.06 g, 20% yield) as white solid. The material was used in the next step with no additional purification.

¹H NMR: 500 MHz, CDCl₃, δ (ppm): 7.68 (d, J=16.0 Hz, 1H), 7.54 (bs, 1H), 7.47-7.36 (m, 3H), 6.46 (d, J=16.1 Hz, 1H), 4.49 (s, 2H), 3.81 (s, 3H).

Step 2. (E)-Methyl 3-(3-((4-oxopiperidin-1-yl) methyl)phenyl)acrylate (13)

A suspension of compound 12 (1.5 g, 5.88 mmol), 4-piperidone hydrochloride monohydrate (1.355 g, 8.82 mmol), potassium carbonate (3.25 g, 23.52 mmol) and anhydrous Na$_2$SO$_4$ (1.67 g, 11.76 mmol) in MeCN (30 mL) was stirred at reflux conditions for 20 hrs. The mixture was cooled to RT, evaporated and the residue was partitioned between water and EA. The organic phase was washed with brine dried over anhydrous Na$_2$SO$_4$, filtered and evaporated. The residue was purified by flash column chromatography, eluent EA-hexanes (3:2) then pure EA to afford title compound 13 (1.139 g, 71% yield) as oil which has solidified in vacuum. MS: 273.3 (calcd.), 274.1 (M+H$^+$, found).

Step 3. (E)-Methyl 3-(3-((4-(((trans)-2-phenylcyclopropyl)amino)piperidin-1-yl)methyl)phenyl)acrylate (14)

A suspension of (1R, 2S)-2-phenylcyclopropanamine hydrochloride (1.13 g, 4.13 mmol) and compound 13 (0.842 g, 4.96 mmol) in DCE (20 mL) was stirred at RT for 2.0 hrs, cooled to 0° C. then treated with the sodium triacetoxyborohydride (1.752 g, 8.27 mmol). The mixture was allowed to warm to RT and stirred for 4 hrs. The mixture was then diluted with DCM and washed with a saturated NaHCO$_3$ solution. The organic phase was washed with brine, dried over anhydrous MgSO$_4$, filtered, concentrated and purified by flash column chromatography, eluent 5% then 10% MeOH in DCM (MeOH contained 2% ammonia) to provide title compound 14 (1.44 g, 89% yield) as oil. MS: 390.5 (calcd.), 391.1 (M+H$^+$, found).

Step 4. (E)-Methyl 3-(3-((4-((tert-butoxycarbonyl) ((trans)-2-phenylcyclopropyl) amino)piperidin-1-yl) methyl)phenyl)acrylate (15)

To a solution of compound 14 (1.17 g, 3.00 mmol) and Boc-anydride (1.635 g, 7.49 mmol) in dioxane (25 mL) was added a solution of NaOH (0.479 g, 11.98 mmol) in water (9 mL). The reaction mixture was stirred at RT for 24 hrs, diluted with water and extracted with EA. The extract was washed with brine, dried over anhydrous MgSO$_4$, filtered and concentrated. The resultant viscous oil was subjected to flash column chromatography, eluent EA—hexanes (4:1) then pure EA, to afford title compound 15 (1.22 g, 83% yield) as viscous oil. MS: 490.6 (calcd.), 491.1 (M+H$^+$, found).

Step 5. (E)-3-(3-((4-(((tert-Butoxycarbonyl)((trans)-2-phenylcyclopropyl) amino)piperidin-1-yl)methyl) phenyl)acrylic acid (16)

To a solution of compound 15 (1.22 g, 2.49 mmol) in 70% aqueous EtOH (30 mL) was added a hazy solution of LiOH×H$_2$O (0.417 g, 9.95 mmol) in water (10 mL). The reaction mixture was stirred at 80° C. for 5 hrs, cooled to RT, acidified to pH 5 then evaporated to its maximum. The residue was treated with brine and extracted with DCM. The extract was dried over anhydrous MgSO$_4$, filtered and the filtrate was evaporated to afford title compound 16 (1.08 g, 91% yield) as off-white foam.

$^1$H NMR: 500 MHz, CD$_3$OD, δ (ppm): 7.70 (bs, 1H), 7.67-7.65 (m, 1H), 7.60 (d, J=16.0 Hz, 1H), 7.51-7.45 (m, 2H), 7.29-7.26 (m, 2H), 7.19-7.13 (m, 3H), 6.58 (d, J=16.0 Hz, 1H), 4.09 (s, 2H), 3.88-3.82 (m, 1H), 4.40-3.36 (m, 2H), 2.85-2.80 (m, 2H), 2.71-2.68 (m, 1H), 2.45-2.36 (m, 1H), 2.31-2.23 (m, 1H), 2.17-1.13 (m, 1H), 2.01-1.93 (m, 2H), 1.47-1.41 (m, 10H), 1.28-1.23 (m, 1H). MS: 476.6 (calcd.), 477.1 (M+H$^+$, found).

Example 3

(E)-N-Methoxy-3-(3-((4-(((trans)-2-phenylcyclopropyl)amino)piperidin-1-yl)methyl)phenyl)acrylamide (18)

Scheme 5

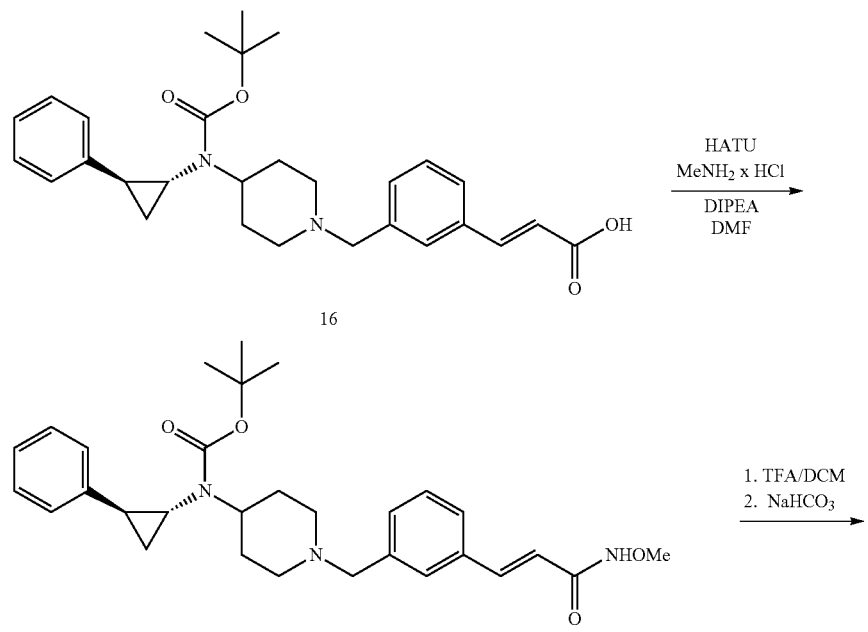

-continued

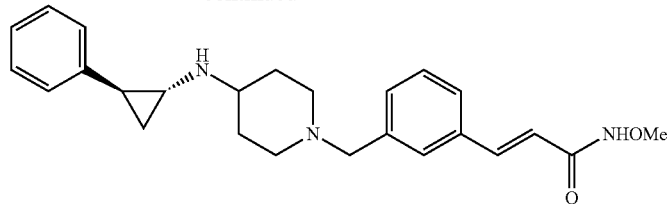

18: Example 3

Step 1. tert-Butyl (1-(3-((E)-3-(methoxyamino)-3-oxoprop-1-en-1-yl)benzyl)piperidin-4-yl)((trans)-2-phenylcyclopropyl)carbamate (17)

A solution of compound 16 (180 mg, 0.378 mmol), the DIPEA (0.283 mL, 1.624 mmol) and the HATU reagent (187 mg, 0.491 mmol) in 3 mL DMF was stirred for 90 min. To the solution was added methoxyamine hydrochloride (95 mg, 1.133 mmol) and the combined mixture was stirred at RT overnight then treated with brine. A precipitate was formed which was collected by filtration and dried. The crude product was purified by flash column chromatography (eluent 5 MeOH in DCM) to afford title compound 17 as glass-like material (156 mg, 82% yield). MS: 505.7 (calcd.), 506.0 (M+H+, found).

Step 2. (E)-N-Methoxy-3-(3-((4-(((trans)-2-phenyl-cyclopropyl)amino)piperidin-1-yl)methyl)phenyl)acrylamide (18)

Compound 17 (156 mg, 0.309 mmol) was treated with a solution of TFA (1.36 mL, 18.5 mmol) in DCM (3 mL). The reaction mixture was stirred at RT at for 1 hr, diluted with DCM and treated with sat. NaHCO$_3$ solution (pH 9). The layers were separated. The organic layer was dried over anhydrous Na$_2$SO$_4$, filtered and concentrated. The residue was purified by flash column chromatography, eluent 10% MeOH in DCM (MeOH contained with 2% ammonia). The glass-like product thus obtained was re-dissolved in MeOH, diluted with water. The MeOH was removed in vacuum and the remaining aqueous solution was freeze-dried, to afford title compound 18 (20 mg, 16% yield) as white powder.

$^1$H NMR: 500 MHz, CD$_3$OD, δ (ppm): 7.64 (d, J=16.0 Hz, 1H), 7.56 (bs, 1H), 7.51 (bd, 1H), 7.41-7.37 (m, 2H), 7.26-7.22 (m, 2H), 7.14-7.12 (m, 1H), 7.06-7.04 (m, 2H), 6.46 (d, J=15.7 Hz, 1H), 3.79 (s, 3H), 3.56 (s, 2H), 2.92 (bd, 2H), 2.72-2.66 (m, 1H), 2.35-2.32 (m, 1H), 2.14-2.08 (m, 2H), 1.98-1.90 (m, 3H), 1.54-1.46 (m, 2H), 1.11-1.03 (m, 2H). MS: 405.5 (calcd.), 406.0 (M+H+, found).

Example 4

(E)-N-(Methylsulfonyl)-3-(3-((4-(((trans)-2-phenyl-cyclopropyl)amino)piperidin-1-yl)methyl)phenyl)acrylamide (20)

Scheme 6

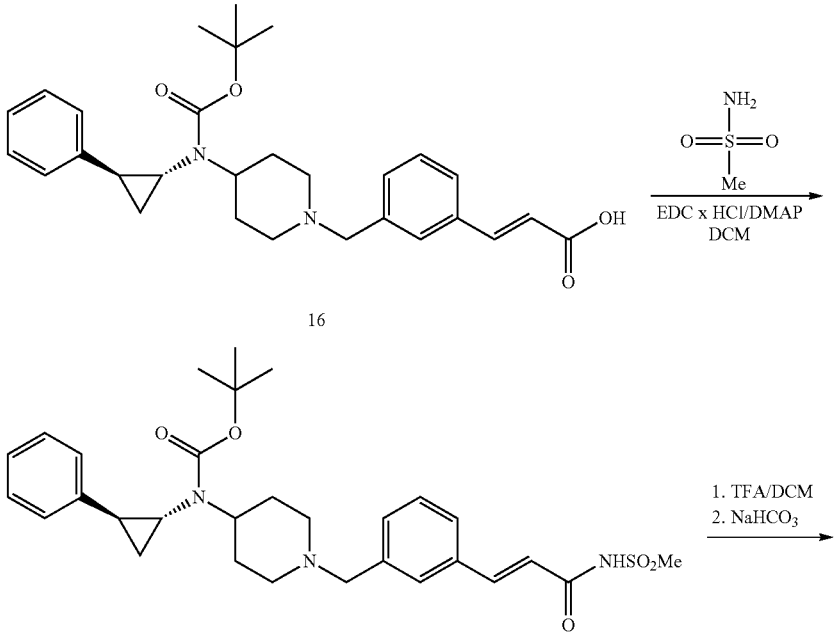

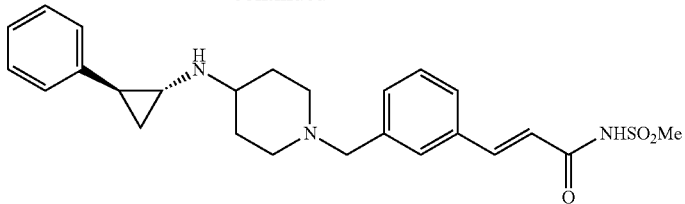

20: Example 4

Step 1. tert-Butyl (1-(3-((E)-3-(methylsulfonamido)-3-oxoprop-1-en-1-yl)benzyl)piperidin-4-yl)((trans)-2-phenylcyclopropyl)carbamate (19)

To a solution of the compound 16 (180 mg, 0.378 mmol) and methylsulfonamide (54 mg, 0.567 mmol) in DCM (6 mL) was added EDC×HCl (145 mg, 0.755 mmol) and DMAP (92 mg, 0.755 mmol) at RT. The reaction mixture was stirred at the same conditions overnight, diluted with more DCM then washed sequentially with a NaHCO₃ solution, water and brine. The organic solution was dried over anhydrous Na₂SO₄, filtered and evaporated. The residue was purified by flash column chromatography, eluent 10% MeOH in DCM (MeOH contained 2% ammonia), to afford title compound 19 (90 mg, 43% yield) as white solid. MS: 553.7 (calcd.), 553.9 (M+H⁺, found).

Step 2. (E)-N-(Methylsulfonyl)-3-(3-((4-(((trans)-2-phenylcyclopropyl)amino) piperidin-1-yl)methyl)phenyl)acrylamide (20)

Compound 19 (90 mg, 0.163 mmol) was treated with a solution of TFA (0.718 mL, 9.75 mol) in DCM (2 mL). The reaction mixture was stirred at RT at for 1 hr, diluted with DCM and treated with sat. NaHCO₃ solution (pH 9). The layers were separated. The organic layer was dried over anhydrous Na₂SO₄, filtered and concentrated. The residue was re-dissolved in MeOH, diluted with water. The MeOH was removed and the remaining aqueous solution was freeze-dried, to afford title compound 20 (27 mg, 37% yield) as white powder.

¹H NMR: 500 MHz, DMSO-d₆, δ (ppm): 7.49 (bs, 1H), 7.46-7.34 (m, 3H), 7.29-7.22 (m, 3H), 7.14-7.11 (m, 1H), 7.06-7.05 (m, 2H), 6.50 (d, J=15.9 Hz, 1H), 3.56 (s, 2H), 2.98 (s, 3H), 2.84 (bd, J=11.6 Hz, 2H), 2.78-2.73 (m, 1H), 2.41-2.38 (m, 1H), 2.10 (bs, 2H), 1.93-1.83 (m, 3H), 1.42 (bs, 2H), 1.09-1.02 (m, 2H). MS: 453.6 (calcd.), 454.0 (M+H⁺, found).

Compounds 21-27 (Examples 5-11) were synthesized starting from compounds 6 or 16 by following the procedures described above for the synthesis of compounds 8 (Example 1, Scheme 2), 10 (Example 2, Scheme 3), 18 (Example 3, Scheme 5) and 20 (Example 4, Scheme 6). Characterization of compounds 21-27 (Examples 5-11) is provided in Table 2.

TABLE 2

Characterization of compounds 21-32 (EXAMPLES 6-12).

| Ex. # | Cpd # | Structure | ¹H NMR |
|---|---|---|---|
| 5 | 21 | (E)-N-Phenoxy-3-(4-((4-(((trans)-2-phenylcyclopropyl)amino)piperidin-1-yl)methyl)phenyl)acrylamide | ¹H NMR: 500 MHz, DMSO-d₆, δ (ppm): 12.23 (bs, 1H), 10.99 (bs, 1H), 9.94 (bs, 2H), 7.72 (d, J = 8.2 Hz, 2H), 7.65-7.62 (m, 3H), 7.36-7.29 (m, 4H), 7.23-7.16 (m, 3H), 7.06-7.03 (m, 3H), 6.74 (d, J = 15.8 Hz, 1H), 4.28 (s, 2H), 3.45 (bd, 3H), 2.99 (bs, 2H), 2.93 (bs, 1H), 2.56-2.51 (m, 1H), 2.28 (bs, 2H), 2.09 (bs, 2H), 1.58-1.53 (m, 1H), 1.32-1.26 (m, 1H). MS: 467.6 (calcd.), 468.0 (M + H⁺, found). |
| 6 | 22 | (E)-N-(Benzyloxy)-3-(4-((4-(((trans)-2-phenylcyclopropyl)amino)piperidin-1-yl)methyl)phenyl)acrylamide | ¹H NMR: 500 MHz, DMSO-d₆, δ (ppm): 11.43 (bs, 1H), 11.01 (bs, 1H), 9.96 (bs, 2H), 7.65-7.62 (m, 4H), 7.54 (d, J = 15.9 Hz, 1H), 7.44-7.34 (m, 5H), 7.31-7.28 (m, 2H), 7.23-7.16 (m, 3H), 6.53 (d, J = 15.9 Hz, 1H), 4.88 (s, 2H), 4.24 (bs, 2H), 3.37 (bs, 2H, obscured by the water signal), 2.92 (bs, 3H), 2.54 (bs, 1H), 2.27 (bs, 3H), 2.08 (bs, 2H), 1.56 (bs, 1H), 1.30-1.25 (m, 1H). MS: 481.6 (calcd.), 482.1 (M + H⁺, found). |

TABLE 2-continued

Characterization of compounds 21-32 (EXAMPLES 6-12).

| Ex. # | Cpd # | Structure | $^1$H NMR |
|---|---|---|---|
| 7 | 23 | 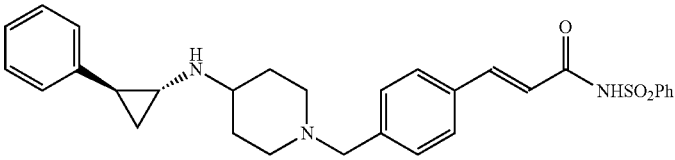<br>(E)-3-(4-((4-(((trans)-2-Phenylcyclopropyl)amino)piperidin-1-yl)methyl)phenyl)-N-(phenylsulfonyl)acrylamide | $^1$H NMR: 500 MHz, DMSO-d$_6$, δ (ppm): 12.43 (bs, 1H), 11.06 (bs, 1H), 9.95 (bs, 2H), 7.99-7.97 (m, 2H), 7.75-7.71 (m, 1H), 7.66-7.63 (m, 6H), 7.59 (d, J = 15.9 Hz, 1H), 7.31-7.28 (m, 2H), 7.23-7.16 (m, 3H), 6.71 (d, J = 15.9 Hz, 1H), 4.26 (s, 2H), 3.42 (bd, 2H), 2.97 (bs, 2H), 2.92 (bs, 1H), 2.54 (bs, 1H), 2.27 (bs, 2H), 2.09 (bs, 2H), 1.55 (bs, 1H), 1.30-1.23 (m, 2H).<br>MS: 515.7 (calcd.), 515.9 (M + H$^+$, found). |
| 8 | 24 | 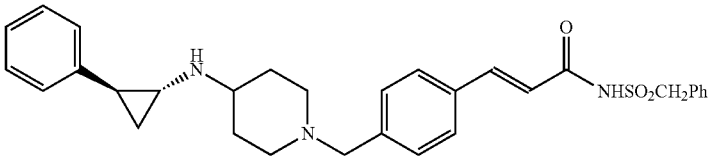<br>(E)-N-(Benzylsulfonyl)-3-(4-((4-(((trans)-2-phenylcyclopropyl)amino)piperidin-1-yl)methyl)phenyl)acrylamide | $^1$H NMR: 500 MHz, DMSO-d$_6$, δ (ppm): 11.81 (bs, 1H), 11.02 (bs, 1H), 9.90 (bs, 2H), 7.77 (d, J = 15.8 Hz, 1H), 7.70-7.65 (m, 4H), 7.42-7.36 (m, 3H), 7.33-7.29 (m, 4H), 7.24-7.16 (m, 3H), 6.67 (d, J = 15.9 Hz, 1H), 4.79 (s, 2H), 4.28 (bs, 2H), 3.43 (bd, 3H), 2.98 (bs, 2H), 2.93 (bs 1H), 2.55-2.52 (m, 1H), 2.27 (bs, 2H), 2.08 (bs, 2H), 1.57-1.53 (m, 1H), 1.30-1.26 (m, 1H),<br>MS: 529.7 (calcd.), 530.0 (M + H$^+$, found). |
| 9 | 25 | 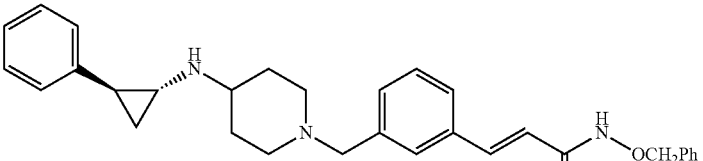<br>(E)-N-(Benzyloxy)-3-(3-((4-(((trans)-2-phenylcyclopropyl)amino)piperidin-1-yl)methyl)phenyl)acrylamide | $^1$H NMR: 500 MHz, CD$_3$OD, δ (ppm): 7.63 (d, J = 15.8 Hz, 1H), 7.55 (bs, 1H), 7.49-7.47 (m, 3H), 7.43-7.37 (m, 5H), 7.28-7.23 (m, 2H), 7.15-7.12 (m, 1H), 7.06-7.05 (m, 2H), 6.45 (d, J = 15.9 Hz, 1H), 4.96 (s, 2H), 3.56 (s, 2H), 2.91 (d, J = 11.9 Hz, 2H), 2.71-2.65 (m, 1H), 2.35-2.32 (m, 1H), 2.14-2.08 (m, 2H), 1.97-1.89 (m, 3H), 1.53-1.46 (m, 2H), 1.10-1.00 (m, 2H).<br>MS: 481.6 (calcd.), 482.0 (M + H$^+$, found). |
| 10 | 26 | 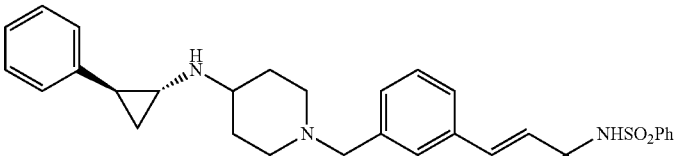<br>(E)-3-(3-((4-(((trans)-2-Phenylcyclopropyl)amino)piperidin-1-yl)methyl)phenyl)-N-(phenylsulfonyl)acrylamide | $^1$H NMR: 500 MHz, CD$_3$OD, δ (ppm): 8.03-8.00 (m, 2H), 7.58-7.37 (m, 8H), 7.29-7.26 (m, 2H), 7.20-7.16 (m, 1H), 7.11-7.09 (m, 2H), 6.58 (d, J = 15.9 Hz, 1H), 3.93 (s, 2H), 3.23 (bd, J = 12.1 Hz, 2H), 3.10-3.06 (m, 1H), 2.65-2.54 (m, 3H), 2.14-2.08 (m, 3H), 1.72-1.65 (m, 2H), 1.26-1.21 (m, 2H).<br>MS: 515.7 (calcd.), 515.9 (M + H$^+$, found). |
| 11 | 27 | 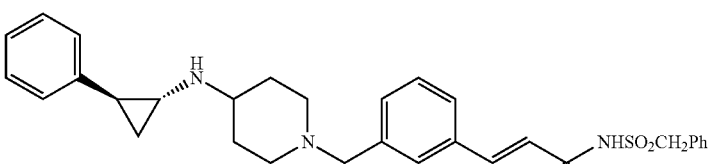<br>(E)-N-(Benzylsulfonyl)-3-(3-((4-(((trans)-2-phenylcyclopropyl)amino)piperidin-1-yl)methyl)phenyl)acrylamide | $^1$H NMR: 500 MHz, CD$_3$OD, δ (ppm): 7.65-7.57 (m, 3H), 7.47-7.39 (m, 4H), 7.36-7.26 (m, 5H), 7.21-7.18 (m, 1H), 7.12-7.10 (m, 2H), 6.56 (d, J = 15.8 Hz, 1H), 4.66 (s, 2H), 3.96 (s, 2H), 3.25 (bd, J = 12.4 Hz, 2H), 3.17-3.11 (m, 1H), 2.62 (bs, 3H), 2.18-2.12 (m, 3H), 1.78-1.70 (m, 2H), 1.32-1.21 (m, 2H).<br>MS: 529.7 (calcd.), 530.0 (M + H$^+$, found). |

Example 12

N-trans-2-phenylcyclopropyl)-1-(4-((E)-styryl)benzyl)piperidin-4-amine (32)

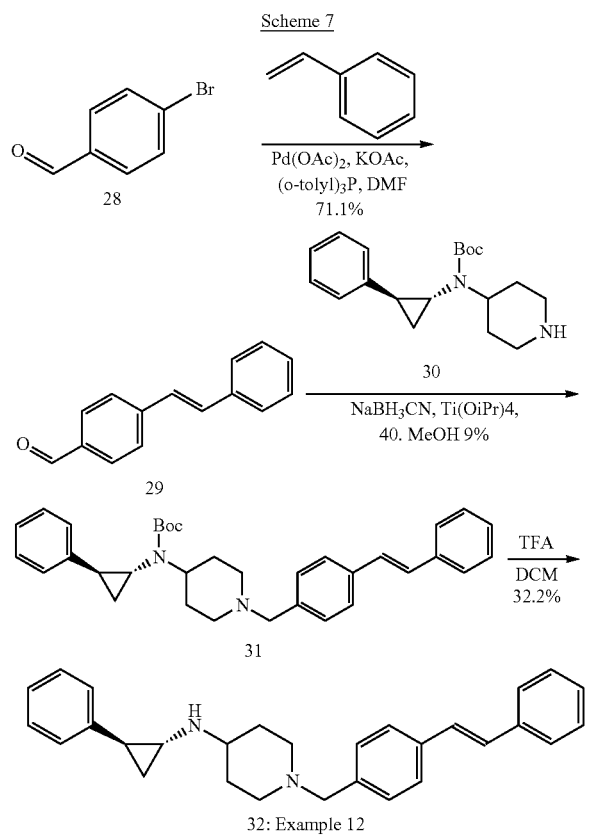

Step 1: (E)-4-styrylbenzaldehyde (29)

To a mixture of 4-bromobenzaldehyde (1.00 g, 5.40 mmol, 1.00 eq) and styrene (1.12 g, 10.8 mmol, 2.00 eq) in DMF (15.0 mL) was added KOAc (583 mg, 5.94 mmol, 1.10 eq) and tri-o-tolylphosphine (164 mg, 540 umol, 0.10 eq), Pd(OAc)$_2$ (60.6 mg, 270 umol, 0.05 eq), and the reaction was stirred at 120° C. for 18 hour under N$_2$. After completion, the reaction mixture was added to water (30 mL), extracted with EtOAc (2×30 mL). The combined organic layers were dried over Na$_2$SO$_4$, filtered and concentrated. The residue was purified by column chromatography (petroleum ether/ethyl acetate=20/1-0/1). The product 20 (800 mg, 3.84 mmol, 71.1% yield) was obtained as a yellow solid.

$^1$H NMR (400 MHz, chloroform-d) δ, 10.02 (s, 1H), 7.90 (d, J=8.0 Hz, 2H), 7.69 (d, –(d, J=16.0 Hz, 1H).

Step 2. tert-butyl trans-2-phenylcyclopropyl)(1-(4-((E)-styryl)benzyl)piperidin-4-yl)carbamate (31)

To a mixture of 20 (200 mg, 960 umol, 1.00 eq) and tert-butyl N-[trans-2-phenylcyclopropyl]-N-(4-piperidyl)carbamate, 30, (304 mg, 960 umol, 1.00 eq) in MeOH (10.0 mL) was added Ti(O$^i$Pr)$_4$ (2.73 g, 9.60 mmol, 2.84 mL, 10.0 eq). The mixture was stirred at 15° C. for 0.5 hr, then cooled to −10° C. NaBH$_3$CN (181 mg, 2.88 mmol, 3.00 eq) was added in portions, then the reaction mixture was stirred at −10~15° C. for 11.5 hr. After completion, the reaction was quenched with water (10 mL), then filtered. The filtrate was concentrated, the residual aqueous solution was extracted with EtOAc (3×15 mL), the combined organic layers were dried over Na$_2$SO$_4$, filtered and concentrated. The residue was purified by column chromatography (petroleum ether/ethyl acetate=10/1~0/1). The product 31 (200 mg, 393 umol, 40.9% yield) was obtained as a yellow oil.

$^1$H NMR (400 MHz, chloroform-d) δ, 7.42 (d, J=7.6 Hz, 2H), 7.39 (d, J=8.0 Hz, 2H), 7.32-7.19 (m, 7H), 7.17-7.08 (m, 1H), 7.06-7.00 (m, 4H), 3.72-3.60 (m, 1H), 3.46-3.33 (m, 2H), 2.92-2.80 (m, 2H), 2.52-2.44 (m, 1H), 2.11-1.82 (m, 5H), 1.73-1.57 (m, 2H), 1.39-1.27 (m, 10H), 1.17-1.12 (m, 1H)

Step 3. N-trans-2-phenylcyclopropyl)-1-(4-((E)-styryl)benzyl)piperidin-4-amine (32)

To a mixture of 31 (200 mg, 393 umol, 1.00 eq) in DCM (750 uL) was added TFA (1.12 g, 9.83 mmol, 727 uL, 25.0 eq), then the mixture was stirred at 15° C. for 1 hour. After completion, the reaction was concentrated, and the residue was dissolved in CH$_3$CN (5 mL), adjusted to pH-7 with Na$_2$CO$_3$ solid, then filtered, and concentrated. The residue was purified by Prep-HPLC (Instrument: GX-I; Column: YMC-Actus ODS-AQ 150*30 5 u; Condition: water (0.1% TFA)-ACN; Begin B: 25; End B: 55; Gradient Time (min): 9; 100% B Hold Time (min): 2; FlowRate (ml/min): 25), the obtained eluent was concentrated to remove organic solvent, and dried under lyophilization to give 32 (82.0 mg, 126.7 umol, 32.2% yield, 98.4% purity, 2TFA) as a white solid.

$^1$H NMR (400 MHz, methanol-d$_4$) δ, 7.69 (d, J=8.0 Hz, 2H), 7.57 (d, J=7.6 Hz, 2H), 7.49 (d, J=8.0 Hz, 2H), 7.40-7.12 (m, 10H), 4.34 (s, 2H), 3.63 (d, J=10.0 Hz, 3H), 3.15-3.04 (m., 2H), 2.97-2.94 (m, 1H), 2.49-2.26 (m, 3H), 2.11-1.81 (m., 2H), LCMS [M+1]: 409.

Example 13

N-(trans-2-phenylcyclopropyl)-1-(3-((E)-styryl)benzyl)piperidin-4-amine (36)

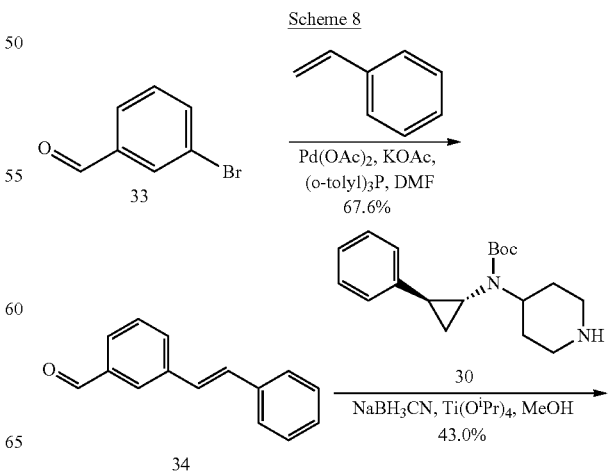

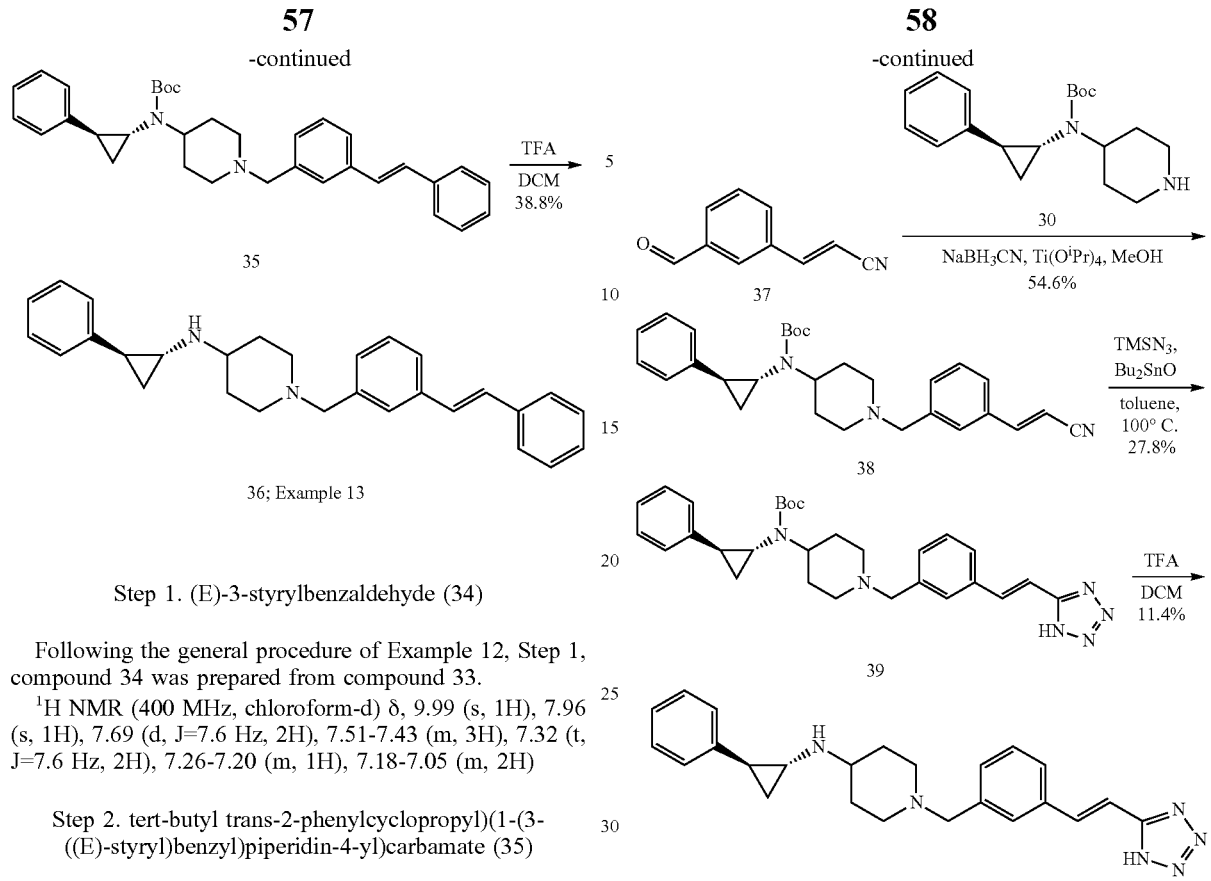

Step 1. (E)-3-styrylbenzaldehyde (34)

Following the general procedure of Example 12, Step 1, compound 34 was prepared from compound 33.

$^1$H NMR (400 MHz, chloroform-d) δ, 9.99 (s, 1H), 7.96 (s, 1H), 7.69 (d, J=7.6 Hz, 2H), 7.51-7.43 (m, 3H), 7.32 (t, J=7.6 Hz, 2H), 7.26-7.20 (m, 1H), 7.18-7.05 (m, 2H)

Step 2. tert-butyl trans-2-phenylcyclopropyl)(1-(3-((E)-styryl)benzyl)piperidin-4-yl)carbamate (35)

Following the general procedure of Example 12, step 2, compound 35 was prepared from compound 34. 1H NMR (400 MHz, chloroform-d) δ, 7.55-7.51 (m, 3H), 7.48-7.34 (m, 6H), 7.33-7.28 (m, 2H), 7.19-7.10 (m, 5H), 3.81-3.67 (m, 1H), 3.54-3.47 (m, 2H), 3.03-2.89 (m, 2H), 2.60-2.50 (m, 1H), 2.19-1.90 (m, 5H), 1.80-1.70 (m, 2H), 1.46-1.37 (m, 10H), 1.27-1.23 (m, 1H).

Step 3. N-trans-2-phenylcyclopropyl)-1-(3-((E)-styryl)benzyl)piperidin-4-amine (36)

Following the general procedure of Example 12, step 3, compound 36 was prepared from compound 35.

$^1$H NMR (400 MHz, methanol-d$_4$) δ, 7.77-7.69 (m, 2H), 7.59 (d, J=7.6 Hz, 2H), 7.51 (t, J=7.6 Hz, 1H), 7.43-7.22 (m, 11H), 4.39 (s, 2H), 3.71-3.66 (m, 3H), 3.22-3.14 (m, 2H), 3.02-2.98 (m, 1H), 2.53-2.35 (m, 3H), 2.16-1.96 (m, 2H), 1.59-1.41 (m, 2H). LCMS [M+1]: 409.

Example 14

1-(3-((E)-2-(1H-tetrazol-5-yl)vinyl)benzyl)-N-trans-2-phenylcyclopropyl)piperidin-4-amine (40)

Scheme 9

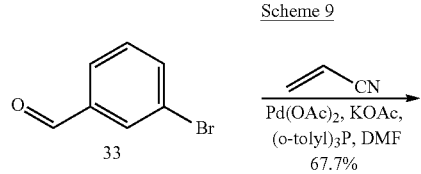

Step 1. (E)-3-(3-formylphenyl)acrylonitrile (37)

To a mixture of 3-bromobenzaldehyde (2.00 g, 10.8 mmol, 1.26 mL, 1.00 eq) and prop-2-enenitrile (1.15 g, 21.6 mmol, 1.43 mL, 2.00 eq) in DMF (30.0 mL) was added AcOK (1.17 g, 11.9 mmol, 1.10 eq) and Pd(OAc)$_2$ (121 mg, 541 umol, 0.05 eq), tris-o-tolylphosphane (329 mg, 1.08 mmol, 0.10 eq), and the reaction was stirred at 120° C. for 18 hours under N$_2$. The reaction was added water (30 mL), extrated with EtOAc (2×30 mL), the combined organic layers were dried over Na$_2$SO$_4$, filtered and concentrated. The residue was purified by column chromatography (PE/EtOAc=20/1-PE/EtOAc=10/1). The 37 (1.15 g, 7.32 mmol, 67.7% yield, 99.2% purity) was obtained as a white solid.

$^1$H NMR (400 MHz, chloroform-d) δ δ, 10.08 (s, 1H), 8.24-8.16 (m, 1H), 8.02-7.93 (m, 2H), 7.73 (d, J=7.6 Hz, 1H), 7.69-7.59 (m, 1H), 7.49 (d, J=16.4 Hz 1H), 6.03 (d, J=16.8 Hz, 1H). LCMS [M+1]: 158.

Step 2. tert-butyl (1-(3-((E)-2-cyanovinyl)benzyl)piperidin-4-yl) trans-2-phenylcyclopropyl)carbamate (38)

To the mixture of 37 (248 mg, 1.58 mmol, 1.00 eq) 30 (500 mg, 1.58 mmol, 1.00 eq) in MeOH (10.0 mL) was added Ti(O$^i$Pr)$_4$ (4.49 g, 15.8 mmol, 4.68 mL, 10.0 eq), and the mixture was stirred at 15° C. for 0.5 hour. The reaction was cooled to −10° C., and NaBH$_3$CN (298 mg, 4.74 mmol, 3.00 eq) was added to the mixture in portions, and the reaction was stirred at −10~15° C. for 3.5 hours. After completion, the reaction was quenched with water (10 mL)

then filtered. The filtrate was extracted with DCM (3×15 mL), the combined organic layers were dried over Na$_2$SO$_4$, filtered and concentrated. The residue was purified by column chromatography (PE/EtOAc=40/1-PE/EtOAc=10/1). The 38 (420 mg, 863 umol, 54.6% yield, 94.0% purity) was obtained as a yellow oil. LCMS [M+1]: 458.

Step 3. tert-butyl (1-(3-((E)-2-(1H-tetrazol-5-yl)vinyl)benzyl)piperidin-4-yl) trans-2-phenylcyclopropyl)carbamate (39)

To a mixture of 38 (100 mg, 219 umol, 1.00 eq) in toluene (3.00 mL) was added TMSN$_3$ (50.4 mg, 437 umol, 57.2 uL, 2.00 eq) and Bu$_2$SnO (500 mg, 2.00 mmol, 9.15 eq), then the mixture was stirred at 100° C. for 24 hours. The reaction mixture was added to water (5 mL) and extracted with DCM (3×5 mL). The combined organic layers were dried over Na$_2$SO$_4$, filtered and concentrated. The residue was purified by Prep-TLC (DCM/MeOH=5/1). The 39 (70.0 mg, 134 umol, 27.8% yield, 95.5% purity) was obtained as a brown solid. LCMS [M+1]: 501; LCMS [M-55]: 445.

Step 4. 1-(3-((E)-2-(1H-tetrazol-5-yl)vinyl)benzyl)-N-trans-2-phenylcyclopropyl)piperidin-4-amine (40)

A mixture 39 (60.0 mg, 120 umol, 1.00 eq) in TFA (500 uL) was stirred at 15° C. for 1 hour. After completion, the reaction was concentrated, and the residue was adjusted to pH 7~8 with NaHCO$_3$ solid, then the mixture was added to water (10 mL), extracted with DCM (3×10 mL). The combined organic layers were dried over Na$_2$SO$_4$, filtered and the filtrate was concentrated. The residue was purified by Prep-HPLC ((Instrument: GX-A; Column: Phenomenex Gemini 150*25 mm*10 um; Condition: water (0.05% ammonia hydroxide v/v)-ACN; Begin B: 17; End B: 37; Gradient Time (min): 15; 100% B Hold Time (min): 2; FlowRate (ml/min): 25), the obtained product was concentrated, and dried under lyophilization. The product 40 (5.50 mg, 13.6 umol, 11.4% yield, 99.1% purity) was obtained as a yellow solid.

$^1$H NMR (400 MHz, methanol-d$_4$) δ, 7.69-7.60 (m, 2H), 7.58-7.51 (m, 1H), 7.46-7.41 (m, 1H), 7.37-7.31 (m, 1H), 7.30-7.22 (m, 2H), 7.20-7.13 (m, 1H), 7.10-7.08 (m, 2H), 3.97 (s., 2H), 3.26-3.23 (m, 2H), 3.04-3.01 (m, 1H), 2.73-2.45 (m, 3H), 2.22-2.01 (m, 3H), 1.75-1.61 (m, 2H), 1.40-1.36 (m, 1H), 1.25-1.12 (m, 2H). LCMS [M+1]: 401.

Example 15

(E)-N-(Methylsulfonyl)-3-(4-((4-(((1R,2S)-2-phenylcyclopropyl)amino)piperidin-1-yl)methyl)phenyl)acrylamide, di-hydrochloride (45)

Scheme 10

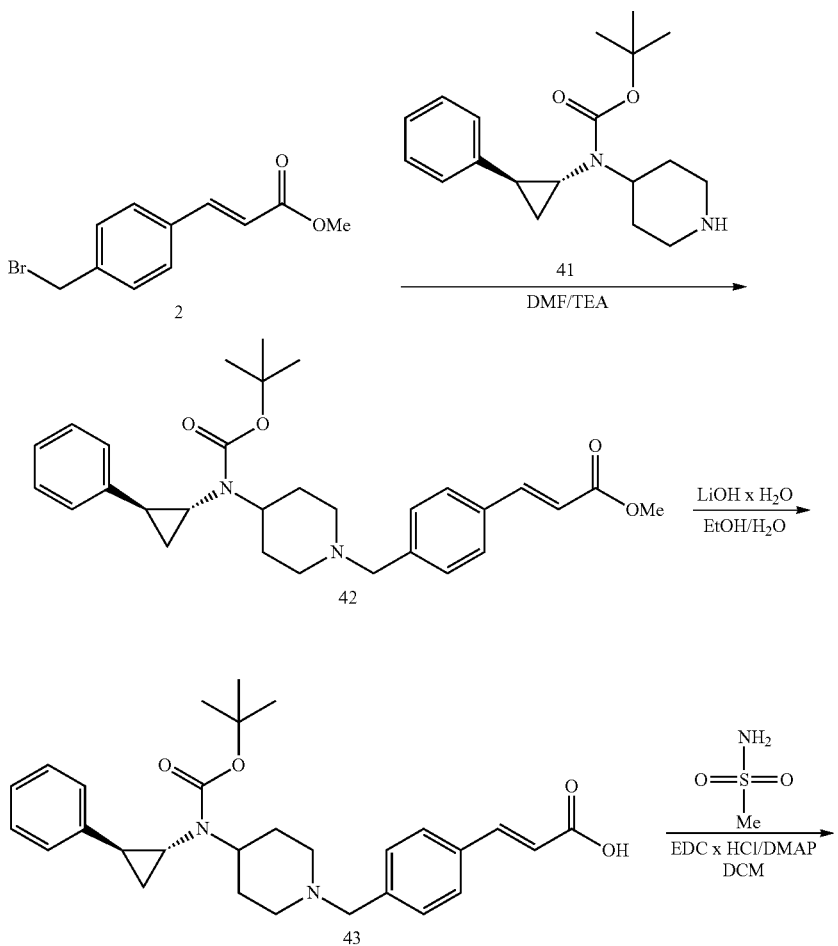

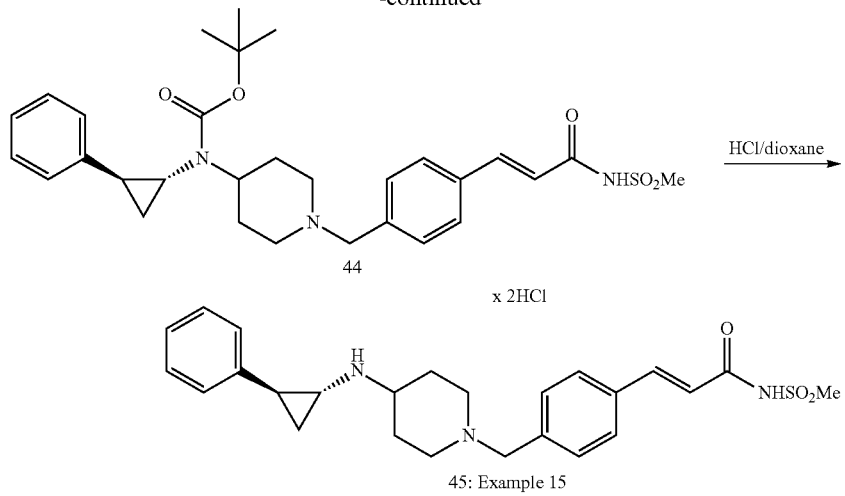

Step 1. (E)-Methyl 3-(4-((4-((tert-butoxycarbonyl)((1R,2S)-2-phenylcyclopropyl)amino)piperidin-1-yl)methyl)phenyl)acrylate (42)

To a solution of bromide 2 (0.733 g, 2.87 mmol) and tert-butyl ((1R,2S)-2-phenylcyclopropyl)(piperidin-4-yl)carbamate (41, 1.00 g, 3.16 mmol) in DMF (10 mL) was added TEA (1.0 mL, 2.50 mmol). The reaction mixture was stirred at RT for 4.5 hrs, treated with brine and extracted with EA. The extract was washed twice with brine, dried over $Na_2SO_4$, filtered and concentrated. The honey-like residue was subjected to flash column chromatography, eluent EA-hexanes (4:1) to afford title compound 42 (1.12 g, 79% yield) as honey-like material. $^1$H NMR, 500 MHz, MeOD, δ (ppm): 7.71 (d, J=16.0 Hz, 1H), 7.59 (d, J=8.1 Hz, 2H), 7.40 (d, J=8.2 Hz, 2H), 7.30-7.26 (m, 2H), 7.19-7.13 (m, 3H), 6.55 (d, J=16.0 Hz, 1H), 3.81 (s, 3H), 3.73-3.66 (m, 1H), 3.55 (s, 2H), 3.00-2.93 (m, 2H), 2.63-2.60 (m, 1H), 2.20-1.98 (m, 5H), 1.81-1.77 (m, 1H), 1.74-1.70 (m, 1H), 1.45-1.40 (m, 10H), 1.28-1.24 (m, 1H). MS: 490.6 (calcd.), 491.2 (M+H$^+$, found).

Step 2. (E)-3-(4-((4-((tert-Butoxycarbonyl)((1R,2S)-2-phenylcyclopropyl)amino)piperidin-1-yl)methyl)phenyl)acrylic acid (43)

To a solution of the ester 42 (1.12 g, 2.28 mmol) in 70% aqueous EtOH (35 mL) was added a hazy solution of LiOH monohydrate (0.479 g, 11.4 mmol) in 20 mL water. The reaction mixture was stirred at rt for 2.5 hrs, acidified to pH 5-6 by addition of 1 N HCl solution then evaporated to its maximum. The oily residue was treated with brine and extracted with DCM. The extract was dried over anhydrous $Na_2SO_4$, filtered and the filtrate was evaporated to form foam which was dried in vacuum to afford title compound 43 (1.11 g, quantitative yield). MS: 476.6 (calcd.), 477.0 (M+H$^+$, found). The material was taken to the next step with no additional purification.

Step 3. tert-Butyl (1-(4-((E)-3-(methylsulfonamido)-3-oxoprop-1-en-1-yl)benzyl)piperidin-4-yl)((1R,2S)-2-phenylcyclopropyl)carbamate (44)

To a solution of the acid 43 (0.700 g, 1.48 mmol) and methanesulfonamide (210 mg, 2.20 mmol) in DCM (10 mL) was added EDCxHCl (560 mg, 2.94 mmol) and DMAP (360 mg, 2.94 mmol) at RT. The reaction mixture was stirred under the same conditions overnight, diluted with more DCM then washed with a $NaHCO_3$ solution (the saturated $NaHCO_3$ solution was diluted with the same amount of water), water and brine. The organic phase was dried over $Na_2SO_4$, filtered and evaporated. The residue was purified by flash column chromatography, eluent 5, then 10% MeOH in DCM (MeOH contained 2% ammonia) to afford title compound 44 (290 mg, 36% yield) as fluffy solid. $^1$H NMR, 500 MHz, MeOD, δ (ppm): 7.57 (d, J=8.1 Hz, 2H), 7.45-7.42 (m, 3H), 7.26-7.22 (m, 2H), 7.18-7.10 (m, 3H), 6.54 (d, J=15.9 Hz, 1H), 4.00 (s, 2H), 3.84-3.77 (m, 1H), 3.35-2.33 (m, 2H), 3.13 (s, 3H), 2.77-2.72 (m, 2H), 2.68-2.65 (m, 1H), 2.43-2.34 (m, 1H), 2.29-2.21 (m, 1H), 2.16-2.10 (m, 1H), 1.96-1.89 (m, 2H), 1.43-1.38 (m, 10H), 1.25-1.21 (m, 1H). MS: 553.7 (calcd.), 554.0 (M+H$^+$, found).

Step 4. (E)-N-(Methylsulfonyl)-3-(4-((4-(((1R,2S)-2-phenylcyclopropyl)amino)piperidin-1-yl)methyl)phenyl)acrylamide, di-hydrochloride (45)

To a suspension of the compound 44 (290 mg, 0.52 mmol) in dioxane (3 mL) at rt was added a 4M solution of HCl in dioxane (6 mL). The reaction mixture was stirred at ambient temperature for 2 hrs and evaporated to dryness. The solid yellowish residue was dissolved in a minimal amount of MeOH then co-precipitated with EA. The precipitate was collected by filtration, washed with EA and dried to afford title compound 45 (252 g, 91% yield) as yellowish solid. $^1$H NMR: 500 MHz, DMSO-d$_6$, δ (ppm): 11.99 (bs, 1H), 11.02 (bs, 1H), 9.899 (bs, 2H), 7.73-7.65 (m, 5H), 7.31-7.28 (m, 2H), 7.24-7.16 (m, 3H), 6.74 (d, J=15.9 Hz, 1H), 4.28 (s, 2H), 3.43 (bs, 3H), 3.32 (s, 3H), 2.98 (bs, 1H), 2.94 (bs, 2H), 2.53 (bs, 1H), 2.27 (bs, 2H), 2.07 (bs, 2H), 1.55-1.53 (m, 1H), 1.30-1.26 (m, 1H). MS: 453.6 (calcd.), 454.1 (M+H$^+$, found).

Compounds 46-49 (examples 16-20) were synthesized starting from compound 43 by following the procedures described above for the synthesis of compound 45 (example 15, scheme 10). Compound 50 (example 20) was synthesized starting from compound 6 by following the procedures described above for the synthesis of compound 49 (example 19). Characterization of compounds 46-50 (examples 16-20) is provided in the table 2.

TABLE 2

Characterization of compounds 46-50 (examples 16-20).

| Ex. # | Cpd # | Structure | Characterization |
|---|---|---|---|
| 16 | 46 | (E)-N-Methyl-N-(methylsulfonyl)-3-(4-((4-(((1R,2S)-2-phenylcyclopropyl)amino)piperidin-1-yl)methyl)phenyl)acrylamide | $^1$H NMR; 500 MHz, DMSO-$d_6$, δ (ppm): 11.02 (bs, 1H), 9.91 (bs, 2H), 7.83 (d, J = 8.1 Hz, 2H), 7.73-7.64 (m, 3H), 7.35-7.28 (m, 3H), 7.24-7.16 (m, 3H), 4.29 (bs, 2H), 3.46 (s, 3H), 3.43 (bs, 3H), 3.30 (s, 3H), 2.98 (bs, 2H), 2.93 (bs, 1H), 2.55-2.52 (m, 1H), 2.27 (bs, 2H), 2.08 (bs, 2H), 1.58-1.53 (m, 1H), 1.30-1.25 (m, 1H). MS: 467.6 (calcd.), 468.2 (M + H$^+$, found). |
| 17 | 47 | (E)-N-(Isopropylsulfonyl)-3-(4-((4-(((1R,2S)-2-phenylcyclopropyl)amino)piperidin-1-yl)methyl)phenyl)acrylamide | $^1$H NMR; 500 MHz, DMSO-$d_6$, δ (ppm): 11.81 (bs, 1H), 11.00 (bs, 1H), 9.90 (bs, 2H), 7.72-7.65 (m, 5H), 7.31-7.28 (m, 2H), 7.24-7.16 (m, 3H), 6.76 (d, J = 15.9 Hz, 1H), 4.28 (s, 2H), 3.71 (sep, J = 6.9 Hz, 1H), 3.44 (bs, 1H), 3.43 (bs, 2H,), 2.98 (bs, 2H), 2.93 (bs, 1H), 2.55-2.53 (m, 1H), 2.27 (bs, 2H), 2.07 (bs, 2H), 1.57-1.52 (m, 1H), 1.30 (d, J = 6.9 Hz, 6H), 1.26-1.29 (m, 1H). MS: 481.7 (calcd.), 482.2 (M + H$^+$, found). |
| 18 | 48 | (E)-3-(4-((4-(((1R,2S)-2-Phenylcyclopropyl)amino)piperidin-1-yl)methyl)phenyl)-N-(propylsulfonyl)acrylamide | $^1$H NMR; 500 MHz, DMSO-$d_6$, δ (ppm): 11.91 (bs, 1H), 11.11 (bs, 1H), 9.97 (bs, 2H), 7.72-7.68 (m, 5H), 7.31-7.28 (m, 2H), 7.23-7.16 (m, 3H), 6.76 (d, J = 15.9 Hz, 1H), 4.27 (s, 2H), 3.45-3.42 (m, 5H), 2.97 (bs, 2H), 2.93 (bs, 1H), 2.54 (bs, 1H), 2.27 (bs, 2H), 2.09 (bs, 2H), 1.75-1.67 (m, 2H), 1.56 (bs, 1H), 1.29-1.26 (m, 1H), 0.99 (t, J = 7.4 Hz, 3H). MS: 481.7 (calcd.), 482.2 (M + H$^+$, found). |
| 19 | 49 | (E)-N-(Ethylsulfonyl)-3-(4-((4-(((1R,2S)-2-phenylcyclopropyl)amino)piperidin-1-yl)methyl)phenyl)acrylamide | $^1$H NMR; 500 MHz, DMSO-$d_6$, δ (ppm): 11.88 (bs, 1H), 11.02 (bs, 1H), 9.90 (bs, 2H), 7.73-7.65 (m, 5H), 7.31-7.28 (m, 2H), 7.24-7.16 (m, 3H), 6.76 (d, J = 15.9 Hz, 1H), 4.28 (bs, 2H), 3.47-3.43 (m, 5H), 2.98 (bs, 2H), 2.94 (bs 1H), 2.55-2.52 (m, 1H), 2.27 (bs, 2H), 2.07 (bs, 2H), 1.56-1.52 (m, 1H), 1.30-1.26 (m, 1H), 1.24 (t, J = 7.3 Hz, 3H). MS: 467.6 (calcd.), 468.2 (M + H$^+$, found). |
| 20 | 50 | (E)-N-(Ethylsulfonyl)-3-(4-((4-(((trans)-2-phenylcyclopropyl)amino)piperidin-1-yl)methyl)phenyl)acrylamide | $^1$H NMR; 500 MHz, DMSO-$d_6$, δ (ppm): 11.88 (bs, 1H), 10.97 (bs, 1H), 9.87 (bs, 2H), 7.73-7.65 (m, 5H), 7.32-7.29 (m, 2H), 7.23-7.16 (m, 3H), 6.75 (d, J = 15.9 Hz, 1H), 4.28 (bs, 2H), 3.47-3.43 (m, 5H), 2.98 (bs, 2H), 2.94 (bs 1H), 2.54-2.52 (m, 1H), 2.27 (bs, 2H), 2.07 (bs, 2H), 1.56-1.52 (m, 1H), 1.31-1.26 (m, 1H), 1.24 (t, J = 7.4 Hz, 3H). MS: 467.6 (calcd468.2 (M + H$^+$, found). |

Intermediate Compound 55

4-((4-((tert-Butoxycarbonyl)((trans)-2-phenylcyclopropyl)amino)piperidin-1-yl)methyl)benzoic acid (55)

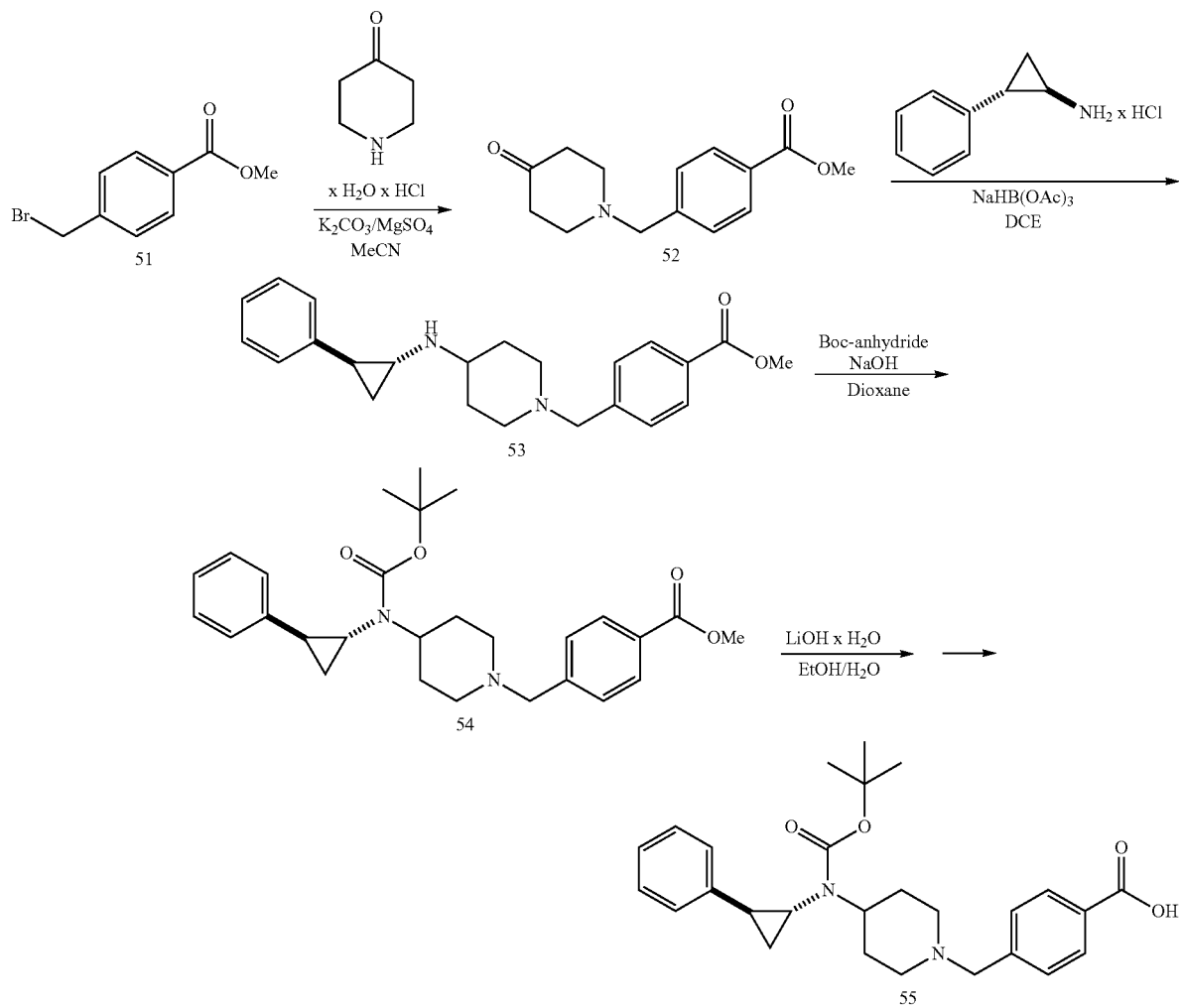

Scheme 11

Step 1. Methyl 4-((4-oxopiperidin-1-yl)methyl)benzoate (52)

A suspension of methyl 4-(bromomethyl)benzoate (51) (3.0 g, 13.10 mmol), 4-piperidone hydrochloride monohydrate (3.02 g, 19.6 mmol), K$_2$CO$_3$ (7.24 g, 52.4 mmol) and anhydrous MgSO$_4$ (3.15 g 26.2 mmol) in MeCN (90 mL) was stirred at reflux conditions for 2 hrs. The mixture was cooled to RT, filtered and the filtrate was evaporated to yield an oil. The material was purified by flash column chromatography, eluent EA, to afford title compound 52 (2.82 g, 87% yield) as a white solid. MS: 247.3 (calcd.), 248.2 (M+H$^+$, found).

Step 2. Methyl 4-((4-(((trans)-2-phenylcyclopropyl)amino)piperidin-1-yl)methyl)benzoate (53)

A suspension of ketone 52 (2.82 g, 11.40 mmol) and (trans)-2-phenylcyclopropanamine hydrochloride (2.33 g, 13.73 mmol) in dichloroethane (35 mL) was stirred at RT for 2 hr, cooled to 0° C. then treated with sodium triacetoxyborohydride (5.24 g, 27.72 mmol). The mixture was stirred at 0° C. for 2 hr then allowed to warm to RT and stirred for an additional 12 hrs. The reaction mixture was then diluted with a mixture of conc. NaHCO$_3$ solution and 0.5 N NaOH (pH 9-9.5) and extracted with DCM. The extract was dried over anhydrous MgSO$_4$, filtered, concentrated and purified by flash column chromatography, eluent 5% MeOH then 10% MeOH in DCM (MeOH contained 2% ammonia) to produce title compound 53 (3.57 g. 71% yield) as sticky oil.

$^1$H NMR: 500 MHz, CDCl$_3$, δ (ppm): 7.98 (d, J=8.4 Hz, 2H), 7.39 (d, J=8.5 Hz, 2H), 7.26-7.22 (m, 2H), 7.15-7.12 (m, 1H), 7.02-7.00 (m, 2H), 3.90 (s, 3H), 3.52 (s, 2H), 2.80 (bd, J=11.5 Hz, 2H), 2.66-2.61 (m, 1H), 2.35-2.32 (m, 1H), 2.07-2.00 (m, 2H), 1.92-1.84 (m, 3H), 1.47-1.39 (m, 2H), 1.07-1.04 (m, 1H), 1.00-0.96 (m, 1H). MS: 364.5 (calcd.), 365.1 (M+H+, found).

Step 3. Methyl 4-((4-(tert-butoxycarbonyl((trans)-2-phenylcyclopropyl)amino)piperidin-1-yl)methyl)benzoate (54)

A solution of NaOH (830 mg, 20.74 mmol) in water (8 mL) was added to a solution of amine 53 (1.89 g, 5.19 mmol) and Boc-anhydride (3.0 g, 13.75 mmol) in dioxane (40 mL). The reaction mixture was stirred at RT for 22 hrs, diluted with water and extracted with EA. The extract was washed with brine, dried over anhydrous MgSO$_4$, filtered and concentrated. The remaining viscous oil was subjected to flash column chromatography, eluent EA-hexanes (1:1) to afford title compound 54 (2.4 g, 99% yield) as sticky oil. MS: 464.6 (calcd.), 465.0 (M+H+, found).

Step 4. 4-((4-(tert-Butoxycarbonyl((trans)-2-phenyl-cyclopropyl)amino)piperidin-1-yl)methyl)benzoic acid (55)

A solution of LiOH×H$_2$O (0.867 g, 20.66 mmol) in water (12 mL) was added to a solution of ester 54 (2.4 g, 5.17 mmol) in 70% aqueous EtOH (40 mL). The reaction mixture was heated at 80° C. for 3.5 hrs, cooled to RT, acidified to pH 6-6.5 then, partitioned between brine and DCM. During the layer separation a solid was formed between the layers which was collected by filtration and dried to afford the first crop of the title compound 55.

The organic layer was washed with brine, dried over MgSO$_4$, filtered and evaporated to dryness to afford a second crop of the title compound 55 as white foam. Both crops were combined, suspended in DCM and the suspension was evaporated to afford title compound 17 (1.82 g, 78% yield) as a single batch. MS: 450.6 (calcd.), 451.0 (M+H+, found).

Example 21

N-Methoxy-4-((4-(((trans)-2-phenylcyclopropyl)amino)piperidin-1-yl)methyl)benzamide di-hydrochloride (57)

Scheme 12

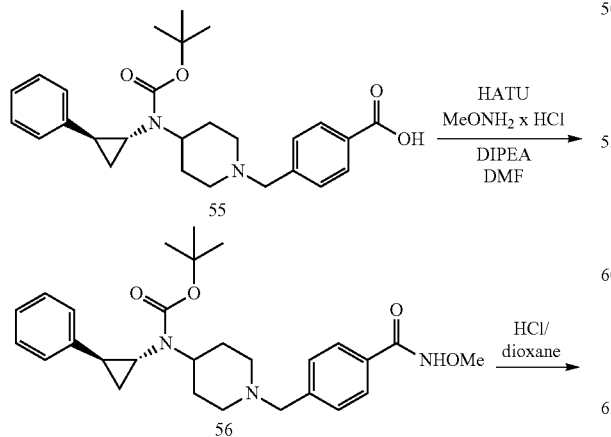

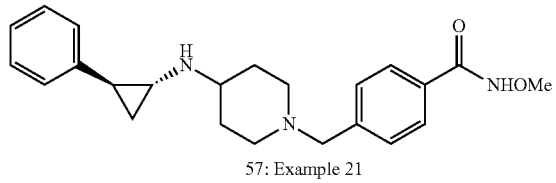

Step 1. tert-Butyl (1-(4-(methoxycarbamoyl)benzyl)piperidin-4-yl)((trans)-2-phenylcyclopropyl)carbamate (56)

A solution of the acid 55 (200 mg, 0.44 mmol), the DIPEA (0.330 mL, 1.91 mmol) and HATU reagent (220 mg, 0.58 mmol) in DMF (4 mL) was stirred for 90 min. To the mixture was added the methoxyamine hydrochloride (110 mg, 1.33 mmol). The combined mixture was stirred at RT overnight, treated with brine. A gummy precipitate was formed which was collected by filtration and dried in vacuum. The material was then subjected to flash column chromatography, eluent hexanes-EA (1:9) to afford title compound 56 (0.164 g, 77% yield) as sticky foam. $^1$H NMR: 500 MHz, MeOD, δ (ppm): 7.45 (d, J=8.4 Hz, 2H), 7.47 (d, J=8.3 Hz, 2H), 7.30-7.27 (m, 2H), 7.20-7.13 (m, 3H), 3.84 (s, 3H), 3.74-3.67 (m, 1H), 3.59 (s, 2H), 3.00-2.93 (m, 2H), 2.64-2.61 (m, 1H), 2.22-1.99 (m, 5H), 1.82-1.78 (m, 1H), 1.75-1.72 (m, 1H), 1.45-1.41 (m, 10H), 1.28-1.24 (m, 1H). MS: 479.6 (calcd.), 480.0 (M+H+, found).

Step 2. N-Methoxy-4-((4-(((trans)-2-phenylcyclopropyl)amino)piperidin-1-yl)methyl)benzamide di-hydrochloride (57)

To a suspension of the compound 56 (160 mg, 0.33 mmol) in dioxane (2 mL) at rt was added a 4M solution of HCl in dioxane (2 ml, 8.00 mmol). The reaction mixture was stirred at ambient temperature for 3 hrs, evaporated to dryness and the resultant white solid was triturated with a mixture of MeOH and acetone, collected by filtration and dried to afford title compound 57 (121 mg, 80% yield) as of-white solid.

$^1$H NMR: 500 MHz, DMSO-d$_6$, δ (ppm): 11.91 (bs, 1H), 11.03 (bs, 1H), 9.93 (bs, 2H), 7.83 (d, J=8.0 Hz, 2H), 7.68 (d, J=7.5 Hz, 2H), 7.31-7.28 (m, 2H), 7.23-7.16 (m, 3H), 4.31 (s, 2H), 3.71 (s, 3H), 3.44 (bs, 2H), 3.42 (bs, 1H), 2.99 (bs, 2H), 2.93 (bs, 1H), 2.53-2.52 (m, 1H), 2.27 (bs, 2H), 2.08 (bs, 2H), 1.57-1.53 (m, 1H), 1.30-1.26 (m, 1H). MS: 379.5 (calcd.), 380.0 (M+H+, found).

Example 22

N-(Methylsulfonyl)-4-((4-(((trans)-2-phenylcyclopropyl)amino)piperidin-1-yl)methyl)benzamide di-hydrochloride (59)

Scheme 13

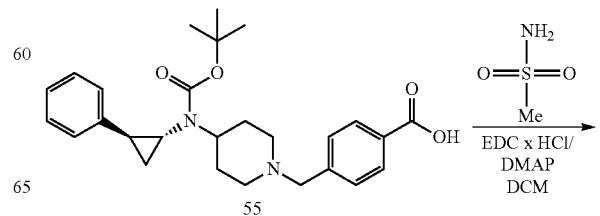

-continued

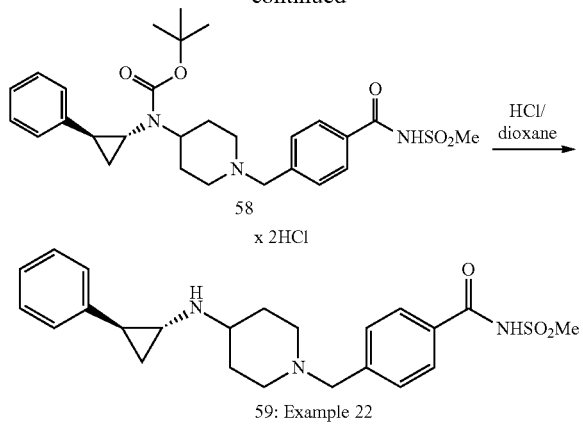

Step 1. tert-Butyl (1-(4-((methylsulfonyl)carbamoyl)benzyl)piperidin-4-yl)((trans)-2-phenylcyclopropyl)carbamate (58)

To a solution of acid 55 (300 mg, 0.67 mmol) and methanesulfonamide (95 mg, 1.00 mmol) in DCM (7 mL) was added EDC×HCl (255 mg, 1.33 mmol) and DMAP (163 mg, 1.33 mmol) at RT. The reaction mixture was stirred under the same conditions overnight, diluted with more DCM then washed with a NaHCO$_3$ solution (the saturated NaHCO$_3$ solution was diluted with the same amount of water), water and brine. The organic phase was dried over Na$_2$SO$_4$, filtered and evaporated. The residue was purified by flash column chromatography, eluent 10, then 15% MeOH in DCM (MeOH contained 2% ammonia) to produce fluffy solid. The material was dissolved in acetone and treated with excess hexanes to form a precipitate which was collected by filtration, washed with hexanes and dried to afford title compound 58 (146 mg, 42% yield). $^1$H NMR: 500 MHz, DMSO-d$_6$, δ (ppm): 7.93 (d, J=8.2 Hz, 2H), 7.39 (d, J=8.2 Hz, 2H), 7.18-7.15 (m, 2H), 7.09-7.02 (m, 3H), 4.11 (s, 1H), 4.04 (bs, 2H), 3.69-3.63 (m, 1H), 3.25 (bs, 2H), 3.00 (s, 3H), 2.78 (bs, 2H), 2.60-2.57 (m, 1H), 2.35-2.27 (m, 1H), 2.21-2.14 (m, 1H), 2.04-2.00 (m, 1H), 1.85-1.80 (m, 2H), 1.31-1.28 (m, 10H), 1.14-1.10 (m, 1H). MS: 527.7 (calcd.), 528.2 (M+H$^+$, found).

Step 2. N-(Methylsulfonyl)-4-((4-(((trans)-2-phenylcyclopropyl)amino)piperidin-1-yl)methyl)benzamide di-hydrochloride (59)

To a suspension of the compound 58 (146 mg, 0.28 mmol) in dioxane (2 mL) at rt was added a 4M solution of HCl in dioxane (2 ml, 8.00 mmol). The reaction mixture was stirred at ambient temperature for 3 hrs, evaporated to dryness and the resultant white solid was triturated with acetone, collected by filtration and dried to afford title compound 59 (119 g, 86% yield) as white solid.

$^1$H NMR: 500 MHz, DMSO-d$_6$, δ (ppm): 12.24 (bs, 1H), 11.08 (bs, 1H), 9.92 (bs, 2H), 8.01 (d, J=8.3 Hz, 2H), 7.74 (bd, 2H), 7.31-7.29 (m, 2H), 7.24-7.17 (m, 3H), 4.33 (s, 2H), 3.43 (bs, 2H), 3.41 (bs, 1H), 3.39 (s, 3H), 2.99 (bs, 2H), 2.94 (bs, 1H), 2.54-2.51 (m, 1H), 2.27 (bs, 2H), 2.08 (bs, 2H), 1.56 (bs, 1H), 1.30-1.28 (m, 1H). MS: 427.6 (calcd.), 428.1 (M+H$^+$, found).

Compounds 60-70 (examples 23-33) were synthesized starting from compound 55 by following the procedures described above for the synthesis of compound 57 (example 21, scheme 12) or compound 59 (example 22, scheme 13). Characterization of compounds 60-70 (examples 23-33) is provided in table 3.

TABLE 3

Characterization of compounds 60-70 (examples 23-33).

| Ex. # | Cpd # | Structure | $^1$H NMR |
|---|---|---|---|
| 23 | 60 | N-(Benzyloxy)-4-((4-(((trans)-2-phenylcyclopropyl)amino)piperidin-1-yl)methyl)benzamide | $^1$H NMR; 500 MHz, DMSO-d$_6$, δ (ppm): 11.93 (bs, 1H), 11.03 (bs, 1H), 9.92 (bs, 2H), 7.82 (d, J = 7.9 Hz, 2H), 7.68 (d, J = 7.6 Hz, 2H), 7.46 (d, J = 7.0 Hz, 2H), 7.42-7.35 (m, 3H), 7.31-7.28 (m, 2H), 7.23-7.16 (m, 3H), 4.93 (s, 2H), 4.30 (bs, 2H), 3.44 (bs, 2H), 3.42 (bs, 1H), 2.99 (bs, 2H), 2.93 (bs, 1H), 2.55-2.52 (m, 1H), 2.27 (bs, 2H), 2.09 (bs, 1H), 2.07 (bs, 1H), 1.57-1.53 (m, 1H), 1.30-1.26 (m, 1H). MS: 455.6 (calcd.), 456.1 (M + H$^+$, found). |
| 24 | 61 | N-Phenoxy-4-((4-(((trans)-2-phenylcyclopropyl)amino)piperidin-1-yl)methyl)benzamide | $^1$H NMR; 500 MHz, DMSO-d$_6$, δ (ppm): 12.66 (bs, 1H), 11.05 (bs, 1H), 9.90 (bs, 2H), 7.96 (d, J = 7.7 Hz, 2H), 7.74 (bd, 2H), 7.37-7.29 (m, 4H), 7.24-7.17 (m, 3H), 7.10-7.04 (m, 3H), 4.34 (bs, 2H), 3.45 (bs, 3H), 3.01 (bs, 2H), 2.94 (bs, 1H), 2.55-2.52 (m, 1H), 2.27 (bs, 2H), 2.09 (bs, 2H), 1.57-1.53 (m, 1H), 1.31-1.27 (m, 1H). MS: 441.6 (calcd.), 442.0 (M + H$^+$, found). |

TABLE 3-continued

Characterization of compounds 60-70 (examples 23-33).

| Ex. # | Cpd # | Structure | ¹H NMR |
|---|---|---|---|
| 25 | 62 | N-(Benzylsulfonyl)-4-((4-(((trans)-2-phenylcyclopropyl)amino)piperidin-1-yl)methyl)benzamide | ¹H NMR; 500 MHz, DMSO-$d_6$, δ (ppm): 12.12 (bs, 1H), 11.07 (bs, 1H), 9.92 (bs, 2H), 7.96 (d, J = 8.3 Hz, 2H), 7.72 (bd, 2H), 7.39-7.30 (m, 7H), 7.24-7.17 (m, 3H), 4.87 (s, 2H), 4.32 (bs, 2H), 3.44 (bs, 2H), 3.42 (bs, 1H), 2.99 (bs, 2H), 2.94 (bs, 1H), 2.54 (bs, 1H), 2.27 (bs, 2H), 2.08 (bs, 2H), 1.57-1.53 (m, 1H), 1.30-1.26 (m, 1H). MS: 503.7 (calcd.), 504.2 (M + H⁺, found). |
| 26 | 63 | N-Methyl-N-(methylsulfonyl)-4-((4-(((trans)-2-phenylcyclopropyl)amino)piperidin-1-yl)methyl)benzamide | ¹H NMR; 500 MHz, DMSO-$d_6$, δ (ppm): 11.11 (bs, 1H), 9.97 (bs, 2H), 7.79-7.70 (m, 4H), 7.31-7.28 (m, 2H), 7.23-7.16 (m, 3H), 4.33 (s, 2H), 3.44 (bs, 6H), 3.18 (s, 3H), 3.00 (bs, 2H), 2.93 (bs, 1H), 2.56-2.52 (m, 1H), 2.29 (bs, 2H), 2.09 (bs, 2H), 1.58-1.54 (m, 1H), 1.29-1.25 (m, 1H). MS: 441.6 (calcd.), 442.2 (M + H⁺, found). |
| 27 | 64 | 4-((4-(((trans)-2-Phenylcyclopropyl)amino)piperidin-1-yl)methyl)-N-(phenylsulfonyl)benzamide | ¹H NMR; 500 MHz, DMSO-$d_6$, δ (ppm): 12.67 (bs, 1H), 11.02 (bs, 1H), 9.90 (bs, 2H), 8.01-8.00 (m, 2H), 7.94 (d, J = 8.3 Hz, 2H), 7.74-7.63 (m, 5H), 7.31-7.28 (m, 2H), 7.23-7.20 (m, 1H), 7.16 (bd, 2H), 4.31 (s, 2H), 3.41 (bs, 3H), 2.96 (bs, 2H), 2.93 (bs, 1H), 2.52 (bs, 1H), 2.25 (bs, 2H), 2.07 (bs, 1H), 2.05 (bs, 1H), 1.56-1.52 (m, 1H), 1.30-1.27 (m, 1H). MS: 489.6 (calcd.), 490.1 (M + H⁺, found). |
| 28 | 65 | N-(Isopropylsulfonyl)-4-((4-(((trans)-2-phenylcyclopropyl)amino)piperidin-1-yl)methyl)benzamide | ¹H NMR; 500 MHz, DMSO-$d_6$, δ (ppm): 12.08 (bs, 1H), 11.09 (bs, 1H), 9.93 (bs, 2H), 8.00 (d, J = 8.3 Hz, 2H), 7.74 (bd, 2H), 7.31-7.28 (m, 2H), 7.24-7.17 (m, 3H), 4.33 (bs, 2H), 3.83 (sep, J = 6.9 Hz, 1H), 3.44 (bs, 2H), 3.42 (bs, 1H), 2.99 (bs, 2H), 2.93 (bs, 1H), 2.54 (bs, 1H), 2.27 (bs, 2H), 2.08 (bs, 2H), 1.55 (bs, 1H), 1.33 (d, J = 6.9 Hz, 6H), 1.30-1.26 (m, 1H). MS: 455.6 (calcd.), 456.2 (M + H⁺, found). |
| 29 | 66 | 4-((4-(((trans)-2-Phenylcyclopropyl)amino)piperidin-1-yl)methyl)-N-(propylsulfonyl)benzamide | ¹H NMR; 500 MHz, DMSO-$d_6$, δ (ppm): 12.17 (bs, 1H), 11.13 (bs, 1H), 9.96 (bs, 2H), 8.00 (d, J = 8.4 Hz, 2H), 7.75 (bd, 2H), 7.31-7.28 (m, 2H), 7.24-7.16 (m, 3H), 4.33 (bs, 2H), 3.51 (t, J = 7.6 Hz, 2H), 3.44 (bs, 2H), 3.42 (bs, 1H), 2.99 (bs, 2H), 2.93 (bs, 1H), 2.54 (bs, 1H), 2.27 (bs, 2H), 2.09 (bs, 2H), 1.77 (sex, J = 7.5 Hz, 2H), 1.56 (bs, 1H), 1.30-1.26 (m, 1H), 1.00 (t, J = 7.4 Hz, 3H). MS: 455.6 (calcd.), 456.2 (M + H⁺, found). |
| 30 | 67 | N-(Ethylsulfonyl)-4-((4-(((trans)-2-phenylcyclopropyl)amino)piperidin-1-yl)methyl)benzamide | ¹H NMR; 500 MHz, DMSO-$d_6$, δ (ppm): 12.13 (bs, 1H), 11.08 (bs, 1H), 9.91 (bs, 2H), 8.01 (d, J = 8.3 Hz, 2H), 7.73 (bd, 2H), 7.31-7.28 (m, 2H), 7.24-7.16 (m, 3H), 4.32 (bs, 2H), 3.52 (q, J = 7.4 Hz, 2H), 3.42 (bs, 2H), 3.41 (bs, 1H), 2.95 (bs, 2H), 2.94 (bs, 1H), 2.54 (bs, 1H), 2.26 (bs, 2H), 2.08 (bs, 2H), 1.56 (bs, 1H), 1.30-1.24 (m, 4H). MS: 441.6 (calcd.), 442.2 (M + H⁺, found). |

TABLE 3-continued

Characterization of compounds 60-70 (examples 23-33).

| Ex. # | Cpd # | Structure | ¹H NMR |
|---|---|---|---|
| 31 | 68 | N-(tert-Butylsulfonyl)-4-((4-(((trans)-2-phenylcyclopropyl)amino)piperidin-1-yl)methyl)benzamide | ¹H NMR; 500 MHz, DMSO-$d_6$, δ (ppm): 11.65 (bs, 1H), 11.09 (bs, 1H), 9.93 (bs, 2H), 7.96 (d, J = 8.3 Hz, 2H), 7.73 (bd, 2H), 7.31-7.28 (m, 2H), 7.23-7.16 (m, 3H), 4.33 (bs, 2H), 3.44 (bs, 2H), 3.42 (bs, 1H), 2.99 (bs, 2H), 2.94 (bs, 1H), 2.54 (bs, 1H), 2.27 (bs, 2H), 2.10 (bs, 2H), 1.57-1.53 (m, 1H), 1.41 (s, 9H), 1.30-1.26 (m, 1H). MS: 469.6 (calcd.), 470.2 (M + H⁺, found). |
| 32 | 69 | 4-((4-(((trans)-2-Phenylcyclopropyl)amino)piperidin-1-yl)methyl)-N-tosylbenzamide | ¹H NMR; 500 MHz, DMSO-$d_6$, δ (ppm): 12.57 (bs, 1H), 11.07 (bs, 1H), 9.94 (bs, 2H), 7.93 (d, J = 8.4 Hz, 2H), 7.89 (d, J = 8.3 Hz, 2H), 7.70 (bd, 2H), 7.44 (d, J = 8.0 Hz, 2H), 7.31-7.28 (m, 2H), 7.23-7.20 (m, 1H), 7.17-7.16 (m, 2H), 4.31 (bs, 2H), 3.41 (bs, 3H), 2.96 (bs, 2H), 2.93 (bs, 1H), 2.53 (bs, 1H), 2.40 (s, 3H), 2.25 (bs, 2H), 2.07 (bs, 2H), 1.55 (bs, 1H), 1.29-1.25 (m, 1H). MS: 503.7 (calcd.), 504.2 (M + H⁺, found). |
| 33 | 70 | N-((4-Fluorophenyl)sulfonyl)-4-((4-(((trans)-2-phenylcyclopropyl)amino)piperidin-1-yl)methyl)benzamide | ¹H NMR; 500 MHz, DMSO-$d_6$, δ (ppm): 12.70 (bs, 1H), 10.98 (bs, 1H), 9.86 (bs, 2H), 8.08-8.05 (m, 2H), 7.94 (d, J = 8.3 Hz, 2H), 7.69 (bd, 2H), 7.51-7.47 (m, 2H), 7.31-7.28 (m, 2H), 7.23-7.20 (m, 1H), 7.16 (bd, 2H), 4.31 (s, 2H), 3.42 (bs, 3H), 2.97 (bs, 2H), 2.93 (bs, 1H), 2.54 (bs, 1H), 2.25 (bs, 2H), 2.04 (bs, 2H), 1.56-1.52 (m, 1H), 1.30-1.26 (m, 1H). MS: 507.7 (calcd.), 508.1 (M + H⁺, found). |

Example 34

N-(Methylsulfonyl)-4-((4-(((1R,2S)-2-phenylcyclopropyl)amino)piperidin-1-yl)methyl)benzamide dihydrochloride (74)

Scheme 14

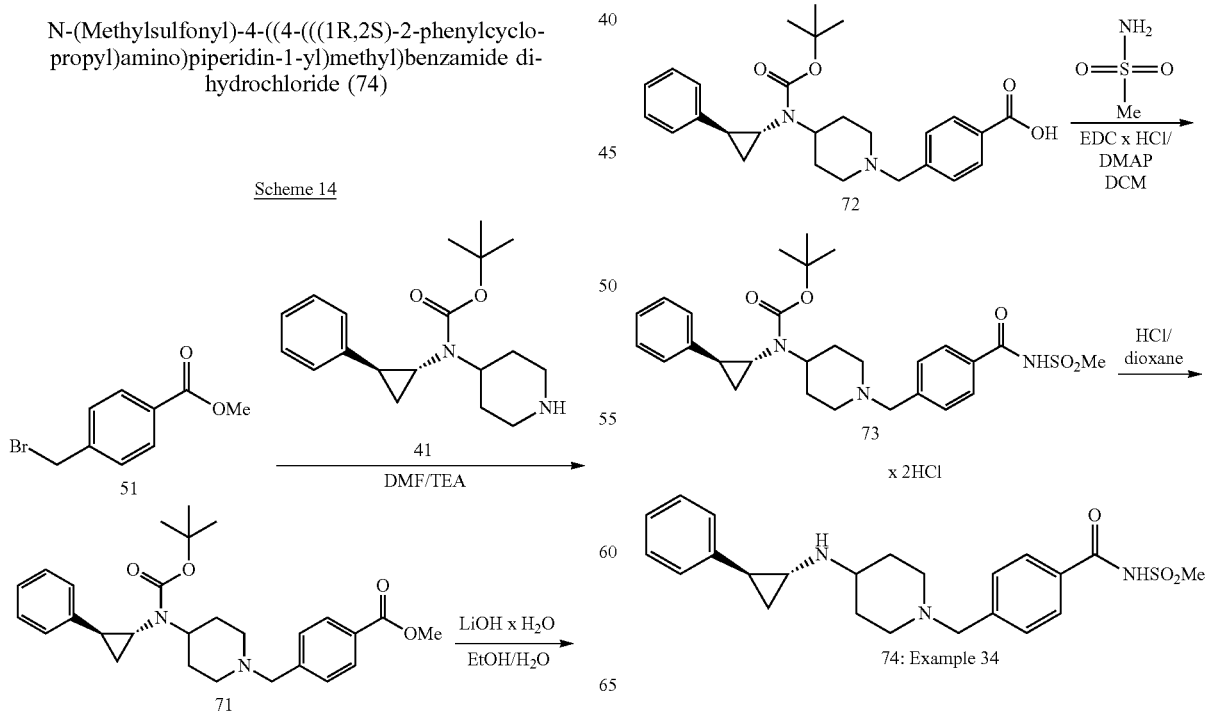

Step 1. Methyl 4-((4-((tert-butoxycarbonyl)((1R, 2S)-2-phenylcyclopropyl)amino)piperidin-1-yl)methyl)benzoate (71)

To a solution of bromide 51 (1.15 g, 5.02 mmol) and tert-butyl ((1R,2S)-2-phenylcyclopropyl)(piperidin-4-yl)carbamate (41, 1.747 g, 5.52 mmol) in DMF (10 mL) was added TEA (1.75 mL, 12.55 mmol). The reaction mixture was stirred at RT for 3 hrs, treated with brine and extracted with EA. The extract was washed twice with brine, dried over Na₂SO₄, filtered and concentrated. The honey-like residue was subjected to flash column chromatography, eluent EA-hexanes (1:1) to afford title compound 71 (1.84 g, 79% yield) as honey-like material.

$^1$H NMR: 500 MHz, MeOD, δ (ppm): 7.97 (d, J=8.5 Hz, 2H), 7.44 (J=8.5 Hz, 2H), 7.27-7.23 (m, 2H), 7.17-7.10 (m, 3H), 3.90 (s, 3H), 3.71-3.64 (m, 1H), 3.57 (s, 2H), 2.98-2.90 (m, 2H), 2.61-2.58 (m, 1H), 2.19-1.97 (m, 5H), 1.79-1.75 (m, 1H), 1.72-1.68 (m, 1H), 1.42-1.38 (m, 10H), 1.24-1.22 (m, 1H). MS: 464.6 (calcd.), 465.2 (M+H⁺, found).

Step 2. 4-((4-((tert-Butoxycarbonyl)((1R,2S)-2-phenylcyclopropyl)amino)piperidin-1-yl)methyl)benzoic acid (72)

To a solution of ester 71 (1.84 g, 3.96 mmol) in 70% aqueous EtOH (40 mL) was added a solution of LiOH×H₂O (426 mg, 10.15 mmol) in water (22 mL). The reaction mixture was stirred at rt for 4.5 hrs, treated with 25 mL of 10% NaH₂PO₄ solution, acidified further to pH 4 with HCl. A white precipitate was formed. The suspension was evaporated to its maximum to remove EtOH. The resultant aqueous suspension was filtered. The white precipitate was collected and dried in vacuum to afford title compound 72 (1.93 g, 108% yield) as white solid. The material was used crude in the next step.

$^1$H NMR: 500 MHz, DMSO-d₆, δ (ppm): 12.83 (bs, 1H), 7.88 (d, J=8.3 Hz, 2H), 7.39 (J=8.2 Hz, 2H), 7.28-7.25 (m, 2H), 7.17-7.11 (m, 3H), 3.57-3.47 (m, 3H), 2.85-2.79 (m, 2H), 2.57-2.54 (m, 1H), 2.08-1.82 (m, 5H), 1.68-1.60 (m, 2H), 1.35-1.30 (m, 10H), 1.24-1.20 (m, 1H). MS: 450.6 (calcd.), 451.2 (M+H⁺, found).

Step 3. tert-Butyl (1-(4-((methylsulfonyl)carbamoyl)benzyl)piperidin-4-yl)((1R,2S)-2-phenylcyclopropyl)carbamate (73)

To a solution of the acid 72 (300 mg, 0.67 mmol) and methanesulfonamide (95 mg, 1.00 mmol) in DCM (6 mL) was added EDC×HCl (255 mg, 1.33 mmol) and DMAP (163 mg, 1.33 mmol) at RT. The reaction mixture was stirred under the same conditions overnight, diluted with more DCM then washed with a NaHCO₃ solution (the saturated NaHCO₃ solution was diluted with the same amount of water), water and brine. The organic phase was dried over Na₂SO₄, filtered and evaporated. The residue was purified by flash column chromatography, eluent 10, then 15% MeOH in DCM (MeOH contained 2% ammonia) to produce a foam. The material was triturated with MeOH and collected by filtration (first crop). During the filtration process a precipitate was formed in the filtrate. The precipitate was combined with the first crop of the product and the combined product was washed with MeOH on the filter and dried to afford title compound 73 (182 mg, 52% yield). MS: 527.7 (calcd.), 528.2 (M+H⁺, found).

Step 2. N-(Methylsulfonyl)-4-((4-(((1R,2S)-2-phenylcyclopropyl)amino)piperidin-1-yl)methyl)benzamide di-hydrochloride (74)

To a suspension of the compound 73 (182 mg, 0.35 mmol) in dioxane (3 mL) at rt was added a 4M solution of HCl in dioxane (3 ml, 12 mmol). The reaction mixture was stirred at ambient temperature for 3 hrs, evaporated to dryness and the resultant white solid was triturated with acetone, collected by filtration and dried to afford title compound 74 (161 g, 93% yield) as white solid.

$^1$H NMR: 500 MHz, DMSO-d₆, δ (ppm): 12.24 (bs, 1H), 11.07 (bs, 1H), 9.93 (bs, 2H), 8.01 (d, J=8.1 Hz, 2H), 7.74 (bd, 2H), 7.31-7.28 (m, 2H), 7.23-7.16 (m, 3H), 4.33 (bs, 2H), 3.44 (bs, 2H), 3.41 (bs, 1H), 3.39 (s, 3H), 2.99 (bs, 2H), 2.94 (bs, 1H), 2.54 (bs, 1H), 2.27 (bs, 2H), 2.09 (bs, 2H), 1.56 (bs, 1H), 1.31-1.28 (m, 1H). MS: 427.6 (calcd.), 428.1 (M+H⁺, found).

Example 35

N-(Methylsulfonyl)-2-(4-((4-(((1R,2S)-2-phenylcyclopropyl)amino)piperidin-1-yl)methyl)phenyl)acetamide di-hydrochloride (81)

Scheme 15

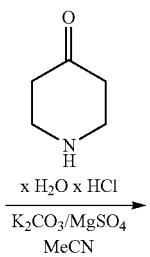
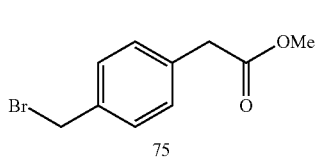

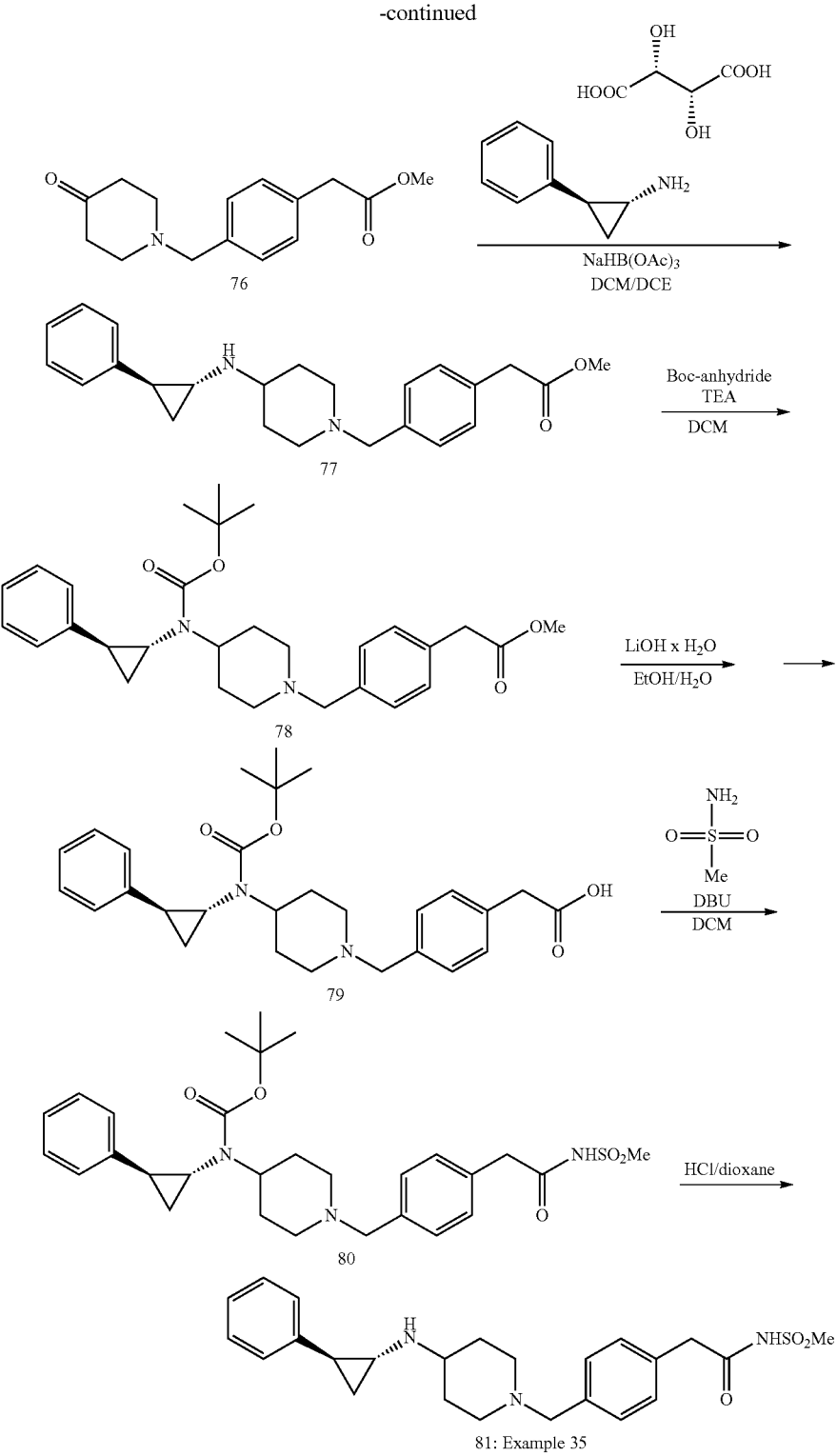

Step 1. Methyl 2-(4-((4-oxopiperidin-1-yl)methyl)phenyl)acetate (76)

A suspension of methyl 2-(4-(bromomethyl)phenyl)acetate (75) (2.0 g, 8.23 mmol), 4-piperidone hydrochloride monohydrate (1.90 g, 12.34 mmol), K$_2$CO$_3$ (4.55 g, 32.9 mmol) and anhydrous MgSO$_4$ (2.34 g 16.5 mmol) in MeCN (60 mL) was stirred at reflux conditions for 3.5 hrs. The mixture was cooled to RT and partitioned between water and EA. The organic phase was collected, dried over anhydrous Na$_2$SO$_4$, filtered and concentrated. The residue was subjected to flash column chromatography, eluent EA, to afford title compound 76 (1.76 g, 82% yield) as colorless oil. $^1$H NMR: 500 MHz, CDCl$_3$, δ (ppm): 7.32 (d, J=6.3 Hz, 2H), 7.25 (d, overlaps with the residual solvent signal, 2H), 3.70 (s, 3H), 3.63 (s, 2H), 3.60 (s, 2H), 2.74 (t, J=6.1 Hz, 4H), 2.45 (t, J=6.2 Hz, 4H). MS: 261.3 (calcd.), 262.0 (M+H$^+$, found).

Step 2. Methyl 2-(4-(((1R,2S)-2-phenylcyclopropyl)amino)piperidin-1-yl)methyl)phenyl)acetate (77)

To a suspension of the (1R,2S)-2-phenylcyclopropanamine (2R,3R)-2,3-dihydroxysuccinate (2.48 g, 8.76 mmol) and ketone 76 (1.76 g, 6.74 mmol) in a 1:1 mixture DCM-DCE (20 mL) were added few drops of glacial AcOH and the resultant reaction mixture was stirred at RT for 4.0 hrs, cooled to 0° C. then treated with sodium tracetoxyborohydride (2.57 g, 12.12 mmol). The mixture was stirred at 0° C. for 30 min then allowed to warm to RT and stirred for an additional 14 hrs. The mixture was then diluted with DCM and washed with conc. NaHCO$_3$ solution. The organic phase was washed with brine, dried over anhydrous Na$_2$SO$_4$, filtered and concentrated. The resultant oil was subjected by flush column chromatography, eluent 10% MeOH in DCM (MeOH contained 2% ammonia) to afford title compound 77 (1.09 g, 43%) as oil.

$^1$H NMR: 500 MHz, MeOD, δ (ppm): 7.7 (d, J=8.2 Hz, 2H), 7.24-7.19 (m, 4H), 7.12-7.09 (m, 1H), 7.03-7.01 (m, 2H), 3.67 (s, 3H), 3.63 (s, 2H), 3.48 (s, 2H), 2.87 (bd, 2H), 2.66-2.60 (m, 1H), 2.30-2.27 (m, 1H), 2.07-2.01 (m, 2H), 1.93-1.85 (m, 3H), 1.50-1.41 (m, 2H), 1.07-0.99 (m, 2H). MS: 378.5 (calcd.), 379.2 (M+H$^+$, found).

Step 3. Methyl 2-(4-((4-((tert-butoxycarbonyl)((1R,2S)-2-phenylcyclopropyl)amino)piperidin-1-yl)methyl)phenyl)acetate (78)

To a solution of compound 77 (1.09 g, 2.88 mmol) in DCM (15 mL) was added TEA (1.2 mL, 8.64 mmol). The mixture was cooled by an ice-bath then treated with a solution of the Boc-anhydride (1.89 g, 8.64 mmol) in DCM (15 mL). The reaction mixture was stirred at 0-5° C. for 30 min then at ambient temperature for 48 hrs, diluted with DCM, washed with diluted brine, dried over anhydrous Na$_2$SO$_4$, filtered and concentrated. The crude product was purified by flash column chromatography, eluent EA-hexanes (1:1) to afford title compound 78 (1.195 g, 87% yield) as honey-like material.

$^1$H NMR, 500 MHz, MeOD, δ (ppm): 7.28-7.22 (m, 6H), 7.16-7.10 (m, 3H), 3.67 (s, 3H), 3.64 (s, 2H), 3.50 and 4.49 (two singlets of rotamers, 2H), 2.88-2.91 (m, 2H), 2.60-2.57 (m, 1H), 2.17-1.94 (m, 6H), 1.78-1.68 (m, 2H), 1.42-1.38 (m, 10H), 1.25-1.21 (m, 1H). MS: 478.6 (calcd.), 479.2 (M+H$^+$, found).

Step 4. 2-(4-((4-((tert-Butoxycarbonyl)((1R,2S)-2-phenylcyclopropyl)amino)piperidin-1-yl)methyl)phenyl)acetic acid (79)

A solution of LiOH×H$_2$O (210 mg, 5.00 mmol) in water (8 mL) was added to a solution of ester 78 (1.195 g, 2.50 mmol) in 70% aqueous EtOH (25 mL). The reaction mixture was stirred at RT for 1 hr, treated with 10% aqueous NaH$_2$PO$_4$ solution (10 mL) and further acidified to pH 4 with 1N HCl solution. The acidic mixture was evaporated under reduced pressure to remove EtOH, the remaining emulsion was treated with brine and extracted with DCM. The extract was dried over anhydrous Na$_2$SO$_4$, filtered and the filtrate was evaporated to afford title compound 79 (1.14 g, 98% yield) as foam which was used in the next step with no additional purification. MS: 464.6 (calcd.), 465.2 (M+H$^+$, found).

Step 5. tert-Butyl (1-(4-(2-(methylsulfonamido)-2-oxoethyl)benzyl)piperidin-4-yl)((1R,2S)-2-phenylcyclopropyl)carbamate (80)

To a solution of acid 79 (150 mg, 0.323 mmol) in DCM (6 mL) at 0° C. was added CDI (63 mg, 0.387 mmol). The reaction mixture was stirred for 5 min, then the ice bath was removed and the mixture was stirred for 1 hour at RT. To the mixture were added methyl sulfonamide (37 mg, 0.387 mmol) and DBU (0.1 mL, 0.646 mmol). The combined mixture was stirred overnight, diluted with more DCM and washed with 10% aqueous NaH$_2$PO$_4$ solution then brine. The organic solution was dried over Na$_2$SO$_4$, filtered and evaporated. The crude product was purified by flash column chromatography, eluent 10, then 15% MeOH in DCM (MeOH contained 2% ammonia) to afford title compound 80 (115 mg, 66% yield) as white solid. MS: 541.7 (calcd.), 542.2 (M+H$^+$, found).

Step 6. N-(Methylsulfonyl)-2-(4-((4-(((1R,2S)-2-phenylcyclopropyl)amino)piperidin-1-yl)methyl)phenyl)acetamide di-hydrochloride (81)

To a solution of compound 80 (115 mg, 0.212 mmol) in dioxane (1.6 mL) was added 4M solution of HCl in dioxane (1.6 ml, 6.40 mmol) at rt. The reaction mixture was stirred at ambient temperature for 3 hrs, evaporated to dryness and the resultant white solid was triturated with acetone and dried in vacuum to afford title compound 81 (118 mg, quant. yield)

$^1$H NMR: 500 MHz, DMSO-d$_6$, δ (ppm): 12.03 (bs, 1H), 10.84 (bs, 1H), 9.91 (bs, 2H), 7.53 (d, J=7.7 Hz, 2H), 7.35-7.28 (m, 4H), 7.23-7.16 (m, 3H), 4.22 (bs, 2H), 3.67 (s, 2H), 3.44 (bs, 2H), 3.41 (bs, 1H), 3.24 (s, 3H), 2.96 (bs, 2H), 2.93 (bs, 1H), 2.54 (bs, 1H), 2.27 (bs, 2H), 2.07 (bs, 2H), 1.57-1.53 (m, 1H), 1.32-1.26 (m, 1H). MS: 441.6 (calcd.), 442.1 (M+H$^+$, found).

Compounds 82-83 (examples 36-38) were synthesized starting from compound 72 by following the procedures described above for the synthesis of compound 74 (example 36, scheme 14) while compound 84 (example 38) was prepared similarly to compound 81 (example 36, scheme 15). Characterization of compounds 82-84 (examples 36-38) is provided in the table 4.

TABLE 4

Characterization of compounds 82-84 (examples 36-38)

| Ex. # | Cpd # | Structure | Characterization |
|---|---|---|---|
| 36 | 82 | N-(Isopropylsulfonyl)-4-((4-(((1R,2S)-2-phenylcyclopropyl)amino)piperidin-1-yl)methyl)benzamide | $^1$H NMR; 500 MHz, DMSO-$d_6$, δ (ppm): 12.09 (bs, 1H), 11.15 (bs, 1H), 9.97 (bs, 2H), 8.00 (d, J = 8.3 Hz, 2H), 7.75 (bd, 2H), 7.31-7.28 (m, 2H), 7.23-7.16 (m, 3H), 4.33 (bs, 2H), 3.83 (sep, J = 6.6 Hz, 1H), 3.44 (bs, 2H), 3.42 (bs, 1H), 3.00 (bs, 2H), 2.93 (bs, 1H), 2.54 (bs, 1H), 2.28 (bs, 2H), 2.10 (bs, 2H), 1.56 (bs, 1H), 1.33 (d, J = 6.7 Hz, 6H), 1.30-1.26 (m, 1H). MS: 455.6 (calcd.), 456.2 (M + H$^+$, found). |
| 37 | 83 | 4-((4-(((1R,2S)-2-Phenylcyclopropyl)amino)piperidin-1-yl)methyl)-N-(phenylsulfonyl)benzamide | $^1$H NMR; 500 MHz, DMSO-$d_6$, δ (ppm): 12.66 (bs, 1H), 11.03 (bs, 1H), 9.90 (bs, 2H), 8.02-8.00 (m, 2H), 7.94 (d, J = 8.4 Hz, 2H), 7.75-7.63 (m, 5H), 7.31-7.28 (m, 2H), 7.23-7.20 (m, 1H), 7.16 (bd, 2H), 4.31 (s, 2H), 3.41 (bs, 3H), 2.96 (bs, 2H), 2.93 (bs, 1H), 2.53 (bs, 1H), 2.25 (bs, 2H), 2.08 (bs, 1H), 2.05 (bs, 1H), 1.54 (bs, 1H), 1.30-1.27 (m, 1H). MS: 489.6 (calcd.), 490.1 (M + H$^+$, found). |
| 38 | 84 | 2-(4-((4-(((1R,2S)-2-phenylcyclopropyl)amino)piperidin-1-yl)methyl)phenyl)-N-(phenylsulfonyl)acetamide | $^1$H NMR; 500 MHz, DMSO-$d_6$, δ (ppm): 12.45 (bs, 1H), 10.80 (bs, 1H), 9.90(bs, 2H), 7.91-7.89 (m, 2H), 7.72-7.69 (m, 1H), 7.63-7.60 (m, 2H), 7.47 (bd, 2H), 7.31-7.28 (m, 2H), 7.24-7.20 (m, 3H), 7.17 (bd, 2H), 4.19 (bs, 2H), 3.61 (s, 2H), 3.40 (bs, 2H), 3.37 (bs, 1H), 2.92 (bs, 3H), 2.53 (bs, 1H), 2.26 (bs, 2H), 2.05 (bs, 2H), 1.56-1.52 (m, 1H), 1.30-1.26 (m, 1H). MS: 503.7 (calcd.), 504.2 (M + H$^+$, found). |

Compounds 85-88 (examples 39-42) were synthesized starting from compound 72 by following the procedures described above for the synthesis of compound 74 (example 35, scheme 14). Compounds 89-90 (examples 43-44) were synthesized starting from compound 72 as well, but by following the procedures described above for the synthesis compound 57 (example 22, scheme 12). Compounds 91-93 (examples 45-47) were synthesized starting from compound 79 by following the procedures described above for the synthesis compound 81 (example 36, scheme 15). Characterization of compounds 85-93 (examples 39-47) is provided in the table 5.

TABLE 5

Characterization of compounds 85-93 (examples 39-47)

| Ex. # | Cpd # | Structure | Characterization |
|---|---|---|---|
| 39 | 85 | N-(cyclopropylsulfonyl)-4-((4-(((1R,2S)-2-phenylcyclopropyl)amino)piperidin-1-yl)methyl)benzamide | $^1$H NMR: 500 MHz, DMSO-$d_6$, δ (ppm): 12.20 (bs, 1H), 11.12 (bs, 1H), 9.96 (bs, 2H), 8.00 (d, J = 8.4 Hz, 2H), 7.75 (bd, 2H), 7.31-7.28 (m, 2H), 7.24-7.16 (m, 3H), 4.34 (bs, 2H), 3.44 (bs, 2H), 3.42 (bs, 1H), 3.16-3.11 (m, 1H), 2.99 (bs, 2H), 2.94 (bs, 1H), 2.54 (bs, 1H), 2.28 (bs, 2H), 2.10 (bs, 2H), 1.56 (bs, 1H), 1.30-1.26 (m, 1H), 1.18-1.13 (m, 4H). MS: 453.6 (calcd.), 454.2 (M + H$^+$, found). |

TABLE 5-continued

Characterization of compounds 85-93 (examples 39-47)

| Ex. # | Cpd # | Structure | Characterization |
|---|---|---|---|
| 40 | 86 | 4-((4-(((1R,2S)-2-phenylcyclopropyl)amino)piperidin-1-yl)methyl)-N-(propylsulfonyl)benzamide | $^{1}$H NMR: 500 MHz, DMSO-$d_6$, δ (ppm): 12.16 (bs, 1H), 11.17 (bs, 1H), 9.97 (bs, 2H), 8.00 (d, J = 8.4 Hz, 2H), 7.75 (bd, 2H), 7.31-7.28 (m, 2H), 7.23-7.17 (m, 3H), 4.33 (bs, 2H), 3.52-3.49 (m, 2H) 3.43 (bs, 2H), 3.41 (bs, 1H), 2.99 (bs, 2H), 2.93 (bs, 1H), 2.55 (bs, 1H), 2.27 (bs, 2H), 2.10 (bs, 2H), 1.77-1.70 (m, 2H) 1.57 (bs, 1H), 1.41 (s, 9H), 1.30-1.26 (m, 1H), 1.00 (t, J = 7.4 Hz, 3H). MS: 455.6 (calcd.), 456.6 (M + H$^+$, found). |
| 41 | 87 | N-(tert-butylsulfonyl)-4-((4-(((1R,2S)-2-phenylcyclopropyl)amino)piperidin-1-yl)methyl)benzamide | $^{1}$H NMR: 500 MHz, DMSO-$d_6$, δ (ppm): 11.64 (bs, 1H), 11.13 (bs, 1H), 9.94 (bs, 2H), 7.95 (d, J = 8.3 Hz, 2H), 7.73 (bd, 2H), 7.31-7.28 (m, 2H), 7.24-7.16 (m, 3H), 4.33 (bs, 2H), 3.43 (bs, 2H), 3.42 (bs, 1H), 2.99 (bs, 2H), 2.93 (bs, 1H), 2.54 (m, 1H), 2.28 (bs, 2H), 2.10 (bs, 2H), 1.58-1.54 (m, 1H), 1.41 (s, 9H), 1.30-1.26 (m, 1H). MS: 469.6 (calcd.), 470.2 (M + H$^+$, found). |
| 42 | 88 | N-(ethylsulfonyl)-4-((4-(((1R,2S)-2-phenylcyclopropyl)amino)piperidin-1-yl)methyl)benzamide | $^{1}$H NMR: 500 MHz, DMSO-$d_6$, δ (ppm): 12.13 (bs, 1H), 11.11 (bs, 1H), 9.94 (bs, 2H), 8.01 (d, J = 8.4 Hz, 2H), 7.75 (bd, 2H), 7.31-7.28 (m, 2H), 7.24-7.16 (m, 3H), 4.33 (bs, 2H), 3.53 (q, J = 7.4 Hz, 2H), 3.44 (bs, 2H), 3.42 (bs, 1H), 2.99 (bs, 2H), 2.93 (bs, 1H), 2.54 (bs, 1H), 2.27 (bs, 2H), 2.10 (bs, 2H), 1.56 (bs, 1H), 1.28 (m, 1H), 1.26 (t, J = 7.4 Hz, 2H. MS: 441.6 (calcd.), 442.2 (M + H$^+$, found). |
| 44 | 89 | N-methoxy-4-((4-(((1R,2S)-2-phenylcyclopropyl)amino)piperidin-1-yl)methyl)benzamide | $^{1}$H NMR: 500 MHz, DMSO-$d_6$, δ (ppm): 11.91 (bs, 1H), 11.10 (bs, 1H), 9.98 (bs, 2H), 7.83 (d, J = 8.1 Hz, 2H), 7.69 (bd, 2H), 7.31-7.28 (m, 2H), 7.23-7.16 (m, 3H), 4.30 (bs, 2H), 3.71 (s, 3H), 3.43 (bs, 2H), 3.41 (bs, 1H), 2.99 (bs, 2H), 2.92 (bs, 1H), 2.56-2.52 (m, 1H), 2.27 (bs, 2H), 2.09 (bs, 2H), 1.58-1.54 (m, 1H), 1.29-1.25 (m, 1H). MS: 379.5 (calcd.), 380.6 (M + H$^+$, found). |
| 45 | 90 | N-ethoxy-4-((4-(((1R,2S)-2-phenylcyclopropyl)amino)piperidin-1-yl)methyl)benzamide | $^{1}$H NMR: 500 MHz, DMSO-$d_6$, δ (ppm): 11.77 (bs, 1H), 11.08 (bs, 1H), 9.96 (bs, 2H), 7.83 (d, J = 8.1 Hz, 2H), 7.68 (d, J = 7.9 Hz, 2H), 7.31-7.28 (m, 2H), 7.24-7.16 (m, 3H), 4.30 (bs, 2H), 3.93 (q, J = 7.0 Hz, 2H), 3.43 (bs, 2H), 3.41 (bs, 1H), 2.99 (bs, 2H), 2.92 (bs, 1H), 2.56-2.53 (m, 1H), 2.28 (bs, 2H), 2.09 (bs, 2H), 1.58-1.53 (m, 1H), 1.29-1.25 (m, 1H), 1.21 (t, J = 7.0 Hz, 3H), MS: 393.5 (calcd.), 394.6 (M + H$^+$, found). |
| 45 | 91 | N-(cyclopropylsulfonyl)-2-(4-((4-(((1R,2S)-2-phenylcyclopropyl)amino)piperidin-1-yl)methyl)phenyl)acetamide | $^{1}$H NMR: 500 MHz, DMSO-$d_6$, δ (ppm): 11.97 (bs, 1H), 10.88 (bs, 1H), 9.93 (bs, 2H), 7.54 (d, J = 7.9 Hz, 2H), 7.35-7.28 (m, 4H), 7.24-7.16 (m, 3H), 4.23 (bs, 2H), 3.68 (s, 2H), 3.44 (bs, 2H), 3.41 (bs, 1H), 2.97 (bs, 2H), 2.96-2.91 (m, 2H), 2.53 (m, 1H), 2.28 (bs, 2H), 2.06 (bs, 2H), 1.57-1.53 (m, 1H), 1.30-1.26 (m, 1H), 1.08-1.07 (m, 4H). MS: 467.6 (calcd.), 468.2 (M + H$^+$, found). |

TABLE 5-continued

Characterization of compounds 85-93 (examples 39-47)

| Ex. # | Cpd # | Structure | Characterization |
|---|---|---|---|
| 46 | 92 | N-(ethylsulfonyl)-2-(4-((4-(((1R,2S)-2-phenylcyclopropyl)amino)piperidin-1-yl)methyl)phenyl)acetamide | $^1$H NMR: 500 MHz, DMSO-d$_6$, δ (ppm): 11.91 (bs, 1H), 10.91 (bs, 1H), 9.97 (bs, 2H), 7.54 (d, J = 7.9 Hz, 2H), 7.36-7.28 (m, 4H), 7.23-7.16 (m, 3H), 4.22 (bs, 2H), 3.69 (s, 2H), 3.43 (bs, 2H), 3.41 (bs, 1H), 3.36-3.32 (m, 2H, obscured by the residual water peak), 2.97 (bs, 2H), 2.92 (bs, 1H), 2.54 (m, 1H), 2.28 (bs, 2H), 2.08 (bs, 2H), 1.57-1.54 (m, 1H), 1.29-1.25 (m, 1H), 1.18 (t, J = 7.4 Hz, 3H). MS: 455.6 (calcd.), 456.2 (M + H$^+$, found). |
| 47 | 93 | N-(isopropylsulfonyl)-2-(4-((4-(((1R,2S)-2-phenylcyclopropyl)amino)piperidin-1-yl)methyl)phenyl)acetamide | $^1$H NMR: 500 MHz, DMSO-d$_6$, δ (ppm): 11.84 (bs, 1H), 10.93 (bs, 1H), 9.98 (bs, 2H), 7.54 (d, J = 7.9 Hz, 2H), 7.36-7.28 (m, 4H), 7.23-7.16 (m, 3H), 4.22 (bs, 2H), 3.69 (s, 2H), 3.56 (septet, J = 6.7 Hz, 1H), 3.43 (bs, 2H), 3.40 (bs, 1H), 2.97 (bs, 2H), 2.92 (bs, 1H), 2.55 (m, 1H), 2.28 (bs, 2H), 2.08 (bs, 2H), 1.58-1.54 (m, 1H), 1.29-1.23 (m, 7H). MS: 469.6 (calcd.), 470.2 (M + H$^+$, found). |

Example 48

(E)-3-(4-((4-((((1R,2S)-2-Phenylcyclopropyl)amino)methyl)piperidin-1-yl)methyl)phenyl)-N-(phenylsulfonyl)acrylamide di-hydrochloride (94)

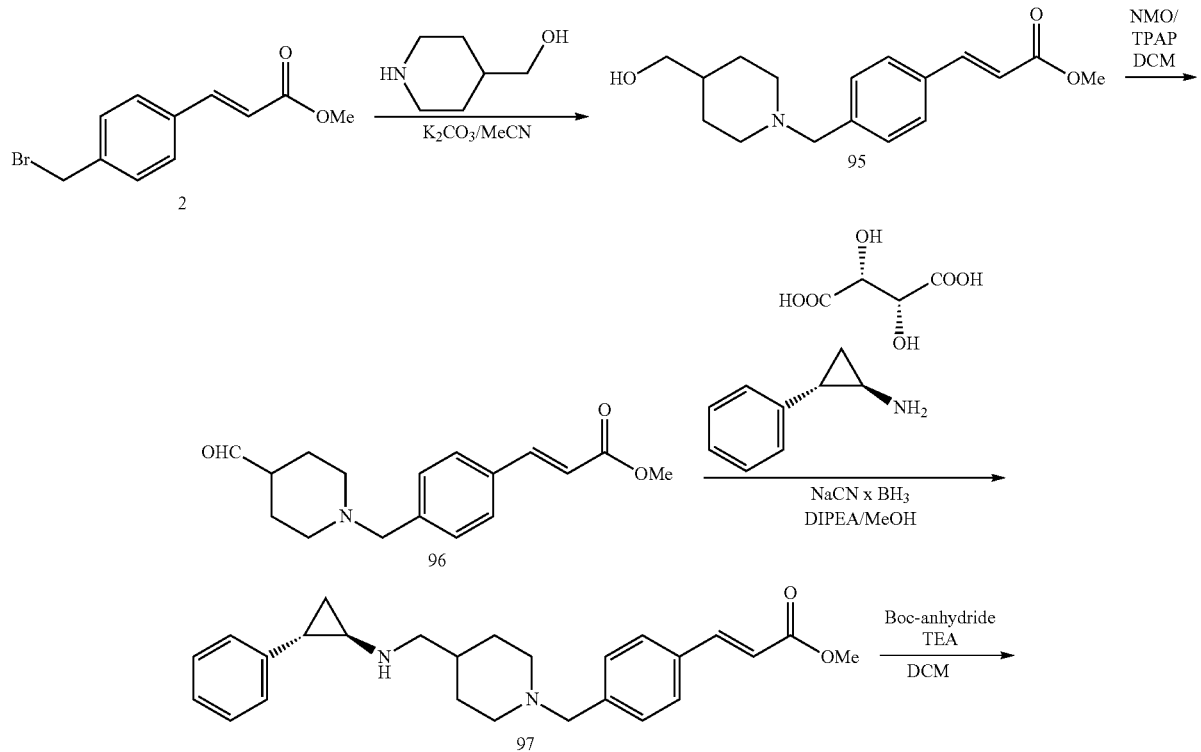

Scheme 16

-continued

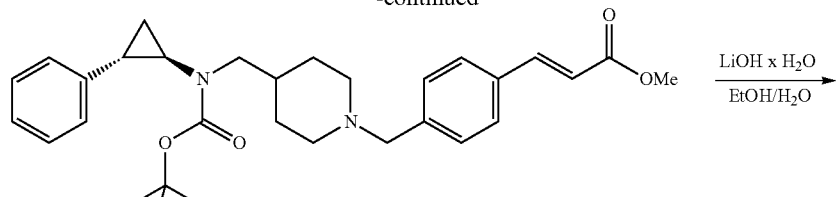

98

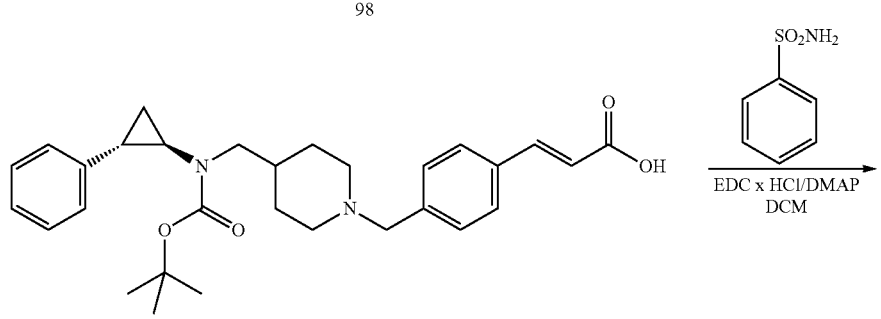

99

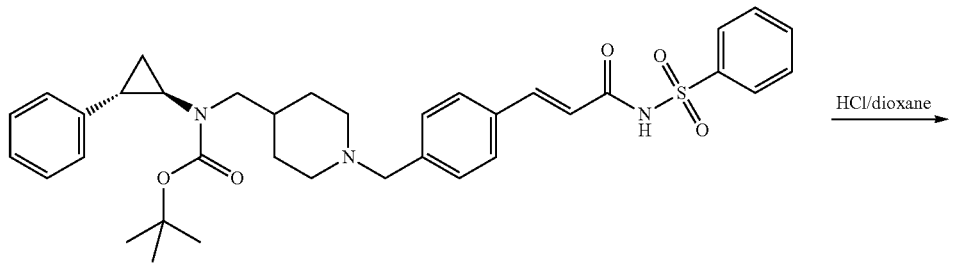

100

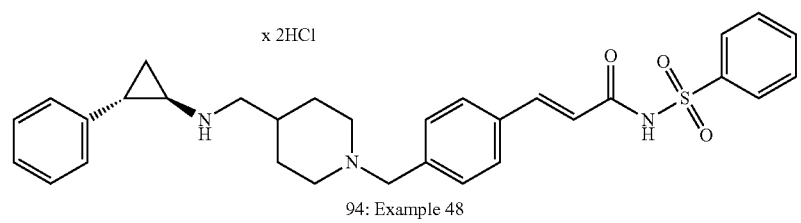 [SMILES: O=C(/C=C/c1ccc(CN2CCC(CN[C@@H]3C[C@H]3c3ccccc3)CC2)cc1)NS(=O)(=O)c1ccccc1]

94: Example 48

Step 1. (E)-Methyl 3-(4-((4-(hydroxymethyl)piperidin-1-yl)methyl)phenyl)acrylate (95)

A suspension of the bromide 2 (2.4 g, 9.41 mmol, scheme 1), 4-piperidinemethanol (1.379 g, 11.97 mmol) and $K_2CO_3$ (3.90 g, 28.2 mmol) in MeCN (40 mL) was stirred at reflux conditions for 5 hrs. The mixture was cooled to RT and filtered. The solid was washed with EA. The filtrate and washings were combined and washed with brine, dried over anhydrous $Na_2SO_4$, filtered and the filtrate was evaporated to yield an oil. The material was purified by flash column chromatography, eluent 10% MeOH in DCM and at the end 15% MeOH in DCM (MeOH contained 2% ammonia), to afford title compound 95 (2.20 g, 81% yield) as an oil that has solidified in vacuum. MS: 289.4 (calcd.), 290.1 (M+H$^+$, found).

$^1$H NMR: 500 MHz, acetone-d$_6$, δ (ppm): 7.67 (d, J=16.0 Hz, 1H), 7.63 (d, J=8.2 Hz, 2H), 7.40 (d, J=8.1 Hz, 2H), 6.52 (d, J=16.0 Hz, 1H), 3.74 (s, 3H), 3.49 (s, 2H), 3.38 (d, J=6.3 Hz, 2H), 2.86-2.82 (m, 2H, partially overlaps with the residual HOD signal)), 2.07-2.05 (m, 1H, partially overlaps with the residual solvent signal), 1.98-1.93 (m, 2H), 1.69 (bd, 2H), 1.47-1.40 (m, 2H), 1.28-1.19 (m, 2H).

Step 2. (E)-Methyl 3-(4-((4-formylpiperidin-1-yl)methyl)phenyl)acrylate (96)

To a solution of the alcohol 95 (2.20 g, 7.60 mmol) in DCM (35 mL) was added NMO (1.336 g, 11.40 mmol) and the 4 A molecular sieves (4 g), and the mixture was stirred for 15 min at RT (tap water bath). To the mixture was added TPAP (267 mg, 0.760 mmol) in small portions over 5 min. The resultant solution was stirred at RT for 5 hrs diluted with more DCM and filtered trough a celite pad. The filtrate was washed with dilute brine, dried over anhydrous $Na_2SO_4$, concentrated and subjected to flash column chromatography, eluent 10% MeOH (with 2% ammonia) in DCM to afford title compound 96 (1.15 g, 53% yield) as brownish honey-like material.

$^1$H NMR: 500 MHz, CDCl$_3$, δ (ppm): 9.65 (d, J=1.2 Hz, 1H), 7.68 (d, J=16.0 Hz, 1H), 7.47 (d, J=8.1 Hz, 2H), 7.33 (d, J=8.1 Hz, 2H), 6.42 (d, J=16.0 Hz, 1H), 3.80 (s, 3H), 3.50 (s, 2H), 2.82-2.78 (m, 2H), 2.26-2.22 (m, 1H), 2.14-2.09 (m, 2H), 1.91-1.86 (m, 2H), 1.73-1.65 (m, 2H). MS: 287.43 (calcd.), 288.1 (M+H⁺, found).

Step 3. (E)-Methyl 3-(4-((4-((((1R,2S)-2-phenylcyclopropyl)amino)methyl)piperidin-1-yl)methyl)phenyl)acrylate (97)

To a suspension of (1R,2S)-2-phenylcyclopropanamine (2R,3R)-2,3-dihydroxysuccinate (1.36 g, 4.80 mmol) in MeOH (25 mL) was added DIPEA (1.673 mL, 9.60 mmol) and the mixture was stirred until the suspension turned into a clear solution. The clear solution was added to a solution of the aldehyde 96 (1.15 g, 4.00 mmol) in MeOH (25 mL). The resultant mixture was brought to reflux and kept under these conditions for 10 min then cooled to RT. Sodium cyanoborohydride (377 mg, 6.00 mmol) was added to the reaction mixture, the mixture was stirred for 1 hr at RT and quenched with water (10 mL). MeOH was evaporated under reduced pressure and the remaining oil was partitioned between water and DCM. The organic phase was collected, dried over anhydrous Na₂SO₄, filtered, concentrated and subjected to flash column chromatography, eluent 5, 10 then 15% MeOH (with 2% ammonia) in DCM to afford title compound 97 (894 mg, 55% yield) as a honey-like material. MS: 404.5 (calcd.), 405.3 (M+H⁺, found).

Step 4. (E)-Methyl 3-(4-((4-(((tert-butoxycarbonyl)((1R,2S)-2-phenylcyclopropyl)amino)methyl)piperidin-1-yl)methyl)phenyl)acrylate (98)

To a solution of the amine 97 (894 mg, 2.21 mmol) in DCM (10 mL) was added TEA (0.924 mL, 6.63 mmol) and the solution was cooled by an ice-bath. To the cold solution was added a solution of the Boc-anhydride (965 mg, 4.42 mmol) in DCM (10 mL). The mixture was stirred at 0-5° C. for 30 min then at ambient temperature for 2 hrs, diluted with DCM, washed with water, dried over anhydrous Na₂SO₄, filtered and concentrated. The residue was purified by flash column chromatography, eluent EA-hexanes (10:2) to afford title compound 98 (611 mg, 55% yield) as a honey-like material. MS: 504.7 (calcd.), 505.3 (M+H⁺, found).

Step 5. (E)-3-(4-((4-(((tert-Butoxycarbonyl)((1R,2S)-2-phenylcyclopropyl)amino)methyl)piperidin-1-yl)methyl)phenyl)acrylic acid (99)

To a solution of ester 98 (611 mg, 1.211 mmol) in 10 mL of 70% aqueous EtOH was added a solution of LiOH×H₂O (132 mg, 3.15 mmol) in water (3 mL). The reaction mixture was stirred at rt for 5 hrs, acidified to pH 4 then evaporated to its maximum. The residue was diluted with DCM and washed with brine, dried over anhydrous Na₂SO₄, filtered end evaporated to afford title compound 99 (585 g, 98% yield) as a white fluffy solid. MS: 490.6 (calcd.), 491.2 (M+H⁺, found).

Step 6. tert-Butyl ((1-(4-((E)-3-oxo-3-(phenylsulfonamido)prop-1-en-1-yl)benzyl)piperidin-4-yl)methyl)((1R,2S)-2-phenylcyclopropyl)carbamate (100)

To a solution of acid 99 (100 mg, 0.204 mmol) and benzene sulfonamide (48 mg, 0.306 mmol) in DCM (7 mL) was added EDC×HCl (78 mg, 0.408 mmol) and DMAP (50 mg, 0.408 mmol) at RT. The reaction mixture was stirred at the same conditions overnight, diluted with more DCM then sequentially washed with a NaHCO₃ solution, water and brine; dried over anhydrous Na₂SO₄, filtered and concentrated. The residue was purified by flash column chromatography, eluent 10% MeOH in DCM (MeOH contained 2% ammonia) to afford title compound 100 (51 mg, 40% yield) as an off-white fluffy solid. MS: 629.8 (calcd.), 630.2 (M+H⁺, found).

Step 7. (E)-3-(4-((4-((((1R,2S)-2-Phenylcyclopropyl)amino)methyl)piperidin-1-yl)methyl)phenyl)-N-(phenylsulfonyl)acrylamide di-hydrochloride (94)

To a solution of compound 100 (51 mg, 0.081 mmol) in dioxane (1.0 mL) was added a 4M solution of HCl in dioxane (0.61 ml) at rt and the mixture was stirred at ambient temperature for 3 hrs. The mixture was evaporated to dryness and the resultant white precipitate was triturated with acetone, collected by filtration and dried in vacuum to afford title compound 94 (40 mg, 82% yield) as a white solid.

¹H NMR: 500 MHz, DMSO-d₆, δ (ppm): 12.41 (bs, 1H), 10.85 (bs, 1H), 9.54 and 8.92 (bs, 2H), 7.98-7.97 (m, 2H), 7.74-7.71 (m, 1H), 7.67-7.63 (m, 6H), 7.59 (d, J=15.8 Hz, 1H), 7.32-7.28 (m, 2H), 7.23-7.16 (m, 3H), 6.69 (d, J=15.9 Hz, 1H), 4.26 (bs, 2H), 2.96-2.88 (m, 5H), 2.64 (m, 1H), 2.58 (m, 1H), 1.99-1.93 (m, 4H), 1.60-1.55 (m, 3H), 1.26-1.22 (m, 1H). MS: 529.7 (calcd.), 530.2 (M+H⁺, found).

Compounds 101-104 (examples 49-52) were synthesized starting from compound 99 by following the procedures described above for the synthesis of compound 94 (example 48, scheme 16). Characterization of compounds 101-104 (examples 49-52) is provided in the table 6.

TABLE 6

Characterization of compounds 101-104 (examples 49-52)

| Ex. # | Cpd # | Structure | Characterization |
|---|---|---|---|
| 49 | 101 | 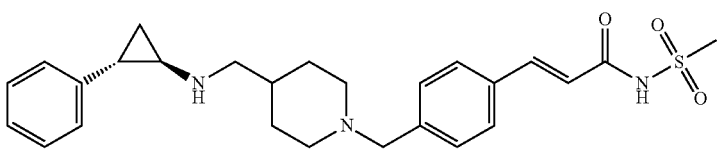<br>(E)-N-(methylsulfonyl)-3-(4-((4-((((1R,2S)-2-phenylcyclopropyl)amino)methyl)piperidin-1-yl)methyl)phenyl)acrylamide | ¹H NMR: 500 MHz, DMSO-d₆, δ (ppm): 11.99 (bs, 1H), 11.04 (bs, 1H), 9.64 and 9.02 (bs, 2H), 7.73-7.68 (m, 5H), 7.31-7.28 (m, 2H), 7.23-7.16 (m, 3H), 6.75 (d, J = 15.9 Hz, 1H), 4.28 (bs, 2H), 3.32 (s, 3H), 2.97-2.88 (m, 5H), 2.66-2.58 (m, 2H), 2.02-1.95 (m, 4H), 1.67-1.60 (m, 3H), 1.25-1.21 (m, 1H). MS: 467.6 (calcd.), 468.2 (M + H⁺, found). |

TABLE 6-continued

Characterization of compounds 101-104 (examples 49-52)

| Ex. # | Cpd # | Structure | Characterization |
|---|---|---|---|
| 50 | 102 | (E)-N-(ethylsulfonyl)-3-(4-((4-((((1R,2S)-2-phenylcyclopropyl)amino)methyl)piperidin-1-yl)methyl)phenyl)acrylamide | $^1$H NMR: 500 MHz, DMSO-d$_6$, δ (ppm): 11.89 (bs, 1H), 10.91 (bs, 1H), 9.57 and 8.94 (bs, 2H), 7.73-7.70 (m, 5H), 7.32-7.29 (m, 2H), 7.24-7.17 (m, 3H), 6.76 (d, J = 15.9 Hz, 1H), 4.29 (bs, 2H), 3.46 (q, J = 7.4 Hz, 2H), 2.98-2.88 (m, 5H), 2.65 (m, 1H), 2.59 (m, 1H), 2.01-1.96 (m, 4H), 1.66-1.58 (m, 3H), 1.26-1.23 (m, 4H). MS: 481.7 (calcd.), 482.2 (M + H$^+$, found). |
| 51 | 103 | (E)-N-(cyclopropylsulfonyl)-3-(4-((4-((((1R,2S)-2-phenylcyclopropyl)amino)methyl)piperidin-1-yl)methyl)phenyl)acrylamide | $^1$H NMR: 500 MHz, DMSO-d$_6$, δ (ppm): 11.94 (bs, 1H), 10.87 (bs, 1H), 9.54 and 8.92 (bs, 2H), 7.73-7.69 (m, 5H), 7.31-7.28 (m, 2H), 7.23-7.17 (m, 3H), 6.75 (d, J = 15.9 Hz, 1H), 4.28 (bs, 2H), 3.07-3.02 (m, 1H), 2.97-2.87 (m, 5H), 2.66-2.63 (m, 1H), 2.56 (bs, 1H), 2.01-1.95 (m, 4H), 1.60-1.59 (m, 3H), 1.26-1.22 (m, 1H), 1.14-1.10 (m, 4H). MS: 493.7 (calcd.), 494.2 (M + H$^+$, found). |
| 52 | 104 | (E)-N-methyl-N-(methylsulfonyl)-3-(4-((4-((((1R,2S)-2-phenylcyclopropyl)amino)methyl)piperidin-1-yl)methyl)phenyl)acrylamide | $^1$H NMR: 500 MHz, DMSO-d$_6$, δ (ppm): 10.88 (bs, 1H), 9.54 (bs, 1H), 8.92 (bs, 1H), 7.83 (d, J = 8.1 Hz, 2H), 7.71-7.67 (m, 3H), 7.35-7.28 (m, 3H), 7.23-7.16 (m, 3H), 4.29 (bd, 2H), 3.45 (s, 3H), 3.30 (s, 3H), 2.98-2.86 (m, 5H), 2.66-2.63 (m, 1H), 2.60-2.56 (m, 1H), 2.01-1.95 (m, 4H), 1.64-1.57 (m, 3H), 1.26-1.22 (m, 1H). MS: 481.7 (calcd.), 482.2 (M + H$^+$, found). |

Example 53

N-(Methylsulfonyl)-4-((4-((((1R,2S)-2-phenylcyclopropyl)amino)methyl)piperidin-1-yl)methyl)benzamide di-hydrochloride (105)

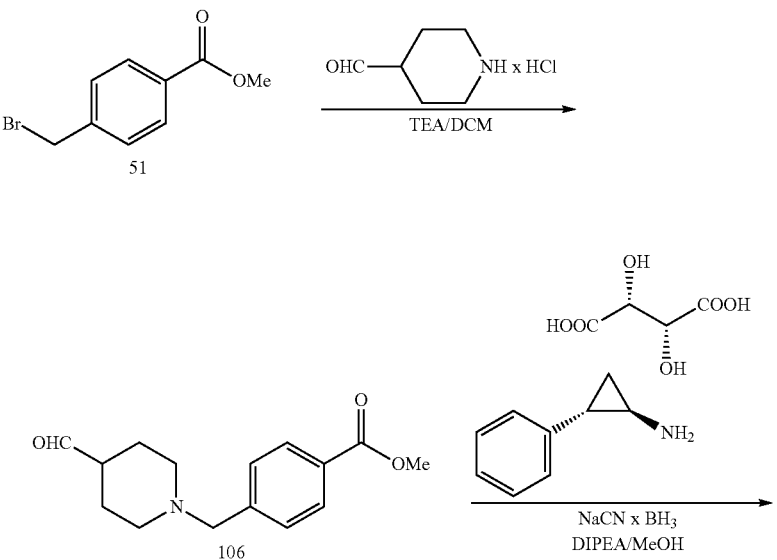

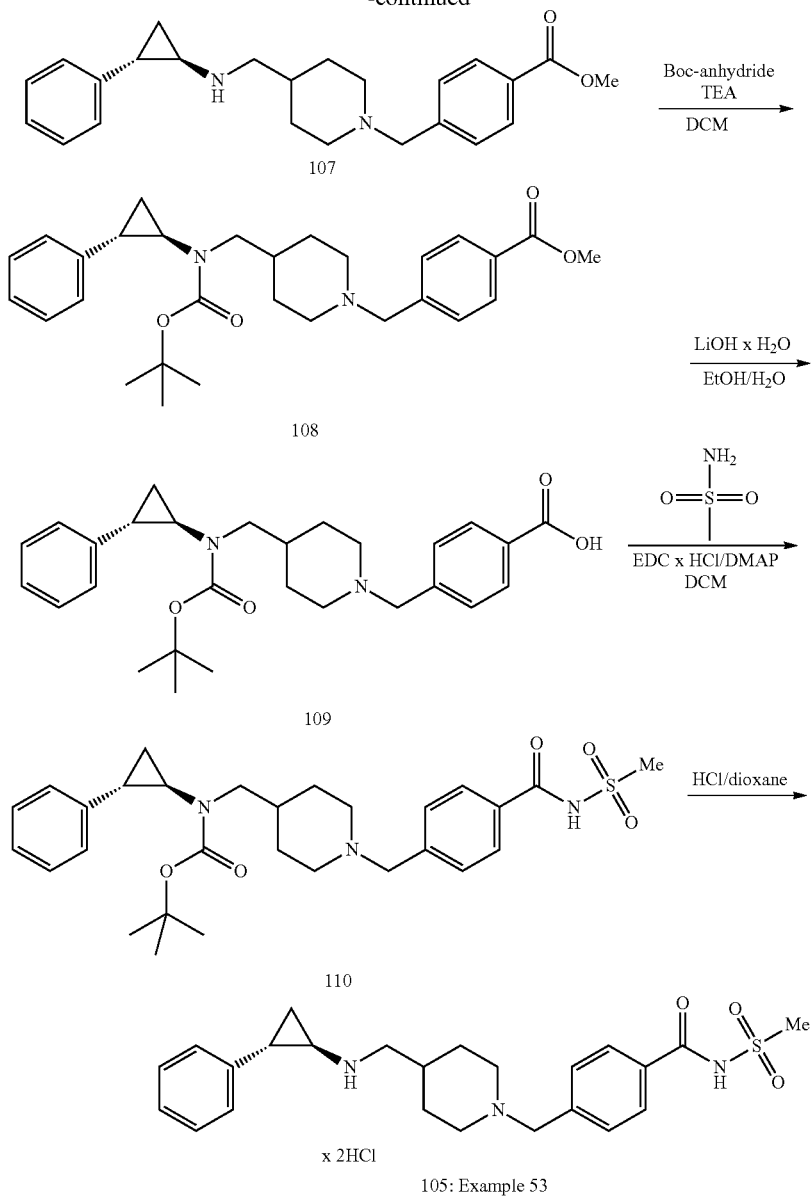

105: Example 53

Step 1. Methyl 4-((4-formylpiperidin-1-yl)methyl)benzoate (106)

To a solution of the 4-formylpiperidine hydrochloride (1.656 g, 1.056 mmol) in DMF at 0° C. was added dropwise TEA (5.84 mL, 41.9 mmol). The mixture was stirred under these conditions for 5 min followed-up by addition of methyl 4-(bromomethyl)benzoate (51) (2.40 g, 10.48 mmol) in small portions. The reaction mixture was stirred for 3 hrs at ambient temperature, diluted with brine and extracted with EA. The extract was washed with brine, dried over anhydrous $Na_2SO_4$, filtered and evaporated. The remaining oil was purified by flash column chromatography, eluent 10% hexanes in EA then pure EA to afford title compound 106 (1.23 g. 45% yield).

$^1$H NMR: 500 MHz, $CDCl_3$, δ (ppm): 9.65 (d, J=1.2 Hz, 1H), 7.98 (d, J=8.4 Hz, 2H), 7.39 (d, J=8.5 Hz, 2H), 3.91 (s, 3H), 3.54 (s, 2H), 2.81-2.77 (m, 2H), 2.26-2.22 (m, 1H), 2.15-2.10 (m, 2H), 1.91-1.86 (m, 2H), 1.73-1.66 (m, 2H). MS: 261.3 (calcd.), 262.0 (M+H$^+$, found).

Step 2. Methyl 4-((4-((((1R,2S)-2-phenylcyclopropyl)amino)methyl)piperidin-1-yl)methyl)benzoate (107)

To a suspension of (1R,2S)-2-phenylcyclopropanamine (2R,3R)-2,3-dihydroxysuccinate (1.6 g, 5.65 mmol) in MeOH (30 mL) was added DIPEA (1.968 mL, 11.30 mmol) and the mixture was stirred until the suspension turned into a clear solution. The solution was added to a solution of the aldehyde 106 (1.23 g, 4.71 mmol) in MeOH (30 mL). The resultant mixture was brought to reflux and kept under these conditions for 10 min then cooled to RT. Borohydride (444 mg, 7.06 mmol) was added to the reaction mixture which was stirred for 2 hrs at RT and treated with water (20 mL). MeOH was evaporated under reduced pressure and the remaining aqueous solution was extracted with DCM. The extract was dried over anhydrous Na$_2$SO$_4$, filtered and concentrated. The residue was purified by flash column chromatography, eluent EA then 10 and finally 20% MeOH in EA (MeOH contained 2% ammonia) to afford title compound 107 (828 mg, 47% yield) as a honey-like material. MS: 378.5 (calcd.), 379.3 (M+H$^+$, found).

Step 3. Methyl 4-((4-(((tert-butoxycarbonyl)((1R,2S)-2-phenylcyclopropyl)amino)methyl)piperidin-1-yl)methyl)benzoate (108)

To a solution of the compound 107 (828 mg, 2.188 mmol) in DCM (10 mL) was added TEA (0.918 mL, 6.56 mmol). The mixture was cooled by an ice-bath then treated with a solution of the Boc-anhydride (955 mg, 4.38 mmol) in DCM (10 mL). The reaction mixture was stirred at 0-5° C. for 30 min then at ambient temperature for 2 hrs, diluted with DCM, washed with water, dried over anhydrous Na$_2$SO$_4$, filtered and concentrated. The residue was purified by flash column chromatography, eluent EA-hexanes (8:2) to afford title compound 108 (587 mg, 56% yield) as a honey-like material which was taken to the next step with no extra-purification. MS: 478.6 (calcd.), 479.4 (M+H$^+$, found).

Step 4. 4-((4-(((tert-Butoxycarbonyl)((1R,2S)-2-phenylcyclopropyl)amino)methyl)piperidin-1-yl)methyl)benzoic acid (109)

To a solution of the ester 108 (587 mg, 1.226 mmol) in THF (10 mL) was added a solution of LiOH×H$_2$O (154 mg, 3.68 mmol) in water (10 mL). The reaction mixture was stirred at rt for 20 hrs, acidified to pH 7 with HCl. The solution was evaporated to its maximum to remove THF. The residual aqueous emulsion was treated with brine and extracted with DCM. The extract was dried over Na$_2$SO$_4$, filtered and concentrated. Hexane was added to the concentrated solution to force the precipitation of the product. The resultant suspension was further evaporated and the resultant solid was kept in vacuum to afford title compound 109 (509 mg, 89% yield) as a white fluffy material. The material was taken to the next step with no extra purification. MS: 464.6 (calcd.), 465.2 (M+H$^+$, found).

Step 5. tert-Butyl ((1-(4-((methylsulfonyl)carbamoyl)benzyl)piperidin-4-yl)methyl)((1R,2S)-2-phenylcyclopropyl)carbamate (110)

To a solution of the acid 109 (144 mg, 0.310 mmol) in DCM (7 mL) were added methane sulfonamide (59 mg, 0.620 mmol), EDC×HCl (149 mg, 0.775 mmol) and DMAP (95 mg, 0.775 mmol) at RT. The reaction mixture was stirred at the same conditions overnight, diluted with more DCM then sequentially washed with a NaHCO$_3$ solution, water and brine. Finally, the solution was dried over Na$_2$SO$_4$, filtered and evaporated. The residue was purified by flash column chromatography, eluent 10, then 15% MeOH in DCM (MeOH contained 2% ammonia) to afford title compound 110 (58 mg, 35% yield) as a white solid. MS: 541.7 (calcd.), 542.3 (M+H$^+$, found).

Step 6. N-(Methylsulfonyl)-4-((4-((((1R,2S)-2-phenylcyclopropyl)amino)methyl)piperidin-1-yl)methyl)benzamide di-hydrochloride (105)

To a solution of the compound 110 (58 mg, 0.107 mmol) in dioxane (1.0 mL) was added a 4M solution of HCl in dioxane (0.8 mL). The reaction mixture was stirred at ambient temperature for 3 hrs, evaporated to dryness and the resultant white precipitate was triturated with a mixture MeOH/acetone/hexanes, collected by filtration and dried in vacuum to afford title compound 105 (41 mg, 74% yield).
$^1$H NMR: 500 MHz, DMSO-d$_6$, δ (ppm): 12.42 (bs, 1H), 11.01 (bs, 1H), 9.59 and 8.97 (bs, 2H), 8.00 (d, J=8.1 Hz, 2H), 7.77 (d, J=8.2 Hz, 2H), 7.32-7.28 (m, 2H), 7.23-7.17 (m, 3H), 4.33 (bs, 2H), 3.38 (s, 3H), 3.10 (bs) and 2.79 (bs, 1H, rotamers), 2.97-2.88 (m, 5H), 2.66-2.63 (m) and 2.59 (bs, 1H, rotamers), 2.01-1.95 (m, 4H), 1.63-1.60 (m, 3H), 1.26-1.22 (m, 1H). MS: 441.6 (calcd.), 442.2 (M+H$^+$, found).

Compounds 111-113 (examples 54-56) were synthesized starting from compound 109 by following the procedures described above for the synthesis of compound 105 (example 52, scheme 17). Characterization of compounds 111-113 (examples 54-56) is provided in the table 7.

TABLE 7

Characterization of compounds 111-113 (examples 54-56)

| Ex. # | Cpd # | Structure | Characterization |
|---|---|---|---|
| 54 | 111 | 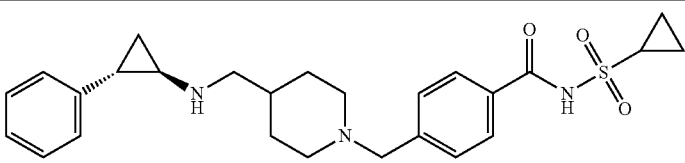<br>N-(cyclopropylsulfonyl)-4-((4-((((1R,2S)-2-phenylcyclopropyl)amino)methyl)piperidin-1-yl)methyl)benzamide | $^1$H NMR: 500 MHz, DMSO-d$_6$, δ (ppm): 12.18 (bs, 1H), 11.06 (bs, 1H), 9.63 and 9.02 (bs, 2H), 8.00 (d, J = 8.3 Hz, 2H), 7.78 (d, J = 8.2 Hz, 2H), 7.31-7.28 (m, 2H), 7.23-7.16 (m, 3H), 4.34 (bs, 2H), 3.16-3.11 (m, 1H), 2.96-2.86 (m, 5H), 2.80-2.59 (m, 2H, rotamers), 2.01-1.96 (m, 4H), 1.64-1.59 (m, 3H), 1.25-1.22 (m, 1H), 1.18-1.10 (m, 4H). MS: 467.6 (calcd.), 468.2 (M + H$^+$, found). |
| 55 | 112 | 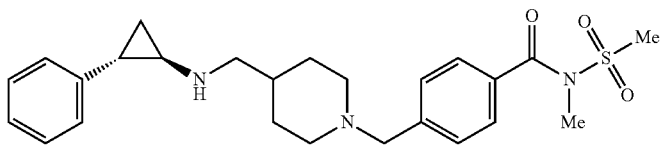 [SMILES: CN(C(=O)c1ccc(CN2CCC(CN[C@@H]3C[C@H]3c3ccccc3)CC2)cc1)S(C)(=O)=O]<br>N-methyl-N-(methylsulfonyl)-4-((4-((((1R,2S)-2-phenylcyclopropyl)amino)methyl)piperidin-1-yl)methyl)benzamide | $^1$H NMR: 500 MHz, DMSO-d$_6$, δ (ppm): 10.92 (bs, 1H), 9.57 (bs, 1H), 8.94 (bs, 1H), 7.77-7.71 (m, 4H), 7.32-7.28 (m, 2H), 7.23-7.17 (m, 3H), 4.33 (bd, 2H), 3.45 (s, 3H), 3.19 (s, 3H), 3.11-2.57 (m, 7H), 2.02-1.93 (m, 4H), 1.65-1.57 (m, 3H), 1.26-1.22 (m, 1H). MS: 467.6 (calcd.), 456.2 (M + H$^+$, found). |

US 10,059,668 B2

97                                                                                                        98

TABLE 7-continued

Characterization of compounds 111-113 (examples 54-56)

| Ex. # | Cpd # | Structure | Characterization |
|-------|-------|-----------|------------------|
| 56 | 113 | 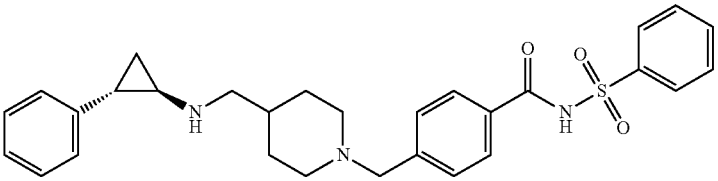 [SMILES: O=C(NS(=O)(=O)c1ccccc1)c1ccc(CN2CCC(CN[C@@H]3C[C@H]3c3ccccc3)CC2)cc1]<br>4-((4-(((((1R,2S)-2-phenylcyclopropyl)amino)methyl)piperidin-1-yl)methyl)-N-(phenylsulfonyl)benzamide | $^1$H NMR: 500 MHz, DMSO-$d_6$, δ (ppm): 12.67 (bs, 1H), 11.03 (bs, 1H), 9.61 and 8.99 (bs, 2H), 8.01 (d, J = 8.7 Hz, 2H), 7.94 (d, J = 8.2 Hz, 2H), 7.75-7.72 (m, 3H), 7.67-7.64 (m, 2H), 7.32-7.28 (m, 2H), 7.23-7.17 (m, 3H), 4.32 (bs, 2H), 3.08-2.58 (m, 7H), 2.00-1.95 (m, 4H), 1.65-1.57 (m, 3H), 1.28-1.22 (m, 1H). MS: 503.7 (calcd.), 504.2 (M + H$^+$, found). |

Example 57

N-(Methylsulfonyl)-4-((4-(((((1R,2S)-2-phenylcyclopropyl)amino)methyl)piperidin-1-yl)methyl)benzamide di-hydrochloride (114)

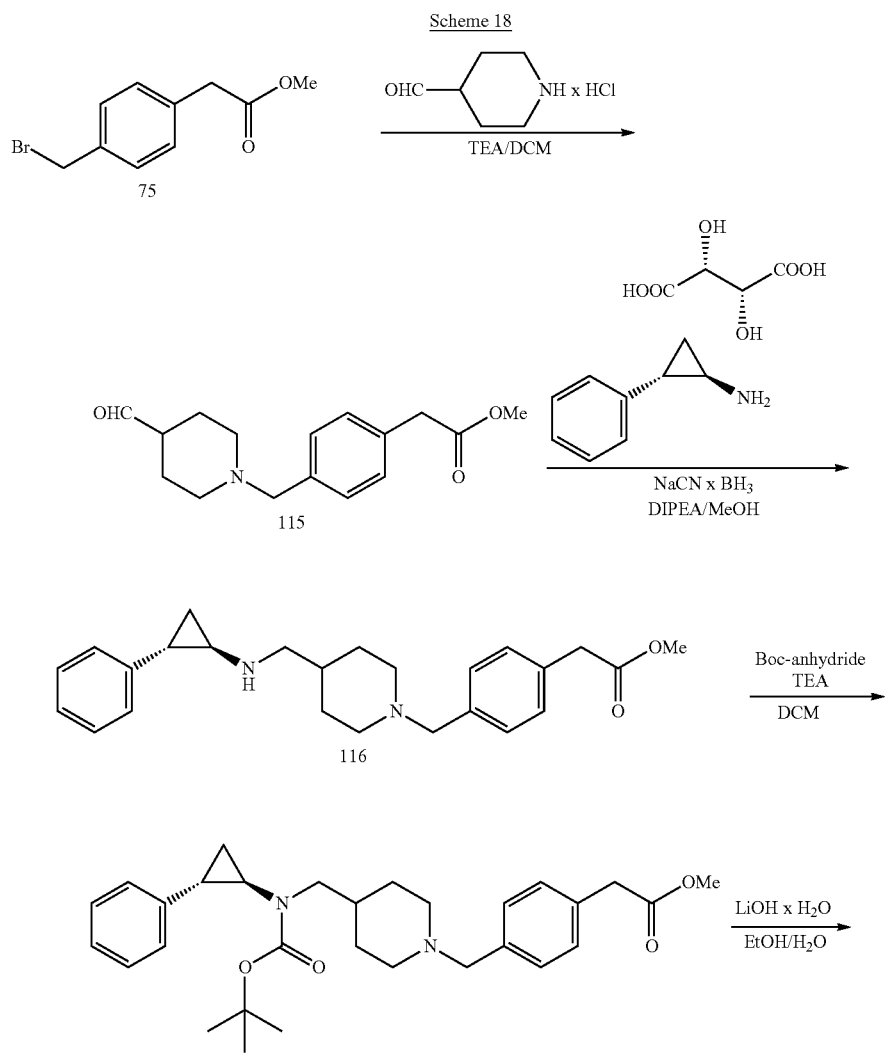

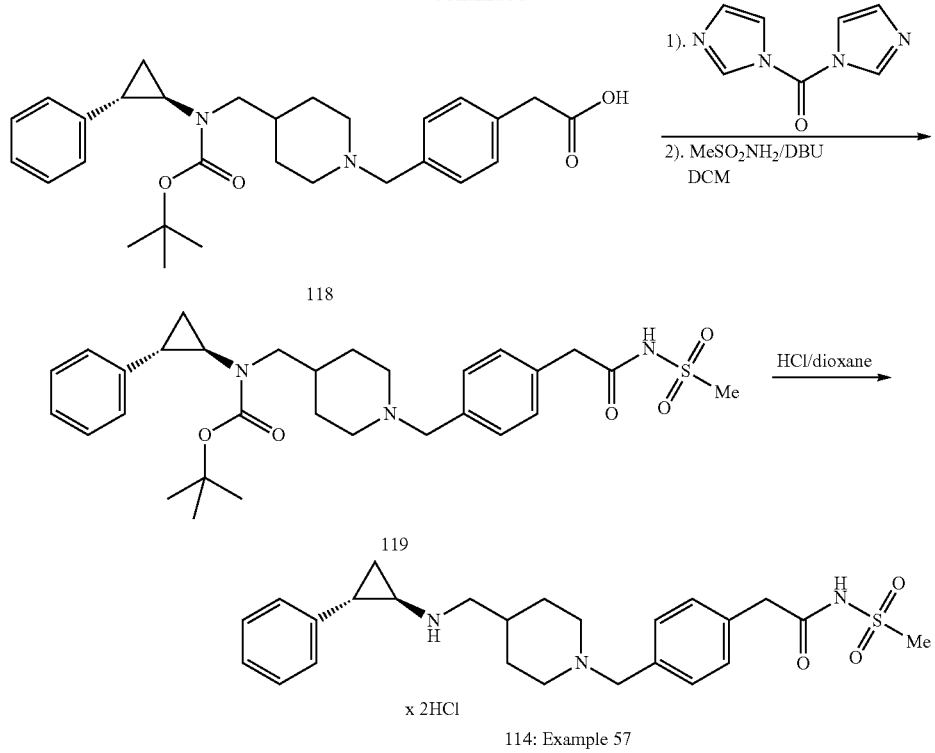

114: Example 57

Step 1. Methyl 2-(4-((4-formylpiperidin-1-yl)methyl)phenyl)acetate (115)

To a solution for the 4-formylpiperidine hydrochloride (1.354 g, 9.05 mmol) in DMF (25 mL) at 0° C. was added dropwise TEA (2.87 mL, 20.57 mmol). The mixture was stirred under these conditions for 5 min then methyl 2-(4-(bromomethyl)phenyl)acetate (75) (2.0 g, 8.23 mmol) was added in small portions. The mixture was stirred for 3 hr at ambient temperature, diluted with brine and extracted with EA. The extract was washed with brine, dried over anhydrous $Na_2SO_4$, filtered, concentrated and the remaining oil was purified by flash column chromatography, eluent EA followed by a second chromatography purification (eluent 20% hexanes in EA) to afford title compound 115 (616 mg, 27% yield).

$^1$H NMR: 500 MHz, $CDCl_3$, δ (ppm): 9.64 (d, J=1.2 Hz, 1H), 7.28-7.25 (m, 2H), 7.23-7.21 (m, 2H), 3.94-3.92 and 3.86-3.83 (two multiplets, rotamers, 1H), 3.694 and 3.690 (two singlets, rotamers, 3H), 3.614 and 3.609 (two singlets, rotamers, 2H), 3.473 and 3.459 (two singlets, rotamers, 2H), 2.92-2.90 and 2.83-2.79 (two multiplets, rotamers, 2H), 2.27-2.20 and 2.12-2.07 (two multiplets, rotamers, 2H), 1.95-1.92 and 1.90-1.64 (two multiplets, rotamers, 2H), 1.72-1.64 (m, 2H). MS: 275.3 (calcd.), 276.1 (M+H$^+$, found).

Step 2. Methyl 2-(4-((4-(((((1R,2S)-2-phenylcyclopropyl)amino)methyl)piperidin-1-yl)methyl)phenyl)acetate (116)

To a suspension of (1R,2S)-2-phenylcyclopropanamine (2R,3R)-2,3-dihydroxysuccinate (761 mg, 2.68 mml) in MeOH (15 mL) was added DIPEA (0.935 mL, 5.37 mmol) and the mixture was stirred until the suspension turned into a clear solution. The solution was added to a solution of the aldehyde 115 (616 mg, 2.237 mmol) in MeOH (15 mL). The resultant mixture was brought to reflux and kept under these conditions for 10 min then cooled to RT. Borohydride (211 mg, 3.36 mmol) was added to the reaction mixture which was stirred for 2 hrs at RT, treated with water (20 mL) and MeOH was evaporated under reduced pressure. The remaining aqueous solution was extracted with DCM. The extract was dried over anhydrous $Na_2SO_4$, filtered and concentrated. The residue was purified by flash column chromatography, eluent 5 then 10% MeOH in DCM (MeOH contained 2% ammonia) to afford title compound 116 (445 mg, 51% yield) as a honey-like material. MS: 392.53 (calcd.), 393.3 (M+H$^+$, found).

Step 3. Methyl 2-(4-((4-(((tert-butoxycarbonyl)((1R,2S)-2-phenylcyclopropyl)amino)methyl)piperidin-1-yl)methyl)phenyl)acetate (117)

To a solution of the compound 116 (445 mg, 1.134 mmol) in DCM (10 mL) was added TEA (0.474 mL, 3.40 mmol). The mixture was cooled by an ice-bath then treated with a solution of the Boc-anhydride (495 mg, 2.267 mmol) in DCM (10 mL). The mixture was stirred at 0-5° C. for 30 min then at ambient temperature for 2 hrs, diluted with DCM, washed with water, dried over anhydrous $Na_2SO_4$, filtered and concentrated. The residue was purified by flash column chromatography, eluent EA-hexanes (8:2) to afford title compound 117 (214 mg, 38% yield) as a honey-like material which was taken to the next step with no extra purification. MS: 492.7 (calcd.), 493.3 (M+H$^+$, found).

Step 4. 2-(4-((4-(((tert-Butoxycarbonyl)((1R,2S)-2-phenylcyclopropyl)amino)methyl)piperidin-1-yl)methyl)phenyl)acetic acid (118)

To a solution of the ester 117 (214 mg, 0.434 mmol) in THF (6 mL) was added a solution of LiOH×$H_2O$ (55 mg, 1.303 mmol) in water (6 mL). The reaction mixture was stirred at rt for 3 hrs, acidified to pH 5-6 with HCl. The acidic solution was evaporated to its maximum to remove THF. The residual aqueous emulsion was diluted with brine and extracted with DCM. The extract was dried over anhydrous $Na_2SO_4$, filtered and concentrated to afford title compound 118 (173 mg, 83% yield) as a honey-like material that was taken to the next step with no extra purification. MS: 478.6 (calcd.), 479.3 (M+H+, found).

Step 5. tert-Butyl ((1-(4-(2-(methylsulfonamido)-2-oxoethyl)benzyl)piperidin-4-yl)methyl)((1R,2S)-2-phenylcyclopropyl)carbamate (119)

To a solution of the acid 118 (173 mg, 0.361 mmol) in DCM at 0° C. was added CDI (117 mg, 0.723 mmol). The reaction mixture was stirred for 5 min, then the ice bath was removed and the mixture was stirred for 1 hour at ambient temperature. To the mixture were then added the sulfonamide (69 mg, 0.723 mmol) and the DBU (0.135 mL, 0.904 mmmol). The combined mixture was stirred overnight, diluted with more DCM and washed with a mixture of 10% aqueous $NaH_2PO_4$ solution and brine. The organic solution was dried over anhydrous $Na_2SO_4$, filtered and evaporated. The residue was purified by flash column chromatgraphy, eluent 20% MeOH in DCM (MeOH contained 2% ammonia) to afford title compound 119 (54 mg, 27% yield) as a honey-like material. MS: 555.7 (calcd.), 556.3 (M+H+, found).

Step 6. N-(Methylsulfonyl)-4-((4-((((1R,2S)-2-phenylcyclopropyl)amino)methyl)piperidin-1-yl)methyl) benzamide di-hydrochloride (114)

To a solution of the compound 119 (54 mg, 0.097 mmol) in dioxane (1 mL) was added a 4M solution of HCl in dioxane (0.73 ml). The reaction mixture was stirred at ambient temperature for 3 hrs, evaporated to dryness and the resultant white precipitate was triturated with EA, collected by filtration and dried in vacuum to afford title compound 114 (45 mg, 88% yield).

$^1$H NMR: 500 MHz, DMSO-$d_6$, δ (ppm): 12.03 (bs, 1H), 10.77 (bs, 1H), 9.62 and 9.00 (bs, 2H), 7.57 (d, J=8.1 Hz, 2H), 7.35 (d, J=8.0 Hz, 2H), 7.32-7.29 (m, 2H), 7.24-7.17 (m, 3H), 4.23 (bs, 2H), 3.68 (s, 2H), 3.25 (s, 3H), 3.07-2.58 (m, 7H), 2.02-1.95 (m, 4H), 1.64-1.57 (m, 3H), 1.26-1.22 (m, 1H). MS: 455.6 (calcd.), 456.2 (M+H+, found).

The compounds of the present invention have one or more chiral center and are synthesized as stereoisomeric mixtures, isomers of identical constitution that differ in the arrangement of their atoms in space. The compounds may be used as mixtures or the individual components/isomers may be separated using reagents and conventional methods for isolation of stereoisomers and enantiomers well-known to those skilled in the art, e.g., using CHIRALPAK® (Sigma-Aldrich) or CHIRALCEL® (Diacel Corp) chiral chromatographic HPLC columns according to the manufacturer's instructions. Alternatively, compounds of the present invention may be synthesized using optically pure, chiral reagents and intermediates to prepare individual isomers or entantiomers. Unless otherwise indicated, all chiral (enantiomeric and diastereomeric) and racemic forms are within the scope of the invention.

Example A

This Example illustrates that exemplary compounds of the present invention inhibit LSD1 enzymatic activity.

Ten-point dose-response curves for compounds of the present invention were determined using a fluorescence coupling enzymatic assay using purified N-terminal truncated human LSD1 enzyme (aa 151-852; Genbank Accession No NM015013) containing an N-terminal His-Tag (Reaction Biology Corp). In this assay, hydrogen peroxide is produced by the LSD1 FAD-dependent demethylase activity using a horseradish peroxidase/Amplex Red coupling reaction resulting in the production of highly fluorescent compound, Resorufin, which is detected at 590 nM.

Briefly, compounds of the present invention were solubilized in DMSO and a series of 10, three-fold serial dilutions were made for each compound in 15% DMSO. The initial starting concentration for the serial dilutions of each compound was 10 μM. Control samples lacking compound, LSD1 enzyme or various reaction components also were prepared and processed in parallel with compound test samples.

An aliquot of each serial dilution of test compound was added to a 96 well plate containing 50 nM purified N-truncated LSD1 enzyme (RBC Cat# PDM-11-350), 50 mM Tris-HCl, pH 7.5, 0.05% CHAPS and 1% DMSO in a 10 microliter reaction volume. The plate was pre-incubated at room temperature for 30 min to which 10 μM of histone 3.3 peptide (aa 1-21) was added to initiate the enzymatic reaction. The reaction mixture was incubated at room temperature for one hour. After one hour, 10 μl of a detection mixture of horseradish peroxidase (Sigma Cat #P8375) and Amplex Red (InVitrogen A36006) was added and kinetic measurements were read at 5 minute intervals for a period of 30 minutes using an Envision Multiplate Reader (PerkinElmer; excitation at 535 nM and emmission read at 590 nM). The $IC_{50}$ value for each compound was determined from each 10-point dose-response curve using GraphPad Prism 4 software with a sigmodial dose response. The results for exemplary compounds of Formula (I) are shown in Table 5.

TABLE 5

Inhibition of LSD1 Activity by Exemplary Compounds of Formula (I)

| Example Number | $IC_{50}$ (nM) |
|---|---|
| 1 | 15 |
| 2 | 30 |
| 3 | 25 |
| 4 | 90 |
| 5 | 10 |
| 6 | 10 |
| 7 | 26 |
| 8 | 27 |
| 9 | 17 |
| 10 | 33 |
| 11 | 22 |
| 12 | 23 |
| 13 | 17 |
| 14 | 118 |
| 15 | 10 |
| 16 | 6 |
| 17 | 51 |
| 18 | 55 |
| 19 | 16 |
| 20 | 42 |
| 21 | 21 |
| 22 | 58 |
| 23 | 14 |
| 24 | 11 |

TABLE 5-continued

Inhibition of LSD1 Activity by Exemplary Compounds of Formula (I)

| Example Number | $IC_{50}$ (nM) |
|---|---|
| 25 | 48 |
| 26 | 12 |
| 27 | 58 |
| 28 | 81 |
| 29 | 133 |
| 30 | 127 |
| 31 | 144 |
| 32 | 122 |
| 33 | 69 |
| 34 | 3 |
| 35 | 25 |
| 36 | 39 |
| 37 | 7 |
| 38 | 6 |
| 39 | 25 |
| 40 | 98 |
| 41 | 69 |
| 42 | 14 |
| 43 | 12 |
| 44 | 5 |
| 45 | 13 |
| 46 | 29 |
| 47 | 12 |
| 48 | 33 |
| 29 | 21 |
| 50 | 20 |
| 51 | 11 |
| 52 | 9 |
| 53 | 27 |
| 54 | 9 |
| 55 | 4 |
| 56 | 43 |
| 57 | 44 |

Example B

This Example illustrates that exemplary compounds of the present invention inhibit the growth of tumor cell lines that express LSD1.

The MV4-11 cell line cell line was established from the blast cells of a 10-year-old male with biphenotypic B-myelomonocytic leukemia. This cell line expresses a leukemic fusion protein (MLL-AF9+), LSD1 and has been shown to be sensitive to inhibitors of LSD1.

Inhibition of LSD1-mediated cellular proliferation by compounds of Formula (I) was measured in a CellTiter Glo luminescence assay (Promega Corp), which determines the number of viable cells by quantitating the amount of ATP, using a BMG LabTech CLARIOStar instrument in accordance with the manufacturer's instructions. Briefly, MV4-11 cells were plated at a density of 1000 cells/90 µl/well in 96 well culture plates and cultured in IMDM medium (Gibco) supplemented with 10% fetal bovine serum (FBS) and 1% penicillin and 1% streptomycin at 37° C. A series of 3-fold serial dilutions of each test compound of Formula (I) was prepared in IMDM medium lacking FBS and added to the cells at final concentrations ranging from 1 µM to 0.01 nM. Control samples lacking test compound or cells were processed in parallel. The plates were incubated at 37° C. for four days and thereafter 50 µl fresh medium containing the same concentration of test compound was added. The plates were incubated for an additional three days (Day 7). A baseline measurement, as described below, was taken for a time zero point at Day 0.

At Day 7, the supernatant was removed by aspiration and the plate was allowed to equilibrate to room temperature (~15 min). The cells were lysed using 45 µl (30 µl for Day 0) of Cell Titer Glo reagent (Promega Corp). The plates were shaken for two minutes and incubated at room temperature for 30 minutes. The degree of inhibition of cell viability was determined using a spectrophotometric readout by measuring the luminescence at 340 nm and the $EC_{50}$ concentration for each compound was calculated using Graph Pad Prism 4 software. The results are shown in Table 6.

TABLE 6

Inhibition of LSD1-mediated Cell Proliferation by Exemplary Compounds of Formula (I)

| Example Number | $EC_{50}$ (nM) |
|---|---|
| 1 | 1 |
| 2 | 14 |
| 3 | 3 |
| 4 | 55 |
| 5 | 1 |
| 6 | 5 |
| 7 | 24 |
| 8 | 13 |
| 9 | 16 |
| 10 | 41 |
| 11 | 15 |
| 12 | 32 |
| 13 | 37 |
| 14 | 174 |
| 15 | <1 |
| 16 | 11 |
| 17 | 8 |
| 18 | 8 |
| 19 | 12 |
| 20 | 12 |
| 21 | <1 |
| 22 | 214 |
| 23 | <1 |
| 24 | 6 |
| 25 | 51 |
| 26 | 6 |
| 27 | 94 |
| 28 | 29 |
| 29 | 33 |
| 30 | 34 |
| 31 | 10 |
| 32 | 35 |
| 33 | 47 |
| 34 | 60 |
| 35 | 30 |
| 36 | 17 |
| 37 | 41 |
| 38 | 13 |
| 39 | 65 |
| 40 | 22 |
| 41 | 9 |
| 42 | 33 |
| 43 | <1 |
| 44 | <1 |
| 45 | 43 |
| 46 | 11 |
| 47 | 11 |
| 48 | 9 |
| 49 | 26 |
| 50 | 11 |
| 51 | 20 |
| 52 | <1 |
| 53 | 19 |
| 54 | 2 |
| 55 | <1 |
| 56 | 3 |
| 57 | 1 |

While the invention has been described in connection with specific embodiments thereof, it will be understood that it is capable of further modifications and this application is intended to cover any variations, uses, or adaptations of the

We claim:
1. A compound of formula (I):

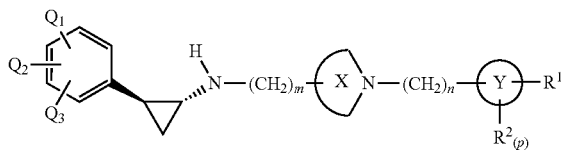

Formula (I)

or a pharmaceutically acceptable salt thereof:
wherein:
X is 4-8 membered saturated monocyclic or bridged nitrogen-containing ring system optionally independently substituted with one or more $C_1$-$C_6$ alkyl, alkoxy, halogen or haloalkyl;
Y is 5-10 membered aryl or 5-10 membered heteroaryl;
$R^1$ is —$C_{1-4}$ alkylene-$R^3$ or —$C_{2-4}$ alkenylene-$R^3$;
each $R^2$ is independently hydrogen, hydroxyl, halogen, cyano, amino, haloalkyl, $C_1$-$C_6$ alkyl, $C_2$-$C_6$ alkenyl, $C_2$-$C_6$ alkynyl, cycloalkyl, heterocyclyl, aryl, heteroaryl, aryloxy, heteroaryloxy, aralkyl, heteroarylalkyl, —C(O)$R^6$, —C(O)N$R^4R^5$, —N$R^4R^5$, —N$R^4$C(O)$R^6$—, or —N$R^4$SO$_2R^6$, wherein each of said $C_1$-$C_6$ alkyl, $C_2$-$C_6$ alkenyl, $C_2$-$C_6$ alkynyl, cycloalkyl, heterocyclyl, aryl, heteroaryl, aryloxy, heteroaryloxy, aralkyl, heteroarylalkyl is optionally independently substituted with one or more $R^6$ or $R^7$;
$R^3$ is aryl, cycloalkyl, or heterocyclyl optionally substituted with one or more $R^7$;
each $R^4$ is independently hydrogen or $C_{1-4}$ alkyl;
each $R^5$ is independently hydrogen, alkoxy, aryloxy, aralkyloxy, wherein said aryloxy and aralkyloxy may be optionally independently substituted on the aryl group with one or more $R^7$;
or $R^4$ and $R^5$ together with the nitrogen atom to which they are attached form a 4-8 membered heterocyclyl, wherein said 4-8 membered heterocyclyl may be optionally independently substituted with one or more $R^6$ or $R^7$;
each $R^6$ is independently hydrogen, $C_1$-$C_6$ alkyl, cycloalkyl, aryl, heteroaryl, aralkyl or heteroarylalkyl, wherein said $C_1$-$C_6$ alkyl, aryl, heteroaryl, arylalkyl and heteroarylalkyl may each be optionally independently substituted with one or more $R^7$;
each $R^7$ is independently hydrogen, halogen, hydroxy, carboxy, amino, nitro, cyano, azido, haloalkyl, $C_1$-$C_4$-alkoxy, $C_1$-$C_4$-alkylthio, $C_1$-$C_4$-alkylsulfonyl, $C_1$-$C_4$-alkylamino, $C_1$-$C_4$-dialkylamino, acetyl, acetylamino, or methylsulfonylamino;
m is 0 or 1;
n is 0 or 1;
p is 0, 1, 2, 3 or 4; and
$Q^1$, $Q^2$ and $Q^3$ are each independently hydrogen, halogen, $CF_3$, $C_1$-$C_4$-alkyl, or $C_1$-$C_4$-alkoxy.

2. A compound of formula (I),

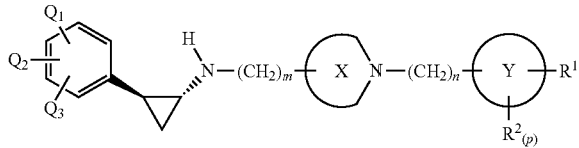

wherein
X is azetidinyl, pyrrolidinyl, or piperidinyl, wherein each of said azetidinyl, pyrrolidinyl, and piperidinyl may be optionally independently substituted with one or more $C_1$-$C_4$ alkyl, alkoxy, halogen or haloalkyl;
Y is phenyl;
$R^1$ is CH$_2$CH=CHC(O)NHOC$_{1-4}$ alkyl, —CH$_2$CH=CHC(O)NHOCH$_2$-aryl, CH$_2$CH=CHC(O)NHSO$_2C_{1-4}$alkyl, or —CH$_2$CH=CHC(O)NHSO$_2$(CH$_2$)$_q$-aryl, wherein q is zero or one;
each $R^2$ is independently hydrogen, hydroxyl, halogen, cyano, amino, haloalkyl, $C_1$-$C_6$ alkyl, $C_2$-$C_6$ alkenyl, $C_2$-$C_6$ alkynyl, cycloalkyl, heterocyclyl, aryl, heteroaryl, aryloxy, heteroaryloxy, aralkyl, heteroarylalkyl, —C(O)$R^6$, —C(O)N$R^4R^5$, —N$R^4R^5$, —N$R^4$C(O)$R^6$—, or —N$R^4$SO$_2R^6$, wherein each of said $C_1$-$C_6$ alkyl, $C_2$-$C_6$ alkenyl, $C_2$-$C_6$ alkynyl, cycloalkyl, heterocyclyl, aryl, heteroaryl, aryloxy, heteroaryloxy, aralkyl, heteroarylalkyl is optionally independently substituted with one or more $R^6$ or $R^7$;
each $R^4$ is independently hydrogen or $C_{1-4}$ alkyl;
each $R^5$ is independently hydrogen, $C_1$-$C_6$ alkyl, alkoxy, aryloxy, aralkyloxy, wherein said aryloxy and aralkyloxy may be optionally independently substituted on the aryl group with one or more $R^7$;
or $R^4$ and $R^5$ together with the nitrogen atom to which they are attached form a 4-8 membered heterocyclyl, wherein said 4-8 membered heterocyclyl may be optionally independently substituted with one or more $R^6$ or $R^7$;
each $R^6$ is independently hydrogen, $C_1$-$C_6$ alkyl, cycloalkyl, aryl, heteroaryl, aralkyl or heteroarylalkyl, wherein said $C_1$-$C_6$ alkyl, aryl, heteroaryl, arylalkyl and heteroarylalkyl may each be optionally independently substituted with one or more $R^7$;
each $R^7$ is independently hydrogen, halogen, hydroxy, carboxy, amino, nitro, cyano, azido, haloalkyl, $C_1$-$C_4$-alkoxy, $C_1$-$C_4$-alkylthio, $C_1$-$C_4$-alkylsulfonyl, $C_1$-$C_4$-alkylamino, $C_1$-$C_4$-dialkylamino, acetyl, acetylamino, or methylsulfonylamino;
m is 0 or 1;
n is 0 or 1;
p is 0, 1, 2, 3 or 4; and
$Q^1$, $Q^2$ and $Q^3$ are each independently hydrogen, halogen, $CF_3$, $C_1$-$C_4$-alkyl, or $C_1$-$C_4$-alkoxy.

3. The compound of claim 1, wherein $R^6$ is $C_1$-$C_4$ alkyl, cycloalkyl, or aryl.

4. The compound of claim 1, wherein $R^3$ is phenyl optionally independently substituted with one or more $R^7$.

5. The compound of claim 1, wherein $R^3$ is azetidinyl, pyrrolidinyl, pyrazolidinyl, piperidinyl, piperazinyl, tetrahydropyranyl, 1,3-dioxolanyl, 1,4-dioxanyl, morpholinyl, thiomorpholinyl, 1,4-dithianyl, or 1,3,5-trithianyl.

6. The compound of claim 1, wherein $R^3$ is:
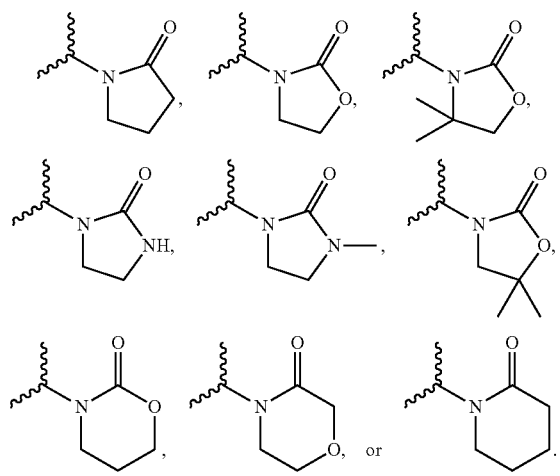
7. The compound of claim 1, wherein $R^3$ is cyclopropanyl, cyclobutanyl, cyclopentyl, cyclohexyl, cycloheptyl, cyclooctyl, norbonanyl or adamantanyl.
8. A compound represented by formula (Ia)-(Ill):
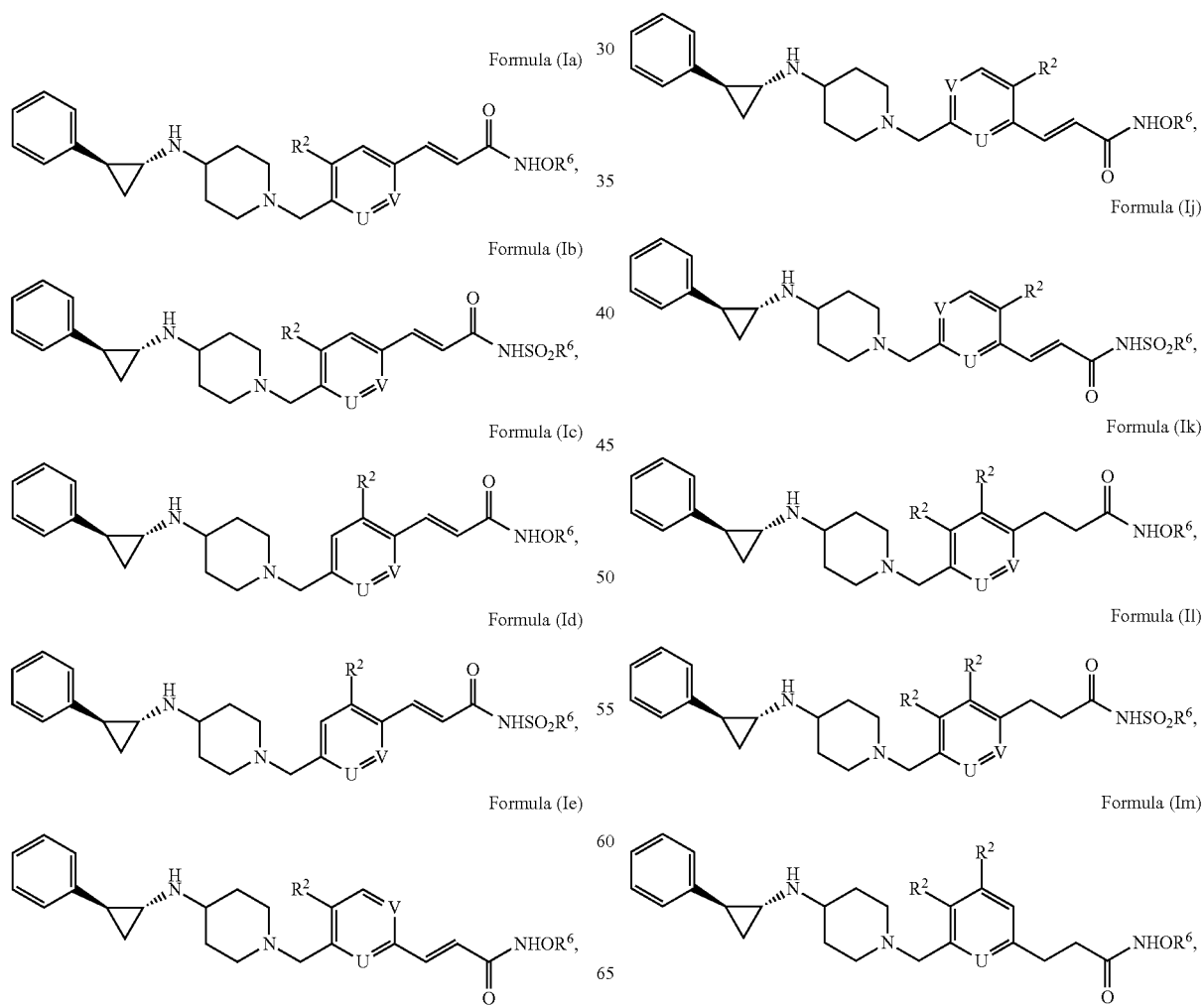
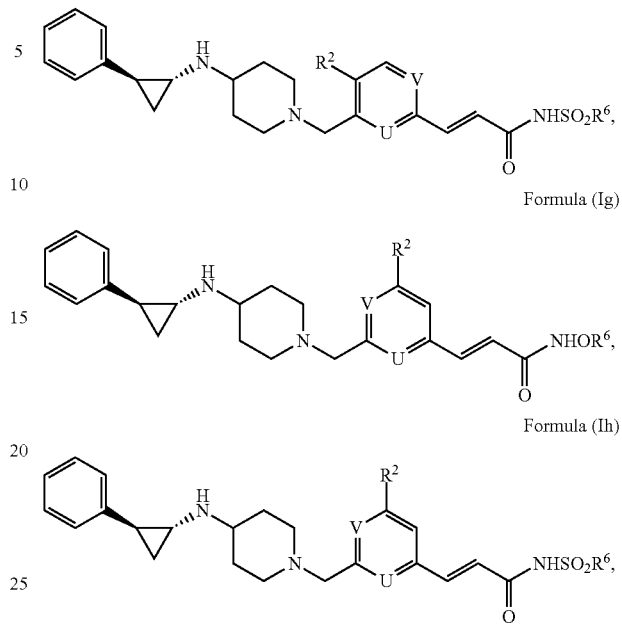

Formula (In)
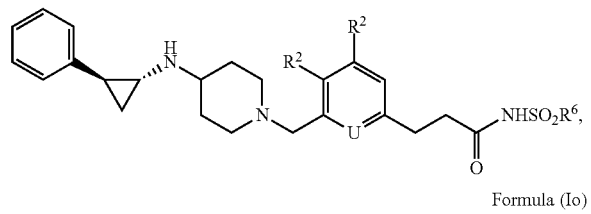
Formula (Io)
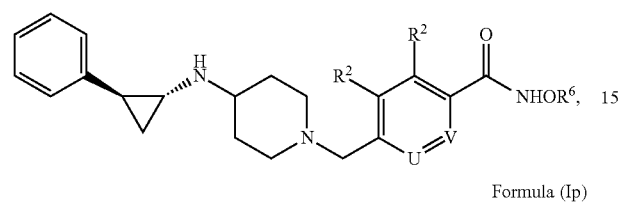
Formula (Ip)
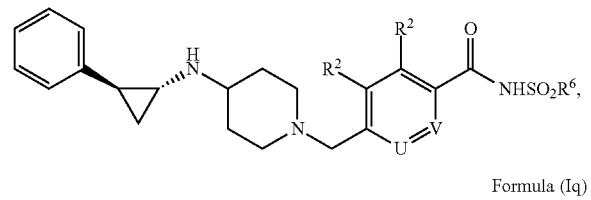
Formula (Iq)
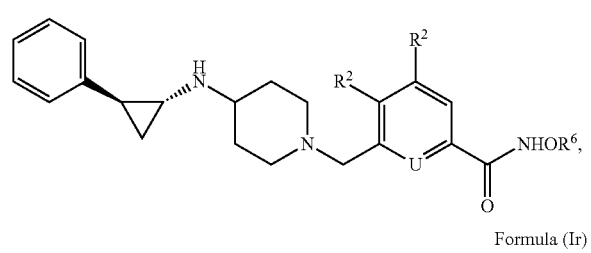
Formula (Ir)
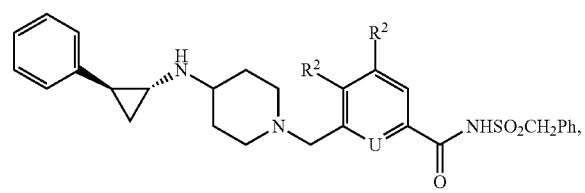
Formula (Is)
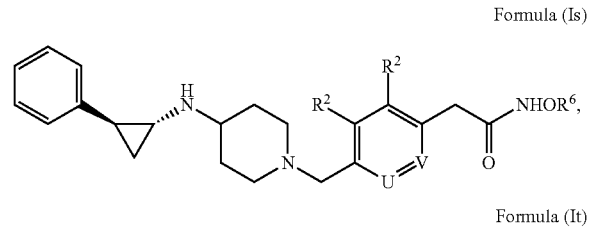
Formula (It)
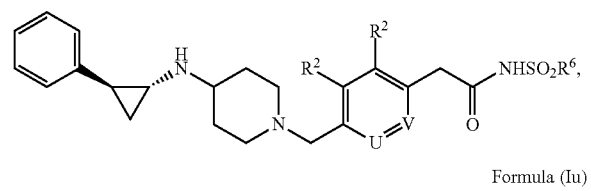
Formula (Iu)
Formula (Iv)
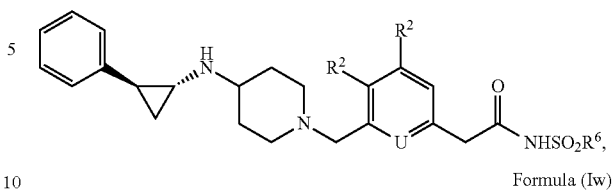
Formula (Iw)
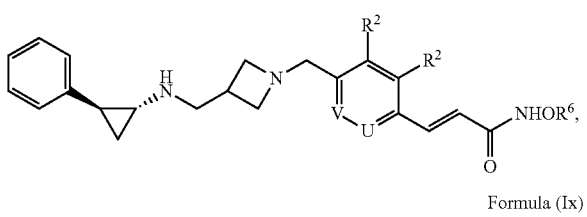
Formula (Ix)
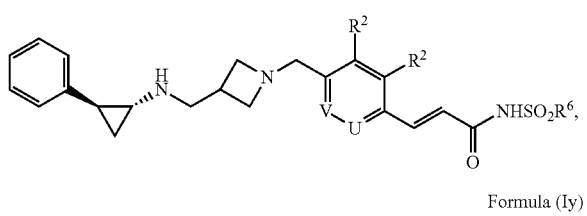
Formula (Iy)
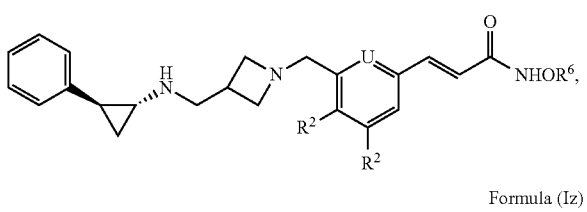
Formula (Iz)
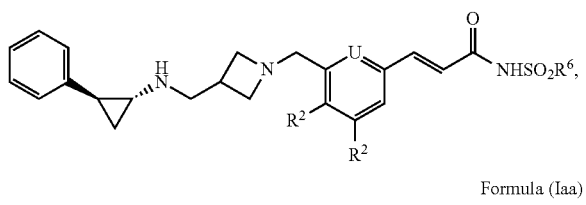
Formula (Iaa)
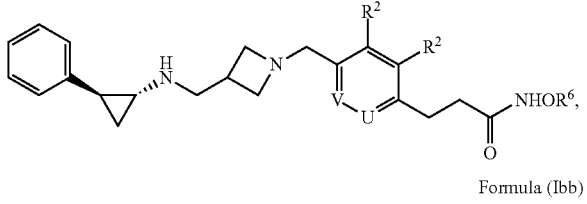
Formula (Ibb)
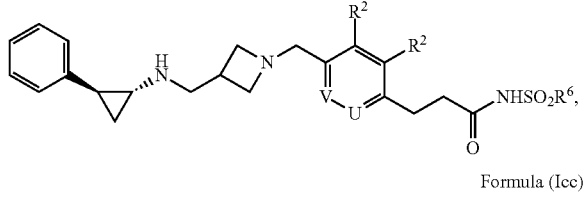
Formula (Icc)
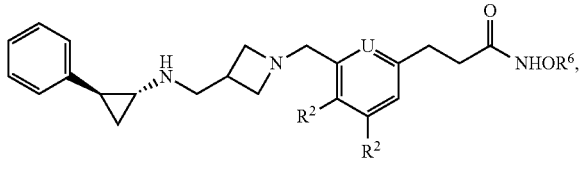

-continued

Formula (Idd)
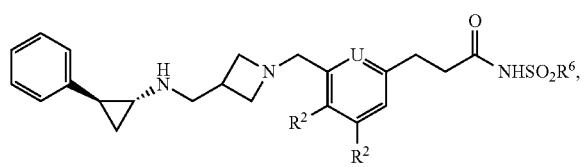

Formula (Iee)
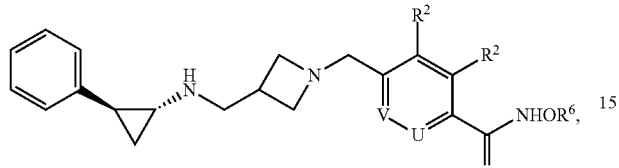

Formula (Iff)
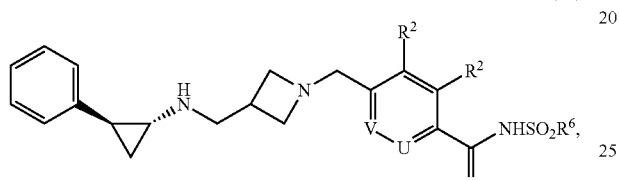

Formula (Igg)
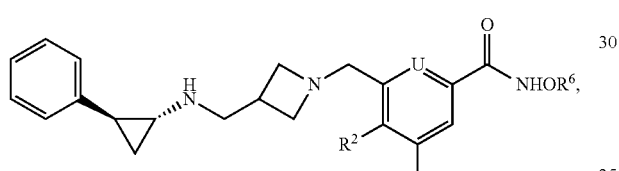

Formula (Ihh)
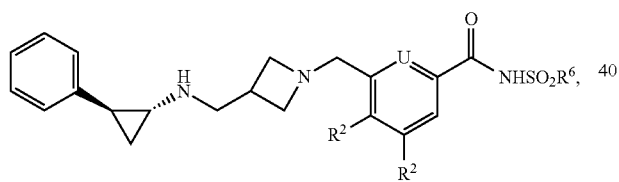

Formula (Iii)
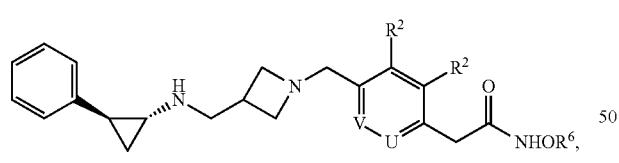

Formula (Ijj)
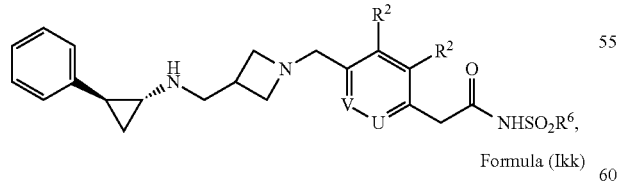

Formula (Ikk)
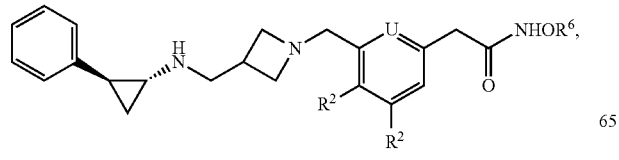

-continued

Formula (Ill)
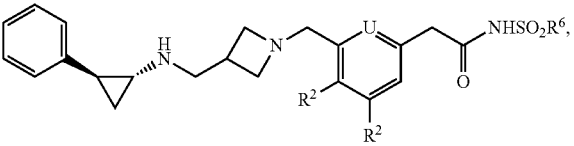

wherein U and V are each independently —CH— or —N—;

each $R^2$ is independently hydrogen, hydroxyl, halogen, cyano, amino, haloalkyl, $C_1$-$C_6$ alkyl, $C_2$-$C_6$ alkenyl, $C_2$-$C_6$ alkynyl, cycloalkyl, heterocyclyl, aryl, heteroaryl, aryloxy, heteroaryloxy, aralkyl, heteroarylalkyl, —C(O)$R^6$, —C(O)N$R^4R^5$, —N$R^4R^5$, —N$R^4$C(O)$R^6$—, or —N$R^4$SO$_2R^6$, wherein each of said $C_1$-$C_6$ alkyl, $C_2$-$C_6$ alkenyl, $C_2$-$C_6$ alkynyl, cycloalkyl, heterocyclyl, aryl, heteroaryl, aryloxy, heteroaryloxy, aralkyl, heteroarylalkyl is optionally independently substituted with one or more $R^6$ or $R^7$;

each $R^4$ is independently hydrogen or $C_{1-4}$ alkyl;

each $R^5$ is independently hydrogen, $C_1$-$C_6$ alkyl, alkoxy, aryloxy, aralkyloxy, wherein said aryloxy and aralkyloxy may be optionally independently substituted on the aryl group with one or more $R^7$;

or $R^4$ and $R^5$ together with the nitrogen atom to which they are attached form a 4-8 membered heterocyclyl, wherein said 4-8 membered heterocyclyl may be optionally independently substituted with one or more $R^6$ or $R^7$;

each $R^6$ is independently hydrogen, $C_1$-$C_6$ alkyl, cycloalkyl, aryl, heteroaryl, aralkyl or heteroarylalkyl, wherein said $C_1$-$C_6$ alkyl, aryl, heteroaryl, arylalkyl and heteroarylalkyl may each be optionally independently substituted with one or more $R^7$; and each $R^7$ is independently hydrogen, halogen, hydroxy, carboxy, amino, nitro, cyano, azido, haloalkyl, $C_1$-$C_4$-alkoxy, $C_1$-$C_4$-alkylthio, $C_1$-$C_4$-alkylsulfonyl, $C_1$-$C_4$-alkylamino, $C_1$-$C_4$-dialkylamino, acetyl, acetylamino, or methylsulfonylamino.

9. The compound of claim 8, wherein the compound is represented by one of:

Formula (Ia)
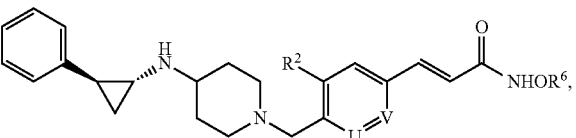

Formula (Ib)
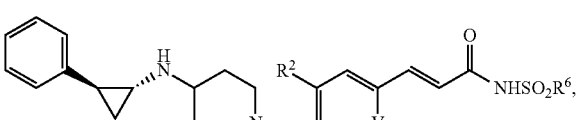

Formula (Ic)
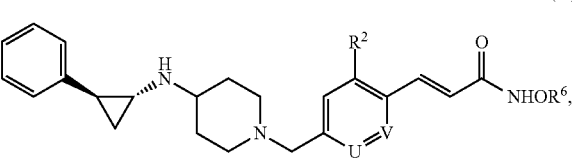

-continued

Formula (Id)
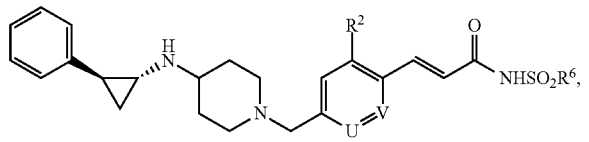

Formula (Ie)
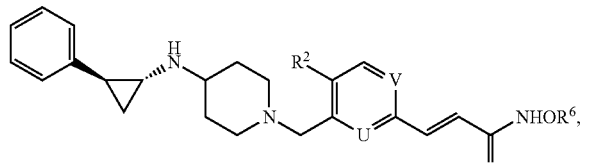

Formula (If)
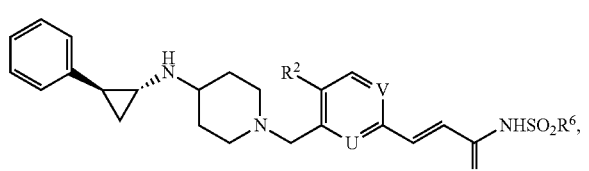

Formula (Ig)
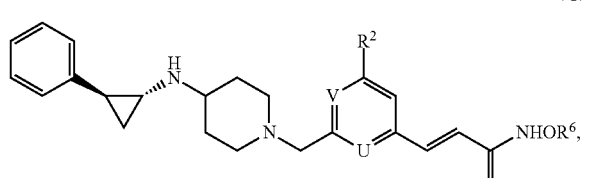

Formula (Ih)
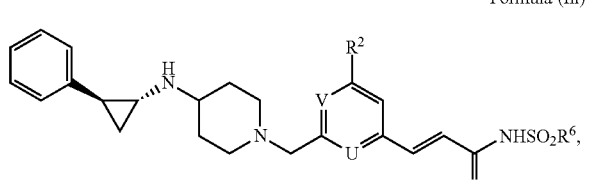

Formula (Ii)
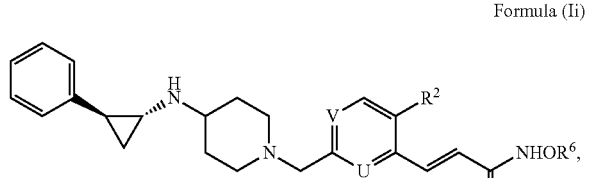

Formula (Ij)
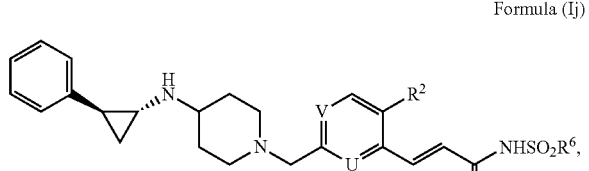

Formula (Iw)
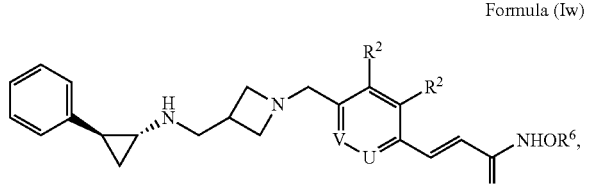

-continued

Formula (Ix)
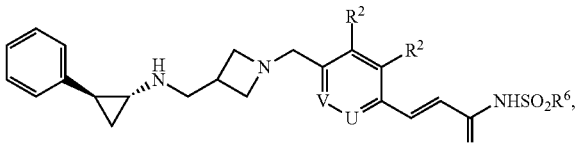

Formula (Iy)
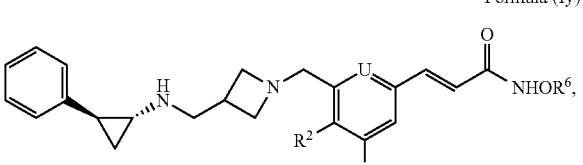

Formula (Iz)
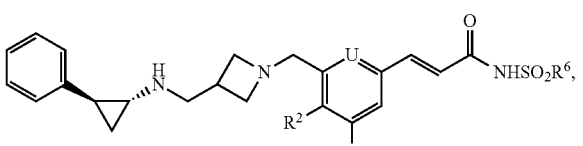

wherein U and V are each independently —CH— or —N—.

10. The compound of any of Formula (Ia)-(Ij), (Iw), (Ix), Iy) or (Iz) of claim 9, wherein each $R^2$ is independently hydrogen or $C_1$-$C_4$ alkyl, and $R^6$ is $C_1$-$C_4$ alkyl, aryl, or aralkyl.

11. A compound that is
(E)-N-Methoxy-3-(4-((4-(((trans)-2-phenylcyclopropyl)amino)piperidin-1-yl)methyl)phenyl)acrylamide;
(E)-N-(Methylsulfonyl)-3-(4-((4-(((trans)-2-phenylcyclopropyl)amino)piperidin-1-yl)methyl)phenyl)acrylamide;
(E)-N-Methoxy-3-(3-((4-(((trans)-2-phenylcyclopropyl)amino)piperidin-1-yl)methyl)phenyl)acrylamide;
(E)-N-(Methylsulfonyl)-3-(3-((4-(((trans)-2-phenylcyclopropyl)amino)piperidin-1-yl)methyl)phenyl)acrylamide;
(E)-N-Phenoxy-3-((4-(((trans)-2-phenylcyclopropyl)amino)piperidin-1-yl)methyl)phenyl)acrylamide;
(E)-N-(Benzyloxy)-3-(4-((4-(((trans)-2-phenylcyclopropyl)amino)piperidin-1-yl)methyl)phenyl)acrylamide;
(E)-3-(4-((4-(((trans)-2-Phenylcyclopropyl)amino)piperidin-1-yl)methyl)phenyl)-N-(phenyl sulfonyl)acrylamide;
(E)-N-(Benzylsulfonyl)-3-(4-((4-(((trans)-2-phenylcyclopropyl)amino)piperidin-1-yl)methyl)phenyl)acrylamide;
(E)-N-(Benzyloxy)-3-(3-((4-(((trans)-2-phenylcyclopropyl)amino)piperidin-1-yl)methyl)phenyl)acrylamide;
(E)-3-(3-((4-(((trans)-2-Phenylcyclopropyl)amino)piperidin-1-yl)methyl)phenyl)-N-(phenyl sulfonyl)acrylamide;
(E)-N-(Benzylsulfonyl)-3-(3-((4-(((trans)-2-phenylcyclopropyl)amino)piperidin-1-yl)methyl)phenyl)acrylamide;
N-trans-2-phenylcyclopropyl)-1-(4-((E)-styryl)benzyl)piperidin-4-amine;
N-(trans-2-phenylcyclopropyl)-1-(3-((E)-styryl)benzyl) piperidin-4-amine;
1-(3-((E)-2-(1H-tetrazol-5-yl)vinyl)benzyl)-N-trans-2-phenylcyclopropyl)piperidin-4-amine;

(E)-N-(Methylsulfonyl)-3-(4-((4-(((1R,2S)-2-phenylcyclopropyl)amino)piperidin-1-yl)methyl)phenyl)acrylamide;

(E)-N-Methyl-N-(methylsulfonyl)-3-(4-((4-(((1R,2S)-2-phenylcyclopropyl)amino)piperidin-1-yl)methyl)phenyl)acrylamide;

(E)-N-(Isopropylsulfonyl)-3-(4-((4-(((1R,2S)-2-phenylcyclopropyl)amino)piperidin-1-yl)methyl)phenyl)acrylamide;

(E)-3-(4-((4-(((1R,2S)-2-Phenylcyclopropyl)amino)piperidin-1-yl)methyl)phenyl)-N-(propyl sulfonyl)acrylamide;

(E)-N-(Ethylsulfonyl)-3-(4-((4-(((1R,2S)-2-phenylcyclopropyl)amino)piperidin-1-yl)methyl)phenyl)acrylamide;

(E)-N-(Ethylsulfonyl)-3-(4-((4-(((trans)-2-phenylcyclopropyl)amino)piperidin-1-yl)methyl)phenyl)acrylamide; or (E)-3-(4-((4-((((1R,2S)-2-Phenylcyclopropyl)amino)methyl)piperidin-1-yl)methyl)phenyl)-N-(phenylsulfonyl)acrylamide;

or a pharmaceutically acceptable salt thereof.

12. The compound of claim 8, wherein the compound is represented by one of:

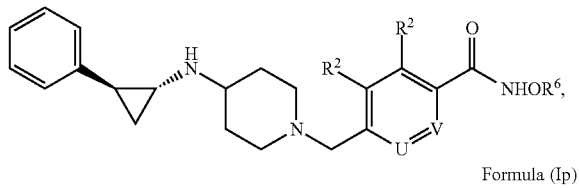
Formula (Io)

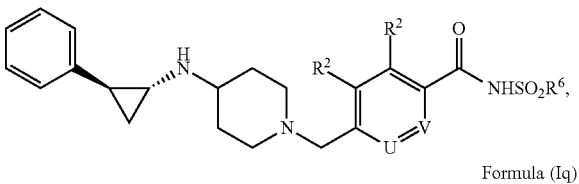
Formula (Ip)

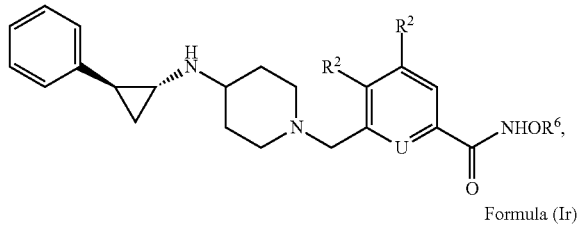
Formula (Iq)

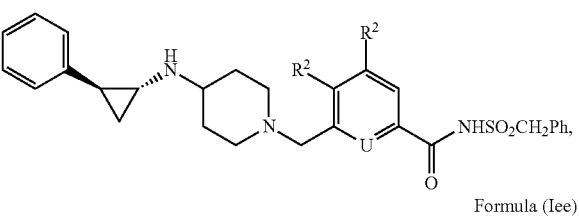
Formula (Ir)

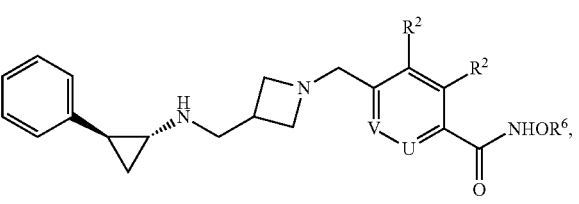
Formula (Iee)

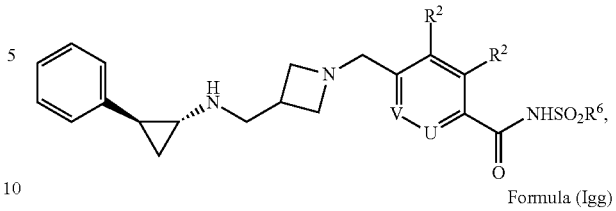
Formula (Iff)

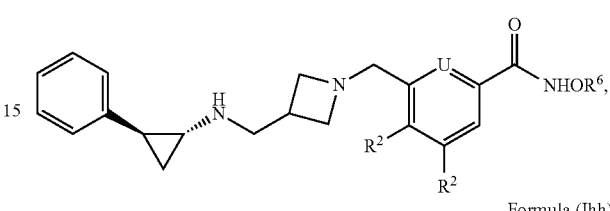
Formula (Igg)

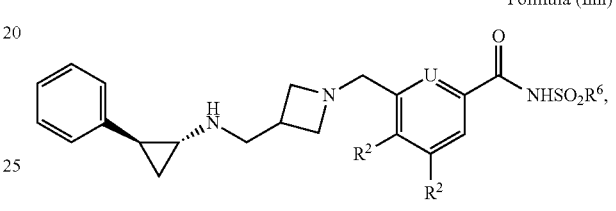
Formula (Ihh)

wherein U and V are each independently —CH— or —N—.

13. The compound of any of Formula (Io)-(Ir) or (Iee)-(Ihh) of claim 12, wherein each $R^2$ is independently hydrogen or $C_1$-$C_4$ alkyl, and $R^6$ is $C_1$-$C_4$ alkyl, aryl, or aralkyl.

14. A compound that is

N-Methoxy-4-((4-(((trans)-2-phenylcyclopropyl)amino)piperidin-1-yl)methyl)benzamide;

N-(Methylsulfonyl)-4-((4-(((trans)-2-phenylcyclopropyl)amino)piperidin-1-yl)methyl)benzamide;

N-(Benzyloxy)-4-((4-(((trans)-2-phenylcyclopropyl)amino)piperidin-1-yl)methyl)benzamide;

N-Phenoxy-4-((4-(((trans)-2-phenylcyclopropyl)amino)piperidin-1-yl)methyl)benzamide;

N-(Benzylsulfonyl)-4-((4-(((trans)-2-phenylcyclopropyl)amino)piperidin-1-yl)methyl)benzamide;

N-Methyl-N-(methylsulfonyl)-4-((4-(((trans)-2-phenylcyclopropyl)amino)piperidin-1-yl)methyl)benzamide;

4-((4-(((trans)-2-Phenylcyclopropyl)amino)piperidin-1-yl)methyl)-N-(phenyl sulfonyl)benzamide;

N-(Isopropylsulfonyl)-4-((4-(((trans)-2-phenylcyclopropyl)amino)piperidin-1-yl)methyl)benzamide;

4-((4-(((trans)-2-Phenylcyclopropyl)amino)piperidin-1-yl)methyl)-N-(propyl sulfonyl)benzamide;

N-(Ethylsulfonyl)-4-((4-(((trans)-2-phenylcyclopropyl)amino)piperidin-1-yl)methyl)benzamide;

N-(tert-Butylsulfonyl)-4-((4-(((trans)-2-phenylcyclopropyl)amino)piperidin-1-yl)methyl)benzamide;

4-((4-(((trans)-2-Phenylcyclopropyl)amino)piperidin-1-yl)methyl)-N-tosylbenzamide;

N-((4-Fluorophenyl)sulfonyl)-4-((4-(((trans)-2-phenylcyclopropyl)amino)piperidin-1-yl)methyl)benzamide;

N-(Methylsulfonyl)-4-((4-(((1R,2S)-2-phenylcyclopropyl)amino)piperidin-1-yl)methyl)benzamide;

N-(Isopropylsulfonyl)-4-((4-(((1R,2S)-2-phenylcyclopropyl)amino)piperidin-1-yl)methyl)benzamide;

4-((4-(((1R,2S)-2-Phenylcyclopropyl)amino)piperidin-1-yl)methyl)-N-(phenyl sulfonyl)benzamide;

N-(cyclopropylsulfonyl)-4-((4-(((1R,2S)-2-phenylcyclopropyl)amino)piperidin-1-yl)methyl)benzamide;

4-((4-(((1R,2S)-2-phenylcyclopropyl)amino)piperidin-1-yl)methyl)-N-(propyl sulfonyl)benzamide;

N-(tert-butylsulfonyl)-4-((4-(((1R,2S)-2-phenylcyclopropyl)amino)piperidin-1-yl)methyl)benzamide;

N-(ethyl sulfonyl)-4-((4-(((1R,2S)-2-phenylcyclopropyl)amino)piperidin-1-yl)methyl)benzamide; or N-methoxy-4-((4-(((1R,2S)-2-phenylcyclopropyl)amino)piperidin-1-yl)methyl)benzamide;

or a pharmaceutically acceptable salt thereof.

15. The compound of claim 8, wherein the compound is represented by one of the following:

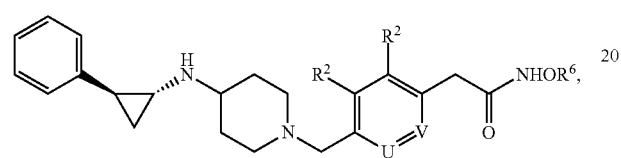
Formula (Is)

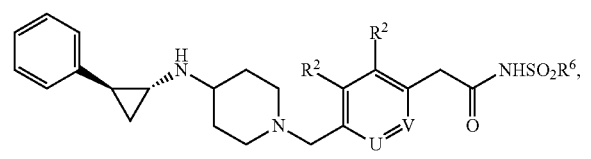
Formula (It)

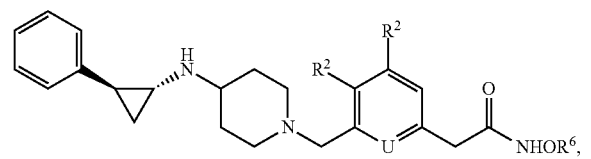
Formula (Iu)

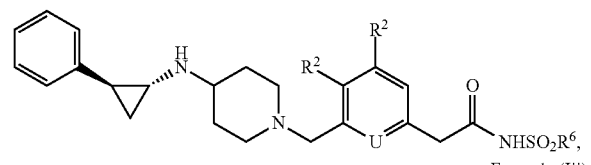
Formula (Iv)

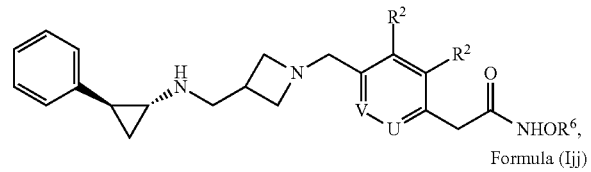
Formula (Iii)

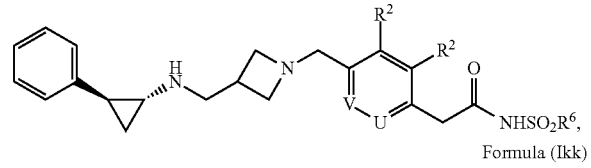
Formula (Ijj)

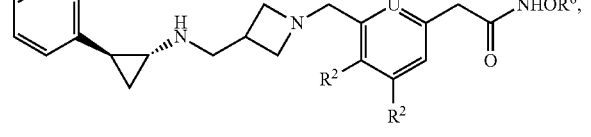
Formula (Ikk)

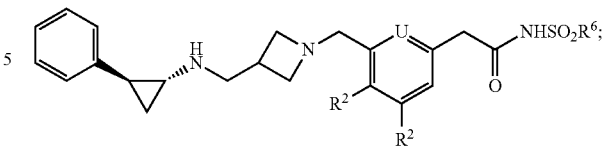
Formula (Ill)

wherein U and V are each independently —CH— or —N—.

16. The compound of any of Formula (Is)-(Iv) or (Iii)-(Ill) of claim 15, wherein each $R^2$ is independently hydrogen or $C_1$-$C_4$ alkyl, and $R^6$ is $C_1$-$C_4$ alkyl, aryl, or aralkyl.

17. A compound that is

N-(Methylsulfonyl)-2-(4-((4-(((1R,2S)-2-phenylcyclopropyl)amino)piperidin-1-yl)methyl)phenyl)acetamide;

2-(4-((4-(((1R,2S)-2-phenylcyclopropyl)amino)piperidin-1-yl)methyl)phenyl)-N-(phenylsulfonyl)acetamide;

N-(cyclopropylsulfonyl)-2-(4-((4-(((1R,2S)-2-phenylcyclopropyl)amino)piperidin-1-yl)methyl)phenyl)acetamide;

N-(ethylsulfonyl)-2-(4-((4-(((1R,2S)-2-phenylcyclopropyl)amino)piperidin-1-yl)methyl)phenyl)acetamide; or N-(isopropylsulfonyl)-2-(4-((4-(((1R,2S)-2-phenylcyclopropyl)amino)piperidin-1-yl)methyl)phenyl)acetamide;

or a pharmaceutically acceptable salt thereof.

18. The compound of claim 1, wherein the compound is

N-ethoxy-4-((4-(((1R,2S)-2-phenylcyclopropyl)amino)piperidin-1-yl)methyl)benzamide;

(E)-N-(methylsulfonyl)-3-(4-((4-((((1R,2S)-2-phenylcyclopropyl)amino)methyl)piperidin-1-yl)methyl)phenyl)acrylamide;

(E)-N-(ethylsulfonyl)-3-(4-((4-((((1R,2S)-2-phenylcyclopropyl)amino)methyl)piperidin-1-yl)methyl)phenyl)acrylamide;

(E)-N-(cyclopropylsulfonyl)-3-(4-((4-((((1R,2S)-2-phenylcyclopropyl)amino)methyl)piperidin-1-yl)methyl)phenyl)acrylamide;

(E)-N-methyl-N-(methylsulfonyl)-3-(4-((4-((((1R,2S)-2-phenylcyclopropyl)amino)methyl)piperidin-1-yl)methyl)phenyl)acrylamide;

N-(cyclopropylsulfonyl)-4-((4-((((1R,2S)-2-phenylcyclopropyl)amino)methyl)piperidin-1-yl)methyl)benzamide;

N-methyl-N-(methylsulfonyl)-4-((4-((((1R,2S)-2-phenylcyclopropyl)amino)methyl)piperidin-1-yl)methyl)benzamide; or 4-((4-((((1R,2S)-2-phenylcyclopropyl)amino)methyl)piperidin-1-yl)methyl)-N-(phenyl sulfonyl)benzamide;

or a pharmaceutically acceptable salt thereof.

19. A composition comprising a compound of claim 1 and a pharmaceutically acceptable excipient.

20. A composition comprising a compound of claim 2 and a pharmaceutically acceptable excipient.

21. A method for treating cancer comprising administering to a patient having cancer a therapeutically effective amount of a compound of claim 1, or a pharmaceutically acceptable salt thereof, alone or combined with a pharmaceutically acceptable carrier, excipient or diluents, wherein the cancer is selected from the group consisting of (i) a cardiac cancer selected from
   a sarcoma selected from the group consisting of angiosarcoma, fibrosarcoma, rhabdomyosarcoma, and liposarcoma,
   myxoma, rhabdomyoma, fibroma, lipoma and teratoma;
(ii) lung cancer selected from
   a bronchogenic carcinoma selected from squamous cell, undifferentiated small cell, undifferentiated large cell, non-small cell, and adenocarcinoma, and
   alveolar (bronchiolar) carcinoma, bronchial adenoma, sarcoma, lymphoma, chondromatous hamartoma, and mesothelioma;
(iii) a gastrointestinal cancer selected from
   esophageal squamous cell carcinoma, adenocarcinoma, leiomyosarcoma, and lymphoma,
   stomach carcinoma, lymphoma, and leiomyosarcoma), pancreatic ductal adenocarcinoma, insulinoma, glucagonoma, gastrinoma, carcinoid tumors, and vipoma,
   small bowel adenocarcinoma, lymphoma, carcinoid tumors, Kaposi's sarcoma, leiomyoma, hemangioma, lipoma, neurofibroma, and fibroma, and
   large bowel adenocarcinoma, tubular adenoma, villous adenoma, hamartoma, and leiomyoma;
(iv) a genitourinary tract cancer selected from
   kidney adenocarcinoma, Wilm's tumor (nephroblastoma), lymphoma, and leukemia),
   bladder and urethra squamous cell carcinoma, transitional cell carcinoma, and adenocarcinoma),
   prostate adenocarcinoma, and
   testis seminoma, teratoma, embryonal carcinoma, teratocarcinoma, choriocarcinoma, sarcoma, interstitial cell carcinoma, fibroma, fibroadenoma, adenomatoid tumors, and lipoma;
(v) a liver cancer selected from
   hepatoma (hepatocellular carcinoma), cholangiocarcinoma, hepatoblastoma, angiosarcoma, hepatocellular adenoma, and hemangioma;
(vi) a biliary tract cancer selected from
   gall bladder carcinoma, ampullary carcinoma, and cholangiocarcinoma;
(vii) a bone cancer selected from
   osteogenic sarcoma (osteosarcoma), fibrosarcoma, malignant fibrous histiocytoma, chondrosarcoma, Ewing's sarcoma, malignant lymphoma (reticulum cell sarcoma), multiple myeloma, malignant giant cell tumor chordoma, osteochronfroma (osteocartilaginous exostoses), benign chondroma, chondroblastoma, chondromyxofibroma, osteoid osteoma and giant cell tumors;
(viii) a nervous system cancer selected from
   skull osteoma, hemangioma, granuloma, xanthoma, and osteitis deformans,
   meninges meningioma, meningiosarcoma, and gliomatosis,
   brain astrocytoma, medulloblastoma, glioma, ependymoma, germinoma (pinealoma), glioblastoma multiform, oligodendroglioma, schwannoma, retinoblastoma, and congenital tumors), and
   spinal cord neurofibroma, meningioma, glioma, and sarcoma);
(ix) a gynecological cancer selected from
   uterine endometrial carcinoma,
   cervical carcinoma and pre-tumor cervical dysplasia,
   ovarian cancer selected from an ovarian carcinoma selected from serous cystadenocarcinoma, mucinous cystadenocarcinoma, and unclassified carcinoma, granulosa-thecal cell tumors, Sertoli-Leydig cell tumors, dysgerminoma, and malignant teratoma),
   vulvan clear cell carcinoma, squamous cell carcinoma, botryoid and sarcoma (embryonal rhabdomyosarcoma), and
   fallopian tubes carcinoma;
(x) a hematologic cancer selected from
   blood cancers myeloid leukemia (acute and chronic), acute lymphoblastic leukemia, chronic lymphocytic leukemia, myeloproliferative diseases, multiple myeloma, and myelodysplastic syndrome),
   Hodgkin's disease, and
   non-Hodgkin's lymphoma (malignant lymphoma);
(xi) a skin cancer selected from
   malignant melanoma, basal cell carcinoma, squamous cell carcinoma, Kaposi's sarcoma, moles dysplastic nevi, lipoma, angioma, dermatofibroma, keloids, and psoriasis; and
(xii) an adredal gland neuroblastoma.

22. The method of claim 21, wherein the cancer is non-small cell lung cancer.

* * * * *